(12) United States Patent
Roux et al.

(10) Patent No.: US 7,425,566 B2
(45) Date of Patent: Sep. 16, 2008

(54) 1,3-DIHYDRO-2H-INDOL-2-ONE DERIVATIVES, PROCESS FOR PREPARING THEM AND PHARMACEUTICAL COMPOSITIONS CONTAINING THEM

(75) Inventors: Richard Roux, Vailhauques (FR); Claudine Serradeil-le Gal, Escalquens (FR); Jean Wagnon, Montpellier (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/064,896

(22) Filed: Feb. 24, 2005

(65) Prior Publication Data

US 2005/0176770 A1 Aug. 11, 2005

Related U.S. Application Data

(62) Division of application No. 10/311,435, filed as application No. PCT/FR01/01919 on Jun. 19, 2001, now Pat. No. 6,864,277.

(30) Foreign Application Priority Data

Jun. 19, 2000 (FR) .................................... 00 07885

(51) Int. Cl.
*A61K 31/454* (2006.01)
*C07D 401/04* (2006.01)
(52) U.S. Cl. ...................... 514/323; 546/201
(58) Field of Classification Search ............... 546/201; 514/323
See application file for complete search history.

(56) References Cited

U.S. PATENT DOCUMENTS 5,338,755 A   8/1994   Wagnon et al.
5,594,023 A   1/1997   Wagnon et al.
5,773,612 A   6/1998   Wagnon et al.

FOREIGN PATENT DOCUMENTS

WO    WO 95 18105 A    7/1995

*Primary Examiner*—Patricia L Morris
(74) *Attorney, Agent, or Firm*—James W. Bolcsak

(57) ABSTRACT

The invention relates to compounds of formula:

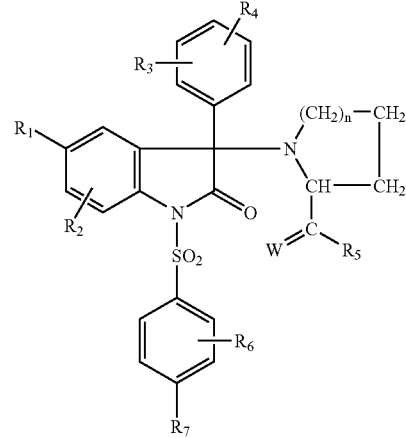

(I)

and to solvates and/or hydrates thereof, with affinity for and selectivity towards the $V_{1b}$ receptors or both the $V_{1b}$ and $V_{1a}$ receptors of arginine-vasopressin.

The invention also relates to a process for preparing them, to the intermediate compounds of formula (II) which are useful for preparing them, to pharmaceutical compositions containing them and to their use for preparing medicinal products.

12 Claims, No Drawings

1,3-DIHYDRO-2H-INDOL-2-ONE DERIVATIVES, PROCESS FOR PREPARING THEM AND PHARMACEUTICAL COMPOSITIONS CONTAINING THEM

This application is a divisional of U.S. application Ser. No. 10/311,435 filed Dec. 16, 2002, now U.S. Pat. No. 6,864,277, which in turn is a 35 U.S.C. §371 application of PCT International Application No. PCT/FR01/01919 files Jun. 19, 2001.

The present invention relates to novel 1,3-dihydro-2H-indol-2-one derivatives, to a process for preparing them and to pharmaceutical compositions containing them.

The compounds according to the present invention have affinity for and selectivity towards the $V_{1b}$ receptors or both the $V_{1b}$ and $V_{1a}$ receptors of arginine-vasopressin (AVP).

AVP is a hormone which is known for its anti-diuretic effect and its effect in regulating arterial pressure. It stimulates several types of receptors: $V_1$ ($V_{1a}$, $V_{1b}$), $V_2$. These receptors are located in particular in the liver, the blood vessels (coronary, renal and cerebral vessels), the platelets, the kidneys, the uterus, the adrenal glands, the pancreas, the central nervous system and the pituitary. AVP thus exerts cardiovascular, hepatic, pancreatic, antidiuretic and platelet-aggregating effects and effects on the central and peripheral nervous system, and on the uterus.

The location of the various receptors is described in: S. Jard et al., Vasopressin and oxytocin receptors: an overview, in *Progress in Endocrinology*, H. Imura and K. Shizurne ed., Experta Medica, Amsterdam, 1988, 1183-1188, and in the following articles: J. Lab. Clin. Med., 1989, 114 (6), 617-632 and Pharmacol. Rev., 1991, 43 (1), 73-108.

More particularly, the AVP $V_{1a}$ receptors are located in many peripheral organs and in the brain. They have been cloned in rats and man and they regulate most of the known effects of AVP: platelet aggregation; uterine contractions; blood vessel contraction; secretion of aldosterone, cortisol, CRF (corticotropin-releasing factor) and ACTH (adrenocorticotrophic hormone); hepatic glycogenolysis, cell proliferation and the main central effects of AVP (hypothermia, memory, etc.).

The $V_{1b}$ receptors were initially identified in the adenohypophysis of various animal species (rat, pig, cattle, sheep, etc.), including man (S. Jard et al., Mol. Pharmacol., 1986, 30, 171-177; Y. Arsenijevic et al., J. Endocrinol., 1994, 141, 383-391; J. Schwartz et al., Endocrinology, 1991, 129 (2), 1107-1109; Y. De Keyser et al., FEBS Letters, 1994, 356, 215-220) in which they stimulate the release of adenocorticotrophic hormone via AVP and potentiate the effects of CRF on the release of ACTH (G. E. Gillies et al., Nature, 1982, 299, 355). In the hypothalamus, the $V_{1b}$ receptors also induce a direct release of CRF (Neuroendocrinology, 1994, 60, 503-508) and are, in these various respects, involved in stress conditions.

These $V_{1b}$ receptors have been cloned in rats, man and mice (Y. De Keyser, FEBS Letters, 1994, 356, 215-220; T. Sugimoto et al., J. Biol. Chem., 1994, 269 (43), 27088-27092; M. Saito et al., Biochem. Biophys. Res. Commun., 1995, 212 (3), 751-757; S. J. Lolait et al., Neurobiology, 1996, 92, 6783-6787; M. A. Ventura et al., Journal of Molecular endocrinology, 1999, 22, 251-260) and various studies (in situ hybridization, PCR (Polymerase Chain Reaction), etc.) reveal the ubiquitous presence of these receptors in various central tissues (brain, hypothalamus and adenohypophysis in particular) and peripheral tissues (kidney, pancreas, adrenal glands, heart, lungs, intestine, stomach, liver, mesentery, bladder, thymus, spleen, uterus, retina, thyroid, etc.) and in certain tumours (pituitary, pulmonary, etc. tumours) suggesting a broad biological and/or pathological role for these receptors and a potential involvement in various diseases.

By way of example, in rats, studies have shown that AVP regulates the endocrine pancreas via the $V_{1b}$ receptors, by stimulating the secretion of insulin and glucagon (B. Lee et al., Am. J. Physiol. 269 (Endocrinol. Metab. 32): E1095-E1100, 1995) or the production of catecholamines in the adrenal medullary which is the site of a local synthesis of AVP (E. Grazzini et al., Endocrinology, 1996, 137 (a), 3906-3914). Thus, in the medullary tissue, AVP via these receptors is thought to have a crucial role in certain types of adrenal pheochromocytomas secreting AVP and thereby inducing a sustained production of catecholamines which is the cause of hypertension conditions that are resistant to angiotensin II receptor antagonists and to conversion enzyme inhibitors. The adrenal cortex is also rich in $V_{1a}$ receptors involved in the production of glucocorticoids and mineralocorticoids (aldosterone and cortisol). Via these receptors, AVP (circulating or synthesized locally) may induce a production of aldosterone with an efficacy comparable to that of angiotensin II (G. Guillon et al., Endocrinology, 1995, 136 (3), 1285-1295). Cortisol is a powerful regulator of the production of ACTH, the stress hormone.

Recent studies have also shown that the adrenal glands are capable of releasing CRF and/or ACTH directly via activation of the $V_{1b}$ and/or $V_{1a}$ receptors borne by the medullary cells (G. Mazzocchi et al., Peptides, 1997, 18 (2), 191-195; E. Grazzini et al., J. Clin. Endocrinol. Metab., 1999, 84 (6), 2195-2203).

The $V_{1b}$ receptors are also considered as a marker of ACTH-secreting tumours such as certain pituitary tumours, certain bronchial carcinomas (SCLCs (Small-Cell Lung Cancers)), pancreatic, adrenal and thyroid carcinomas, inducing Cushing's syndrome in certain cases (J. Bertherat et al., Eur. J. Endocrinol., 1996, 135, 173; G. A. Wittert et al., Lancet, 1990, 335, 991-994; G. Dickstein et al., J. Clin. Endorcinol. Metab., 1996, 81 (8), 2934-2941). As regards the $V_{1a}$ receptors, these are a marker more specific for small-cell lung cancers (SCLCs) (P. J. Woll et al., Biochem. Biophys. Res. Commun., 1989, 164 (1), 66-73). Thus, the compounds according to the present invention are obvious diagnostic tools and offer a novel therapeutic approach in the proliferation and detection of these tumours, even at an early stage (radiolabelling; SPECT (Single Photon Emission Computed Tomography); PET Scan (Positron Emission Tomography Scanner)).

The abundant presence of the $V_{1b}$ receptor messenger in the stomach and intestine suggests an involvement of AVP via this receptor on the release of gastrointestinal hormones such as choleocystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409-413).

1,3-Dihydro-2H-indol-2-one derivatives have been disclosed in certain patent applications as ligands of the arginine-vasopressin receptors and/or the ocytocin receptors: mention may be made of patent applications WO 93/15051, EP 636 608, EP 636 609, WO 95/18105, WO 97/15556 and WO 98/25901.

To date, no non-peptide compound with affinity for and selectivity towards the $V_{1b}$ receptors or both the $V_{1b}$ and $V_{1a}$ receptors of arginine-vasopressin is known.

Novel 1,3-dihydro-2H-indol-2-one derivatives have now been found which show affinity for and selectivity towards the $V_{1b}$ receptors or both the $V_{1b}$ and $V_{1a}$ receptors of arginine-vasopressin.

These compounds may be used to prepare medicinal products that are useful in treating or preventing any pathology in which arginine-vasopressin and/or the $V_{1b}$ receptors or both the $V_{1b}$ receptors and the $V_{1a}$ receptors are involved, in particular in treating or preventing complaints of the cardiovascular system, for example hypertension; of the central nervous system, for example stress, anxiety, depression, obsessive-compulsive disorder and panic attacks; of the renal system; of the gastric system, and also in treating small-cell lung cancers; obesity; type II diabetes; insulin resistance; hypertriglyceridaemia; atherosclerosis; Cushing's syndrome; any pathology resulting from stress and chronic stress conditions.

Thus, according to one of its aspects, the present invention relates to compounds of formula:

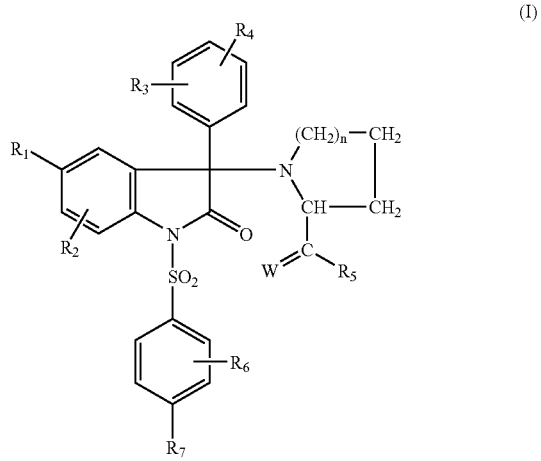

(I)

in which:
n is 1 or 2;
W represents an oxygen atom or a sulphur atom;
$R_1$ represents a halogen atom; a $(C_1-C_4)$alkyl; a $(C_1-C_4)$alkoxy; a trifluoromethyl radical; a trifluoromethoxy radical;
$R_2$ represents a hydrogen atom; a halogen atom; a $(C_1-C_4)$alkyl; a $(C_1-C_4)$alkoxy; a trifluoromethyl radical;
or $R_2$ is in position -6- of the indol-2-one ring and $R_1$ and $R_2$ together represent a trimethylene radical;
$R_3$ represents a halogen atom; a hydroxyl; a $(C_1-C_2)$alkyl; a $(C_1-C_2)$alkoxy; a trifluoromethoxy radical;
$R_4$ represents a hydrogen atom; a halogen atom; a $(C_1-C_2)$alkyl; a $(C_1-C_2)$alkoxy;
or $R_3$ is in position -2- of the phenyl, $R_4$ is in position -3- of the phenyl and $R_3$ and $R_4$ together represent a methylenedioxy radical;
$R_5$ represents an ethylamino group; a dimethylamino group; a 1-azetidinyl radical; a $(C_1-C_2)$alkoxy;
$R_6$ represents a $(C_1-C_4)$alkoxy;
$R_7$ represents a $(C_1-C_4)$alkoxy;

as well as the solvates and/or hydrates thereof.

The compounds of formula (I) comprise at least 2 asymmetric carbon atoms. The optically pure isomers of the compounds of formula (I) and the mixtures thereof in all proportions form part of the invention.

The term "halogen atom" means a chlorine, bromine, fluorine or iodine atom.

The terms "alkyl" and "alkoxy", respectively, mean a linear or branched alkyl radical or alkoxy radical, respectively.

According to the present invention, the compounds of formula (I) that are preferred are those in which:
n is 1 or 2;
W represents an oxygen atom or a sulphur atom;
$R_1$ represents a halogen atom; a $(C_1-C_4)$alkyl; a trifluoromethyl radical; a tri-fluoromethoxy radical;
$R_2$ represents a hydrogen atom; a halogen atom; a $(C_1-C_4)$alkyl; a $(C_1-C_4)$alkoxy; a trifluoromethyl radical;
or $R_2$ is in position -6- of the indol-2-one ring and $R_1$ and $R_2$ together represent a trimethylene radical;
$R_3$ represents a halogen atom; a hydroxyl; a $(C_1-C_2)$alkoxy; a trifluoromethoxy radical;
$R_4$ represents a hydrogen atom; a halogen atom; a $(C_1-C_2)$alkyl; a $(C_1-C_2)$alkoxy;
or $R_3$ is in position -2- of the phenyl, $R_4$ is in position -3- of the phenyl and $R_3$ and $R_4$ together represent a methylenedioxy radical;
$R_5$ represents an ethylamino group; a dimethylamino group; a 1-azetidinyl radical; a $(C_1-C_2)$alkoxy;
$R_6$ represents a $(C_1-C_4)$alkoxy;
$R_7$ represents a $(C_1-C_4)$alkoxy;

as well as the solvates and/or hydrates thereof.

According to the present invention, the compounds of formula (I) that are preferred are those in which W represents an oxygen atom.

According to the present invention, the compounds of formula (I) that are preferred are those in which $R_1$ represents a chlorine atom, a methyl radical or a trifluoromethoxy radical.

According to the present invention, the compounds of formula (I) that are preferred are those in which $R_2$ represents a hydrogen atom, a chlorine atom, a fluorine atom, a methyl radical, a methoxy radical or a trifluoromethyl radical; or $R_2$ is in position -6- of the indol-2-one and, together with $R_1$, represents a trimethylene radical.

According to the present invention, the compounds of formula (I) that are preferred are those in which $R_3$ represents a chlorine atom, a fluorine atom, a hydroxyl, a methoxy radical, an ethoxy radical or a trifluoromethoxy radical.

According to the present invention, the compounds of formula (I) that are preferred are those in which $R_4$ represents a hydrogen atom, a methoxy radical or a methyl radical; or $R_4$ is in position -3- of the phenyl and, together with $R_3$ in position 2, represents a methylenedioxy radical.

According to the present invention, the compounds of formula (I) that are preferred are those in which $R_5$ represents a dimethylamino group, an ethylamino group, a 1-azetidinyl radical or a methoxy radical.

According to the present invention, the compounds of formula (I) that are preferred are those in which $R_6$ is in position -2- of the phenyl and represents a methoxy radical.

According to the present invention, the compounds of formula (I) that are preferred are those in which $R_7$ represents a methoxy radical.

More particularly, the compounds of formula (I) that are preferred are those in which:
n is 1 or 2;
W represents an oxygen atom;
$R_1$ represents a chlorine atom or a methyl radical;
$R_2$ represents a hydrogen atom or is in position -6- of the indol-2-one and represents a chlorine atom, a methyl radical, a methoxy radical or a trifluoromethyl radical;

$R_3$ is in position -2- of the phenyl and represents a methoxy radical, a chlorine atom or a fluorine atom;

$R_4$ represents a hydrogen atom, a methyl radical or a methoxy radical;

or $R_3$ is in position -2- of the phenyl, $R_4$ is in position -3- of the phenyl and $R_3$ and $R_4$ together represent a methylenedioxy radical;

$R_5$ represents a dimethylamino group or a methoxy radical;

$R_6$ is in position -2- of the phenyl and represents a methoxy radical;

$R_7$ represents a methoxy radical;

as well as the solvates and/or hydrates thereof.

According to the present invention, the compounds of formula (I) in the form of optically pure isomers are preferred.

More particularly, the optically pure isomers of the compounds of formula:

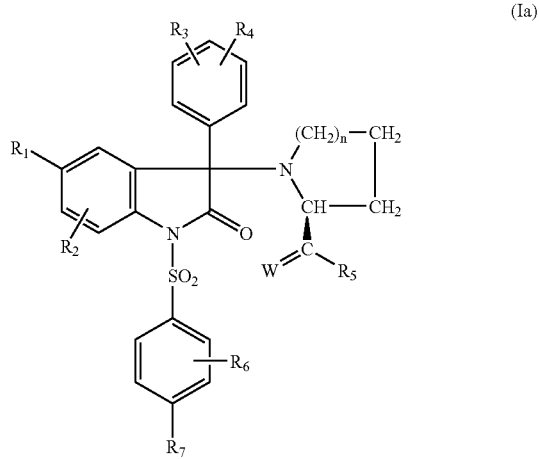

(Ia)

in which n, W, $R_1$, $R_2$, $R_3$, $R_4$, $R_5$, $R_6$ and $R_7$ are as defined for a compound of formula (I), the carbon atom bearing the substituent $C(W)R_5$ has the (S) configuration and the carbon atom in position 3 of the indol-2-one has either the (R) configuration or the (S) configuration, are preferred.

Most particularly, the laevorotatory isomer of the compounds of formula (Ia) is preferred.

The following compounds:

(2S)-1-[5-Chloro-1-[(2,4-dimethoxyphenyl)-sulphonyl]-3-(2-methoxyphenyl)-2-oxo-2,3-dihydro-1H-indol-3-yl]-N,N-dimethylpyrrolidine-2-carboxamide, laevorotatory isomer;

(2S)-1-[5,6-Dichloro-1-[(2,4-dimethoxyphenyl)-sulphonyl]-3-(2-methoxyphenyl)-2-oxo-2,3-dihydro-1H-indol-3-yl]-N,N-dimethylpyrrolidine-2-carboxamide, laevorotatory isomer;

(2S)-1-[6-Chloro-1-[(2,4-dimethoxyphenyl)-sulphonyl]-3-(2-methoxyphenyl)-5-methyl-2-oxo-2,3-dihydro-1H-indol-3-yl]-N,N-dimethylpyrrolidine-2-carboxamide, laevorotatory isomer;

(2S)-1-[5,6-Dichloro-1-[(2,4-dimethoxyphenyl)-sulphonyl]-3-(2-chlorophenyl)-2-oxo-2,3-dihydro-1H-indol-3-yl]-N,N-dimethylpiperidine-2-carboxamide, laevorotatory isomer;

(2S)-1-[5-Chloro-1-[(2,4-dimethoxyphenyl)-sulphonyl]-3-(2,3-dimethoxyphenyl)-2-oxo-2,3-dihydro-1H-indol-3-yl]-N,N-dimethylpyrrolidine-2-carboxamide, laevorotatory isomer;

(2S)-1-[5-Chloro-1-[(2,4-dimethoxyphenyl)-sulphonyl]-3-(2,4-dimethoxyphenyl)-2-oxo-2,3-dihydro-1H-indol-3-yl]-N,N-dimethylpyrrolidine-2-carboxamide, laevorotatory isomer;

(2S)-1-[5-Chloro-1-[(2,4-dimethoxyphenyl)-sulphonyl]-3-(2,6-dimethoxyphenyl)-2-oxo-2,3-dihydro-1H-indol-3-yl]-N,N-dimethylpyrrolidine-2-carboxamide, laevorotatory isomer;

(2S)-1-[3-(1,3-Benzodioxol-4-yl)-5-chloro-1-[(2,4-dimethoxyphenyl)sulphonyl]-2-oxo-2,3-dihydro-1H-indol-3-yl]-N,N-dimethylpyrrolidine-2-carboxamide, laevorotatory isomer;

(2S)-1-[5-Chloro-3-(2-fluorophenyl)-1-[(2,4-dimethoxyphenyl)sulphonyl]-2-oxo-2,3-dihydro-1H-indol-3-yl]-N,N-dimethylpyrrolidine-2-carboxamide, laevorotatory isomer;

(2S)-1-[5-Chloro-1-[(2,4-dimethoxyphenyl)-sulphonyl]-3-(2-methoxy-6-methylphenyl)-2-oxo-2,3-dihydro-1H-indol-3-yl]-N,N-dimethylpyrrolidine-2-carboxamide, laevorotatory isomer;

(2S)-1-[5,6-Dichloro-3-(2-chlorophenyl)-1-[(2,4-dimethoxyphenyl)sulphonyl]-2-oxo-2,3-dihydro-1H-indol-3-yl]-N,N-dimethylpyrrolidine-2-carboxamide, laevorotatory isomer;

(2S)-1-[4,5-Dichloro-3-(2-chlorophenyl)-1-[(2,4-dimethoxyphenyl)sulphonyl]-2-oxo-2,3-dihydro-1H-indol-3-yl]-N,N-dimethylpyrrolidine-2-carboxamide, laevorotatory isomer;

(2S)-1-[5-Chloro-1-[(2,4-dimethoxyphenyl)-sulphonyl]-3-(2-methoxyphenyl)-6-methyl-2-oxo-2,3-dihydro-1H-indol-3-yl]-N,N-dimethylpyrrolidine-2-carboxamide, laevorotatory isomer;

(2S)-1-[5-Chloro-3-(2-chlorophenyl)-1-[(2,4-dimethoxyphenyl)sulphonyl]-6-methoxy-2-oxo-2,3-dihydro-1H-indol-3-yl]-N,N-dimethylpyrrolidine-2-carboxamide, laevorotatory isomer;

(2S)-1-[5,6-Dimethyl-3-(2-methoxy-6-methylphenyl)-1-[(2,4-dimethoxyphenyl)sulphonyl]-2-oxo-2,3-dihydro-1H-indol-3-yl]-N,N-dimethylpyrrolidine-2-carboxamide, laevorotatory isomer;

(2S)-1-[5,6-Dichloro-1-[(2,4-dimethoxyphenyl)-sulphonyl]-3-(2-methoxyphenyl)-2-oxo-2,3-dihydro-1H-indol-3-yl]-N,N-dimethylpiperidine-2-carboxamide, laevorotatory isomer;

(2S)-1-[5-Chloro-1-[(2,4-dimethoxyphenyl)-sulphonyl]-3-(2-methoxyphenyl)-6-methyl-2-oxo-2,3-dihydro-1H-indol-3-yl]-N,N-dimethylpiperidine-2-carboxamide, laevorotatory isomer;

(2S)-1-[5-Chloro-1-[(2,4-dimethoxyphenyl)-sulphonyl]-3-(2-methoxyphenyl)-6-trifluoromethyl-2-oxo-2,3-dihydro-1H-indol-3-yl]-N,N-dimethylpiperidine-2-carboxamide, laevorotatory isomer;

as well as the solvates and/or hydrates thereof, are more particularly preferred.

According to another of its aspects, a subject of the present invention is a process for preparing the compounds of formula (I), solvates thereof and/or hydrates thereof, characterized in that:

a compound of formula:

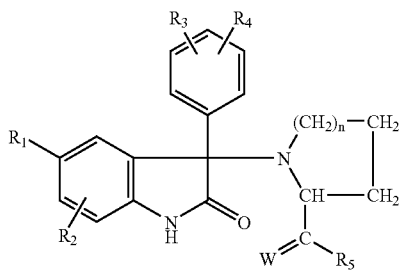

(II)

in which n, W, $R_1$, $R_2$, $R_3$, $R_4$ and $R_5$ are as defined for a compound of formula (I), is reacted, in the presence of a base, with a halide of formula:

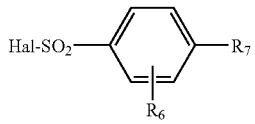

(III)

in which $R_6$ and $R_7$ are as defined for a compound of formula (I) and Hal represents a halogen atom.

The reaction is carried out in the presence of a strong base, for instance a metal hydride such as sodium hydride or an alkali metal alkoxide such as potassium tert-butoxide, in an anhydrous solvent such as N,N-dimethylformamide or tetrahydrofuran and at a temperature of between −70° C. and +60° C. The reaction is preferably carried out using a compound of formula (III) in which Hal=Cl.

According to one variant of the process and when $R_5$ represents an ethylamino group, a dimethylamino group or a 1-azetidinyl radical and W represents an oxygen atom:

a) a compound of formula:

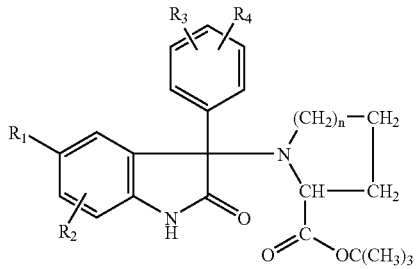

(II')

in which n, $R_1$, $R_2$, $R_3$ and $R_4$ are as defined for a compound of formula (I), is reacted, in the presence of a base, with a halide of formula:

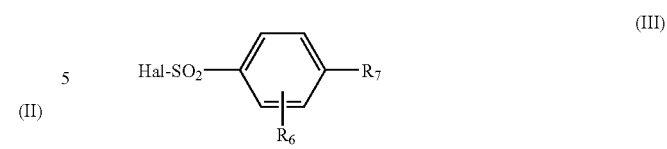

(III)

in which $R_6$ and $R_7$ are as defined for a compound of formula (I), to give a compound of formula:

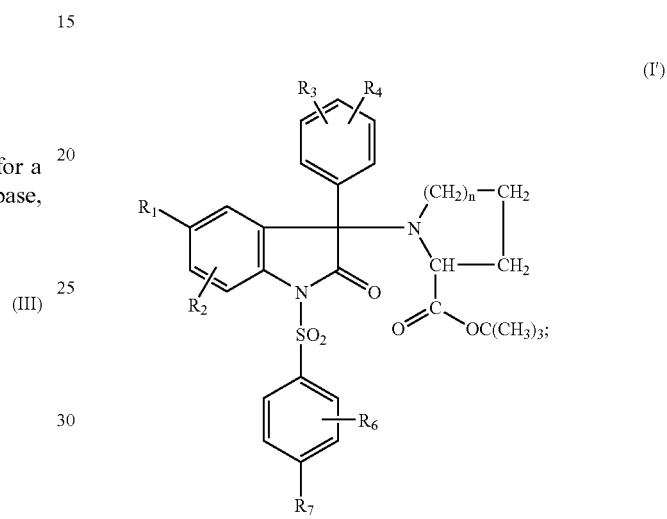

(I')

b) the compound of formula (I') is hydrolysed by the action of an acid to give a compound of formula:

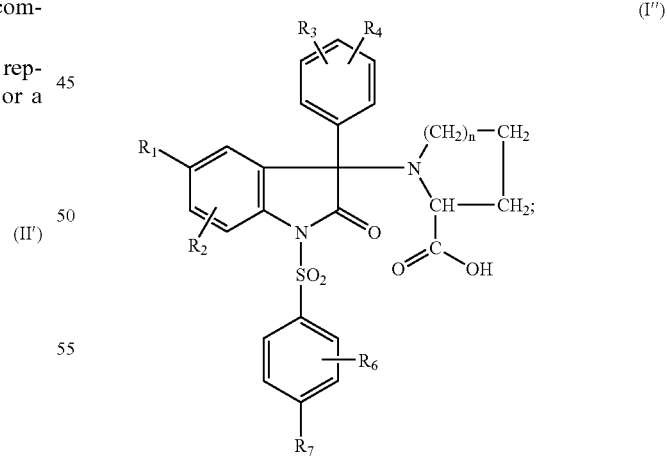

(I")

c) the compound of formula (I") is reacted with ethylamine, dimethylamine or azetidine.

In step a), the reaction between the compound of formula (II') and the halide of formula (III) is carried out as described above for the process according to the invention.

The compound of formula (I') thus obtained is hydrolysed in step b) with a strong acid such as hydrochloric acid in an inert solvent such as dioxane and at a temperature of between 0° C. and room temperature.

In step c), the reaction between the compound of formula (I") and ethylamine, dimethylamine or azetidine is carried out in the presence of a coupling agent used in peptide chemistry, such as benzotriazol-1-yloxytris(dimethylamino)phosphonium hexafluorophosphate or benzotriazol-1-yloxytripyrrolidino-phosphonium hexafluorophosphate in the presence of a base such as triethylamine or N,N-diisopropylethylamine, in an inert solvent such as dichloromethane, tetrahydrofuran or a mixture of these solvents, and at a temperature of between 0° C. and room temperature.

In particular, a compound of formula (I) in which $R_3$ represents hydroxyl is prepared by reacting a compound of formula (II) in which $R_3$ represents a benzyloxy group with a compound of formula (III) according to the process of the invention. The compound thus obtained is then deprotected according to the method described in Chem. Pharm. Bull., 1978, 26 (8), 2562-2564 to give the expected compound of formula (I).

The compounds of formula (I) thus obtained may be subsequently separated from the reaction medium and purified according to the conventional methods, for example by crystallization or chromatography.

The compounds of formula (II) or (II') are prepared by reacting a 3-halo-1,3-dihydro-2H-indol-2-one compound of formula:

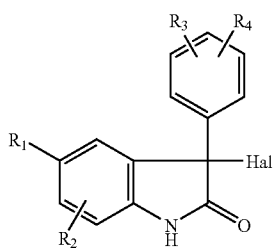

in which $R_1$, $R_2$, $R_3$ and $R_4$ are as defined for a compound of formula (I) and Hal represents a halogen atom, preferably chlorine or bromine, with a compound of formula:

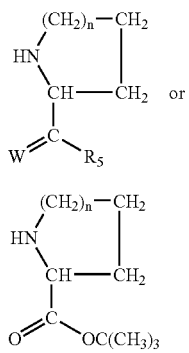

in which n, W and $R_5$ are as defined for a compound of formula (I). The reaction is carried out in the absence or presence of a base such as diisopropylethylamine or triethylamine, in an inert solvent such as dichloromethane, chloroform, tetrahydrofuran, methanol or a mixture of these solvents and at a temperature of between 0° C. and the reflux temperature of the solvent. In the absence of base, the reaction is carried out using an excess of the compound of formula (V) or (V').

The compounds of formula (III) are known or prepared by known methods such as those disclosed in EP-0 469 984 B and WO 95/18105. For example, the compounds of formula (III) may be prepared by halogenation of the corresponding benzenesulphonic acids or of their salts, for example of their sodium or potassium salts. The reaction is carried out in the presence of a halogenating agent such as phosphorus oxychloride, thionyl chloride, phosphorus trichloride, phosphorus tribromide or phosphorus pentachloride, without solvent or in an inert solvent such as a halogenated hydrocarbon or N,N-dimethylformamide and at a temperature of between −10° C. and 200° C.

2,4-Dimethoxybenzenesulphonyl chloride is prepared according to J. Am. Chem. Soc., 1952, 74, 2008. 3,4-Dimethoxybenzenesulphonyl chloride is commercially available, or is prepared according to J. Med. Chem., 1977, 20 (10), 1235-1239.

The compounds of formula (IV) are known and are prepared according to known methods such as those disclosed in WO 95/18105.

For example, a compound of formula:

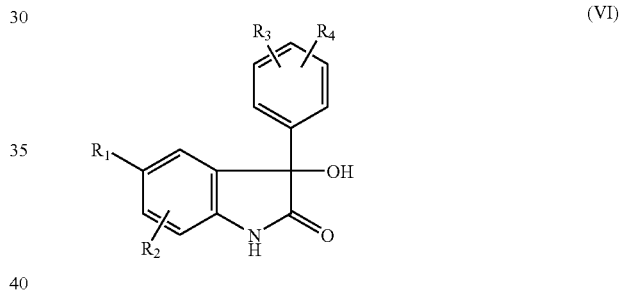

in which $R_1$, $R_2$, $R_3$ and $R_4$ are as defined for a compound of formula (I), is converted into a compound of formula (IV) in which Hal=Cl by the action of thionyl chloride in the presence of a base such as pyridine, in an inert solvent such as dichloromethane and at a temperature of between 0° C. and room temperature.

According to another example of the preparation of the compounds of formula (IV), a compound of formula:

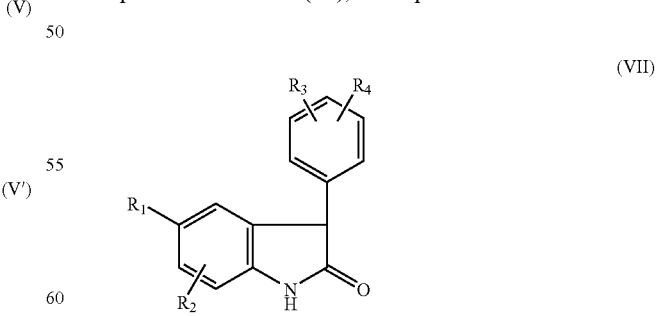

in which $R_1$, $R_2$, $R_3$ and $R_4$ are as defined for a compound of formula (I), is converted into a compound of formula (IV) in which Hal=Br, using a halogenating agent such as bromine according to the process described in Farm. Zh. (Kiev), 1976, 5, 30-33.

The compounds of formula (VI) are known and are prepared according to known methods such as those disclosed in WO 95/18105.

For example, a compound of formula (VI) is prepared by reacting a 1H-indole-2,3-dione derivative of formula:

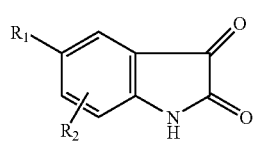

(VIII)

in which $R_1$ and $R_2$ are as defined for a compound of formula (I), with an organomagnesium derivative of formula:

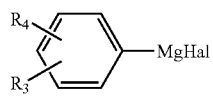

(IX)

in which $R_3$ and $R_4$ are as defined for a compound of formula (I) and Hal represents a halogen atom, preferably bromine or iodine, in an inert solvent such as tetrahydrofuran or diethyl ether and at a temperature of between 0° C. and the reflux temperature of the solvent.

A compound of formula (VI) in which $R_3$ is as defined for a compound of formula (I) and is in position -2- of the phenyl and $R_4$, which is other than hydrogen, is in position -3- or -6- of the phenyl, may also be prepared by reacting a compound of formula:

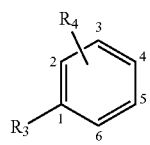

(XVI)

in which $R_3$ is as defined for a compound of formula (I) and $R_4$ is in position -2- or -5- of the phenyl, with a lithium derivative such as n-butyllithium, and the lithiated intermediate thus obtained is then reacted with a compound of formula (VIII). The reaction is carried out in a solvent such as diethyl ether, tetrahydrofuran, hexane or a mixture of these solvents, at a temperature of between −70° C. and room temperature.

The 1H-indole-2,3-dione derivatives (VIII) are commercially available or are prepared according to the methods described in Tetrahedron Letters, 1998, 39, 7679-7682; Tetrahedron Letters, 1994, 35, 7303-7306; J. Org. Chem., 1977, 42 (8), 1344-1348; J. Org. Chem., 1952, 17, 149-156; J. Am. Chem. Soc., 1946, 68, 2697-2703; Organic Syntheses, 1925, V, 71-74 and Advances in Heterocyclic Chemistry, A. R. Katritzky and A. J. Boulton, Academic Press, New York, 1975, 18, 2-58.

The organomagnesium derivatives (IX) are prepared according to the conventional methods that are well known to those skilled in the art.

A compound of formula (VI) may also be prepared by atmospheric oxidation of a compound of formula (VII) in the presence of a base such as sodium hydride and in the presence of dimethyl disulphide.

In particular, the compounds of formula (VI) in which $R_3$ is in position -2 of the phenyl and $R_3=(C_1-C_2)$alkoxy and $R_4$=H, or $R_3=R_4=(C_1-C_2)$alkoxy with $R_4$ in position -3 or -6 of the phenyl, $R_2$ is other than a halogen atom and $R_1$ is as defined for a compound of formula (I), may be prepared by following the process described in Scheme 1.

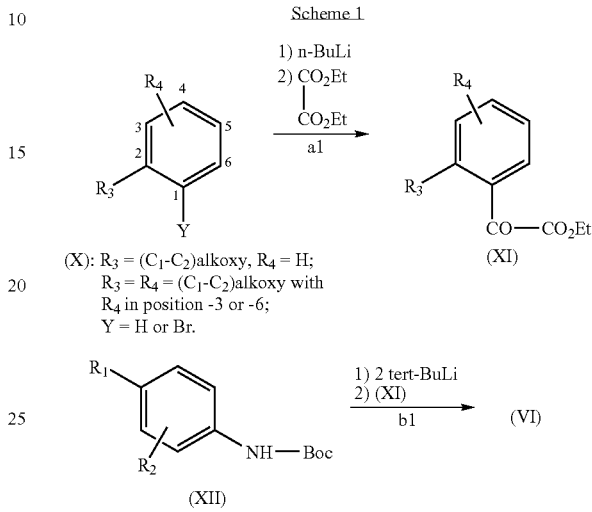

Scheme 1

(X): $R_3 = (C_1-C_2)$alkoxy, $R_4 = H$;
$R_3 = R_4 = (C_1-C_2)$alkoxy with $R_4$ in position -3 or -6;
Y = H or Br.

In step a1 of Scheme 1, a compound of formula (X) is first reacted with a lithium derivative such as n-butyllithium, in the absence or presence of a base such as N,N,N',N'-tetramethylethylenediamine, and the lithiated intermediate thus obtained is then reacted with diethyl oxalate to give the compound of formula (XI). The reaction is carried out in an inert solvent such as diethyl ether, tetrahydrofuran, hexane or a mixture of these solvents and at a temperature of between −70° C. and room temperature.

In step b1, a compound of formula (XII) is first reacted with two equivalents of a lithium derivative such as tert-butyllithium, and the lithiated derivative thus obtained is then reacted with the compound of formula (XI) to give the expected compound of formula (VI). The reaction is carried out in an inert solvent such as diethyl ether, tetrahydrofuran, pentane or a mixture of these solvents and at a temperature of between −70° C. and room temperature.

The compounds of formula (X) are commercially available or are synthesized conventionally.

The compounds of formula (XII) are prepared by reacting the corresponding aniline derivatives with di-tert-butyl dicarbonate according to the conventional methods.

The compounds of formula (VII) are known and are prepared according to known methods such as those disclosed in WO 95/18105 or in J. Org. Chem., 1968, 33, 1640-1643.

The compounds of formula (V) are known or are prepared according to known methods. Thus, for example, the compounds of formula (V) in which W represents an oxygen atom and $R_5$ represents an ethylamino or dimethylamino group or a 1-azetidinyl radical are prepared according to Scheme 2 below in which Pr represents an N-protecting group, in particular tert-butoxycarbonyl or 9-fluorenylmethoxycarbonyl and n is as defined for a compound of formula (I).

Scheme 2

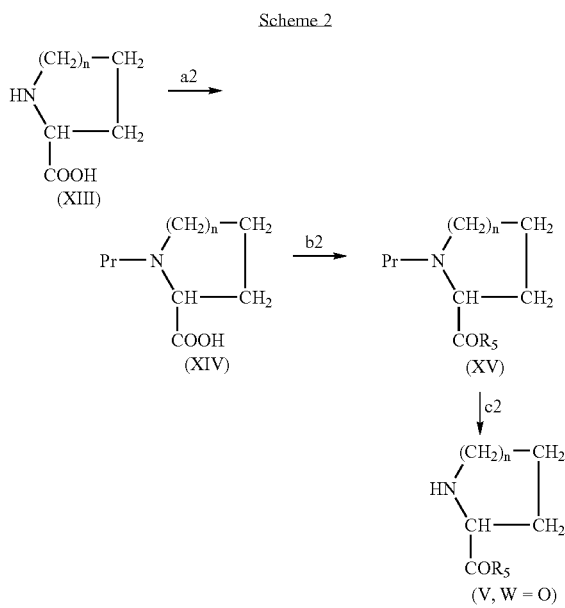

In step a2 of Scheme 2, the nitrogen atom of the compound of formula (XIII) is protected according to the conventional methods to give a compound of formula (XIV). Some of the compounds of formula (XIV) are commercially available.

The acid (XIV) is reacted in step b2 with ethylamine, dimethylamine or azetidine according to the conventional methods of peptide coupling to give the compound of formula (XV), which is deprotected in step c2, according to the known methods, to give the expected compound of formula (V). In particular, when Pr represents a 9-fluorenylmethoxycarbonyl group, the deprotection is carried out using the method described in Synthetic Communications, 1994, 24 (2), 187-195.

The compounds of formula (V) in which $R_5$ represents a $(C_1-C_2)$alkoxy or the compounds of formula (V') are known or are prepared according to known methods such as, for example, by esterification reaction starting with the acids of formula (XIII).

The acids of formula (XIII) are commercially available.

The compounds of formula (V) in which W represents a sulphur atom are prepared from the corresponding compounds of formula (V) in which W represents an oxygen atom, N-protected on the nitrogen atom, using the methods described in J. Med. Chem., 1989, 2178-2199, in particular by reaction with Lawesson's reagent (2,4-bis(4-methoxyphenyl)-1,3-dithia-2,4-diphosphetane 2,4-disulphide or with phosphorus pentasulphide. After a step of deprotection of the nitrogen atom, the expected compound of formula (V) is obtained.

When it is desired to prepare an optically pure compound of formula (I), an optically pure compound of formula (II) or (II') is preferably reacted according to the process of the invention or the variant of the process.

The optically pure compounds of formula (II) or (II') are prepared by reacting the racemic compound of formula (IV) with an optically pure compound of formula (V) or (V'), followed by separation of the mixture of diastereoisomers according to the conventional methods, for example by crystallization or chromatography.

Alternatively, the mixture of diastereoisomers of the compound of formula (II) or (II') may be reacted and the mixture of diastereoisomers of the compound of formula (I) thus obtained may be separated.

During any one of the steps for preparing the compounds of formula (I) or the intermediate compounds of formula (II), (II'), (IV), (V), (V') or (VI), it may be necessary and/or desirable to protect the reactive or sensitive functional groups, such as the amine, hydroxyl or carboxyl groups, present on any one of the molecules concerned. This protection may be carried out using the conventional protecting groups, such as those described in Protective Groups in Organic Chemistry, J. F. W. McOmie, Ed. Plenum Press, 1973, in Protective Groups in Organic Synthesis, T. W. Greene and P. G. M. Wutts, Ed. John Wiley and Sons, 1991 or in Protecting Groups, Kocienski P. J., 1994, Georg Thieme Verlag. The protecting groups may be removed by a suitable subsequent step using the methods known to those skilled in the art which do not affect the rest of the molecule concerned.

The N-protecting groups which may be used are the conventional N-protecting groups that are well known to those skilled in the art, such as, for example, the tert-butoxycarbonyl, fluorenylmethoxycarbonyl, benzyl, benzhydrylidene or benzyloxycarbonyl group.

The compounds of formula (II) are novel and form part of the invention.

Thus, according to another of its aspects, a subject of the invention is compounds of formula:

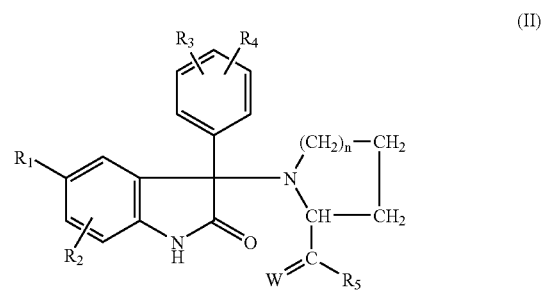

in which:
n is 1 or 2;
W represents an oxygen atom or a sulphur atom;
$R_1$ represents a halogen atom; a $(C_1-C_4)$alkyl; a $(C_1-C_4)$alkoxy; a trifluoromethyl radical; a trifluoromethoxy radical;
$R_2$ represents a hydrogen atom; a halogen atom; a $(C_1-C_4)$alkyl; a $(C_1-C_4)$alkoxy; a trifluoromethyl radical;
or $R_2$ is in position -6- of the indol-2-one ring and $R_1$ and $R_2$ together represent a divalent trimethylene radical;
$R_3$ represents a halogen atom; a hydroxyl; a $(C_1-C_2)$alkyl; a $(C_1-C_2)$alkoxy; a trifluoromethoxy radical;
$R_4$ represents a hydrogen atom; a halogen atom; a $(C_1-C_2)$alkyl; a $(C_1-C_2)$alkoxy;
or $R_3$ is in position -2- of the phenyl, $R_4$ is in position -3- of the phenyl and $R_3$ and $R_4$ together represent a methylenedioxy radical;
$R_5$ represents an ethylamino group; a dimethylamino group; a 1-azetidinyl radical; a $(C_1-C_2)$alkoxy;

as well as the salts thereof with mineral or organic acids, in the form of optically pure isomers or in the form of a mixture of diastereoisomers or in the form of a racemic mixture.

The salts of the compounds of formula (II) comprise those with mineral or organic acids which allow a suitable separation or crystallization of the compounds of formula (II) such as the hydrochloride, the hydrobromide, the oxalate, the maleate, the succinate, the fumarate, the citrate or the acetate.

The above compounds of formula (I) also comprise those in which one or more hydrogen or carbon atoms have been replaced with their radioactive isotope, for example tritium, or carbon-14. Such labelled compounds are useful in research, metabolism or pharmacokinetics studies and in biochemical assays as receptor ligands.

The compounds according to the invention have undergone biochemical studies.

The affinity of the compounds of formula (I) according to the invention for arginine-vasopressin $V_{1b}$ receptors was determined in vitro using the method described by Y. De Keyser et al., FEBS Letters, 1994, 356, 215-220. This method consists in studying in vitro the displacement of tritiated arginine-vasopressin ($[^3H]$-AVP) at the $V_{1b}$ receptors present on adenohypophysal membrane or cell preparations carrying rat or human $V_{1b}$ receptors. The 50% inhibitory concentrations ($IC_{50}$) for the attachment of tritiated arginine-vasopressin of the compounds according to the invention are low and vary from $10^{-7}$ to $10^{-9}$ M.

The affinity of the compounds of formula (I) according to the invention for arginine-vasopressin $V_{1a}$ receptors was determined in vitro using the method described by M. Thibonnier et al., J. Biol. Chem., 1994, 269, 3304-3310. This method consists in studying in vitro the displacement of tritiated arginine-vasopressin ($[^3H]$-AVP) at the $V_{1a}$ receptors present on membrane or cell preparations carrying rat or human $V_{1a}$ receptors. Some of the compounds of formula (I) also exhibit an affinity for arginine-vasopressin $V_{1a}$ receptors, with $IC_{50}$ values which vary from $10^{-7}$ to $10^{-9}$ M.

The affinity of the compounds of formula (I) according to the invention for vasopressin $V_2$ receptors has also been studied (method described by M. Birnbaumer et al., Nature (Lond.), 1992, 357, 333-335). The compounds studied have little or no affinity for the $V_2$ receptors, with $IC_{50}$ values which are generally greater than $10^{-6}$ M.

The compounds of the present invention are in particular active principles of pharmaceutical compositions, the toxicity of which is compatible with their use as medicaments.

According to another of its aspects, the present invention relates to the use of the compounds of formula (I), of their solvates and/or of their hydrates which are pharmaceutically acceptable for the preparation of medicaments intended for the treatment of any pathology where arginine-vasopressin and/or its $V_{1b}$ receptors or both its $V_{1b}$ receptors and its $V_{1a}$ receptors are implicated.

According to another of its aspects, the present invention relates to the use of the compounds of formula (I), of their solvates and/or of their hydrates which are pharmaceutically acceptable for the preparation of medicaments intended for the treatment of pathologies of the cardiovascular system, of the central nervous system, of the renal system or of the gastric system and of small-cell lung cancers, obesity, type II diabetes, insulin resistance, hypertriglyceridaemia, atherosclerosis, Cushing's syndrome or any pathology resulting from stress and chronic stress conditions.

Thus, the compounds according to the invention may be used, in man or in animals, in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischaemia or haemostasis disturbances; conditions of the central nervous system, such as migraine, cerebral vasospasm, cerebral haemorrhage, cerebral oedema, depression, anxiety, stress, obsessive-compulsive disorder, panic attacks, psychotic states or memory disorders, for example; conditions of the renal system, such as renal vasospasm, necrosis of the renal cortex or nephrogenic diabetes insipidus; conditions of the gastric system, such as gastric vasospasm, cirrhosis of the liver, ulcers or the pathology of vomiting, for example nausea, including nausea due to chemotherapy or travel sickness; or diabetic nephropathy. The compounds according to the invention can also be used in the treatment of disorders of sexual behaviour; in women, the compounds according to the invention can be used to treat dysmenorrhoea or premature labour. The compounds according to the invention can also be used in the treatment of small-cell lung cancers; hyponatremic encephalopathy; pulmonary syndrome; Ménière's disease; glaucoma; cataracts; obesity; type II diabetes; atherosclerosis; Cushing's syndrome; insulin resistance; or hypertriglyceridaemia; or in post-operative treatments, in particular after abdominal surgery.

The compounds according to the invention can also be used in the treatment or prevention of any pathology resulting from stress, such as fatigue and its syndromes, ACTH-dependent disorders, cardiac disorders, pain, modifications in gastric emptying, in faecal excretion (colitis, irritable bowel syndrome or Crohn's disease) or in acid secretion, hyperglycaemia, immunosuppression, inflammatory processes (rheumatoid arthritis and osteoarthritis), multiple infections, cancers, asthma, psoriasis, allergies and various neuropsychiatric disorders, such as anorexia nervosa, bulimia, mood disorders, depression, anxiety, sleep disorders, panic states, phobias, obsession, disorders of pain perception (fibromyalgia), neurodegenerative diseases (Alzheimer's disease, Parkinson's disease or Huntington's disease), substance dependence, haemorrhagic stress, muscle spasms or hypoglycaemia. The compounds according to the invention can also be used in the treatment or prevention of chronic stress conditions, such as immunodepression, fertility disorders or dysfunctionings of the hypothalamo-pituitary-adrenal axis.

The compounds according to the invention can also be used as psychostimulants, resulting in an increase in alertness or emotional reactivity to the surroundings and making adaptation easier.

The above compounds of formula (I), their solvates and/or their hydrates which are pharmaceutically acceptable can be used at daily doses of 0.01 to 100 mg per kilo of body weight of the mammal to be treated, preferably at daily doses of 0.1 to 50 mg/kg. In man, the dose can preferably vary from 0.1 to 4 000 mg per day, more particularly from 0.5 to 1 000 mg, depending upon the age of the subject to be treated or the type of treatment: prophylactic or curative.

For their use as medicaments, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions including, as active principle, a compound of formula (I), one of its solvates and/or one of its hydrates which are pharmaceutically acceptable.

In the pharmaceutical compositions of the present invention for administration by the oral, sublingual, inhaled, subcutaneous, intramuscular, intravenous, transdermal, local or rectal route, the active principles can be administered in single-dose administration forms, as a mixture with conventional pharmaceutical vehicles, to animals and human beings. The appropriate single-dose administration forms comprise forms by the oral route, such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gelatin capsules, a mixture of pharmaceutical excipients is added to the micronized or nonmicronized active principle, which mixture can be composed of diluents, such as, for example, lactose, microcrystalline cellulose, starch or dicalcium phosphate, of binders, such as, for example, polyvinylpyrrolidone or hydroxypropylmethylcellulose, of disintegrating agents, such as crosslinked polyvinylpyrrolidone or crosslinked carboxymethylcellulose, of flow agents, such as silica or talc, or of lubricants, such as magnesium stearate, stearic acid, glyceryl tribehenate or sodium stearylfumarate.

Wetting agents or surfactants, such as sodium lauryl sulphate, polysorbate 80 or poloxamer 188, can be added to the formulation.

The tablets can be prepared by various techniques: direct tabletting, dry granulation, wet granulation or hot-melt.

The tablets can be bare or sugar-coated (with sucrose, for example) or coated with various polymers or other appropriate materials.

The tablets can have a flash, delayed or sustained release by preparing polymeric matrices or by using specific polymers when forming the thin film.

The gelatin capsules may be soft or hard and may or may not be coated with a thin film, so as to have a flash, sustained or delayed activity (for example via an enteric form).

They can comprise not only a solid formulation formulated as above for tablets but also liquids or semi-solids.

A preparation in the form of a syrup or elixir can comprise the active principle in conjunction with a sweetener, preferably a calorie-free sweetener, methylparaben and propylparaben, as antiseptic, a flavouring agent and an appropriate colorant.

The water-dispersible powders or granules can comprise the active principle as a mixture with dispersing agents, wetting agents or suspending agents, such as polyvinylpyrrolidone, as well as with sweeteners or flavour enhancers.

For rectal administration, recourse is had to suppositories which are prepared with binders which melt at the rectal temperature, for example cocoa butter or polyethylene glycols.

For parenteral, intranasal or intraocular administration, use is made of aqueous suspensions, isotonic saline solutions or sterile and injectable solutions which comprise pharmacologically compatible dispersing agents and/or solubilizing agents, for example propylene glycol.

Thus, to prepare an aqueous solution which can be injected by the intravenous route, use may be made of a cosolvent, such as, for example, an alcohol, such as ethanol, or a glycol, such as polyethylene glycol or propylene glycol, and of a hydrophilic surfactant, such as polysorbate 80 or poloxamer 188. To prepare an oily solution which can be injected by the intramuscular route, the active principle can be dissolved with a triglyceride or a glyceryl ester.

For local administration, use may be made of creams, ointments, gels, eyewashes or sprays.

For transdermal administration, use may be made of patches in multilaminar or reservoir form, in which the active principle can be in alcoholic solution, or sprays.

For administration by inhalation, use is made of an aerosol comprising, for example, sorbitan trioleate or oleic acid and trichlorofluoromethane, dichlorofluoromethane, dichlorotetrafluoroethane, freon substitutes or any other biologically compatible propellant gas; use may also be made of a system comprising the active principle, alone or in combination with an excipient, in powder form.

The active principle can also be presented in the form of a complex with a cyclodextrin, for example $\alpha$-, $\beta$- or $\gamma$-cyclodextrin or 2-hydroxypropyl-$\beta$-cyclodextrin.

The active principle can also be formulated in the form of microcapsules or microspheres, optionally with one or more vehicles or additives.

Use may be made of implants among the sustained-release forms of use in the case of chronic treatments. These implants can be prepared in the form of an oily suspension or in the form of a suspension of microspheres in an isotonic medium.

The active principle of formula (I) is present in each dosage unit in the amounts suited to the daily doses envisaged. In general, each dosage unit is suitably adjusted according to the dosage and the type of administration provided, for example tablets, gelatin capsules and the like, sachets, blisters, syrups and the like, or drops, so that such a dosage unit comprises from 0.1 to 1 000 mg of active principle, preferably from 0.5 to 250 mg, which has to be administered one to four times daily.

Although these dosages are examples of average situations, there may be specific cases where higher or lower dosages are appropriate; such dosages also form part of the invention. According to the usual practice, the dosage appropriate to each patient is determined by the physician according to the method of administration and the age, the weight and the response of the said patient.

The compositions of the present invention can comprise, in addition to the compounds of formula (I), their solvates and/or their hydrates which are pharmaceutically acceptable, other active principles which can be of use in the treatment of the disorders or diseases indicated above.

Thus, another subject-matter of the present invention is pharmaceutical compositions comprising several active principles in combination, one of which is a compound according to the invention.

Thus, according to the present invention, pharmaceutical compositions can be prepared which comprise a compound according to the invention in combination with a compound which has an effect on the CRF receptors.

The compounds according to the invention can also be used for the preparation of compounds for veterinary use.

The following PREPARATIONS and EXAMPLES illustrate the invention without, however, limiting it.

Use is made, in the Preparations and in the Examples, of the following abbreviations:
ether: diethyl ether
iso ether: diisopropyl ether
DMF: N,N-dimethylformamide
THF: tetrahydrofuran
DCM: dichloromethane
EtOAc: ethyl acetate
TMEDA: N,N,N',N'-tetramethylethylenediamine
DIPEA: diisopropylethylamine
TFA: trifluoroacetic acid
Boc: tert-butoxycarbonyl Cbz: benzyloxycarbonyl Bzl: benzyl BOP: benzotriazol-1-yloxytris(dimethylamino)phosphonium hexafluorophosphate PyBOP: benzotriazol-1-yloxytripyrrolidino-phosphonium hexafluorophosphate DCC: 1,3-dicyclohexylcarbodiimide HOBT: 1-hydroxybenzotriazole hydrate Ethyl ether: saturated solution of hydrogen chloride in diethyl ether M.p.: melting point RT: room temperature B.p.: boiling point HPLC: high performance liquid chromatography.

The proton magnetic resonance spectra ($^1$H NMR) are recorded at 200 MHz in $d_6$-DMSO using the $d_6$-DMSO peak as reference. The chemical shifts δ are expressed in parts per million (ppm). The signals observed are expressed thus: s: singlet; bs: broad singlet; d: doublet; dd: doubled doublet; t: triplet; dt: doubled triplet; q: quartet; up: unresolved peak; mt: multiplet.

PREPARATIONS

Preparations of the compounds of formula (IV).

Preparation 1.1

3,5-Dichloro-3-(2-methoxyphenyl)-1,3-dihydro-2H-indol-2-one (IV): $R_1$=Cl; $R_2$=H; $R_3$=2-OCH$_3$; $R_4$=H; Hal=Cl A) 5-Chloro-3-hydroxy-3-(2-methoxyphenyl)-1,3-dihydro-2H-indol-2-one This compound is prepared according to the procedure disclosed in WO 95/18105. A solution of 2-methoxyphenylmagnesium bromide is prepared from 16 g of magnesium in 35 ml of ether and from a solution of 124 g of 1-bromo-2-methoxybenzene in 175 ml of ether. This solution is added dropwise under an argon atmosphere to a mixture, cooled beforehand in an ice bath, of 30 g of 5-chloro-1H-indole-2,3-dione in 250 ml of THF and then the mixture is left stirring while allowing the temperature to rise to RT. After stirring for 1 hour at RT, the reaction mixture is slowly poured into saturated NH$_4$Cl solution and the THF is evaporated off under vacuum. The precipitate formed is spin-filtered off and is washed with iso ether. 42 g of the expected product are obtained, which product is used without further purification in the following stage.

B) 3,5-Dichloro-3-(2-methoxyphenyl)-1,3-dihydro-2H-indol-2-one

This compound is prepared according to the procedure disclosed in WO 95/18105. A mixture of 9 g of the compound obtained in the preceding stage and 3.74 ml of pyridine in 100 ml of DCM is cooled to 0° C., a solution of 3.45 ml of thionyl chloride in 3 ml of DCM is added dropwise over 3 minutes, and the mixture is left stirring for 30 minutes. Water is added to the reaction mixture and the DCM is evaporated off under vacuum at RT. The precipitate formed is spin-filtered off, washed four times with water and then with cold iso ether, and dried. 8.8 g of the expected product are obtained.

Preparation 1.2

3,5-Dichloro-3-(2-ethoxyphenyl)-1,3-dihydro-2H-indol-2-one (IV): $R_1$=Cl; $R_2$=H; $R_3$=2-OCH$_2$CH$_3$; $R_4$=H; Hal=Cl A) 1-Bromo-2-ethoxybenzene A mixture of 17.5 g of 2-bromophenol, 66 ml of diethyl sulphate and 170 ml of 10% NaOH solution is refluxed for 2 hours. After cooling the reaction mixture to RT, it is extracted with EtOAc, the organic phase is washed with 2N NaOH solution and dried over Na$_2$SO$_4$, and the solvent is evaporated off under vacuum. 19.6 g of the expected product are obtained.

B) 5-Chloro-3-(2-ethoxyphenyl)-3-hydroxy-1,3-dihydro-2H-indol-2-one

A solution of 2-ethoxyphenylmagnesium bromide is prepared from 2.2 g of magnesium in 10 ml of ether and from a solution of 16.5 g of the compound obtained in the preceding step in 40 ml of ether. This solution is added dropwise, under a nitrogen atmosphere, to a mixture of 5 g of 5-chloro-1H-indole-2,3-dione in 20 ml of THF, while keeping the temperature of the reaction medium below 35° C. After stirring for 2 hours at RT, the reaction mixture is poured into 200 ml of 2N HCl and extracted with EtOAc, the organic phase is dried over Na$_2$SO$_4$ and the solvents are evaporated off under vacuum. The residue is taken up in hot iso ether and left to recrystallize. The crystalline product formed is spin-filtered off, washed with iso ether and dried. 5.7 g of the expected product are obtained;

m.p.=251° C.

C) 3,5-Dichloro-3-(2-ethoxyphenyl)-1,3-dihydro-2H-indol-2-one 1 ml of thionyl chloride is added at RT to a mixture of 3 g of the compound obtained in the preceding step and 2 ml of pyridine in 50 ml of DCM, and the mixture is left stirring for 1 hour at RT. The reaction mixture is chromatographed on silica gel, eluting with DCM. 2.4 g of the expected product are obtained after crystallization from iso ether;

m.p.=198° C.

Preparation 1.3

3,5-Dichloro-3-(3-methoxyphenyl)-1,3-dihydro-2H-indol-2-one (IV): $R_1$=Cl; $R_2$=H; $R_3$=3-OCH$_3$; $R_4$=H; Hal=Cl A) 5-Chloro-3-hydroxy-3-(3-methoxyphenyl)-1,3-dihydro-2H-indol-2-one A solution of 3-methoxyphenylmagnesium bromide is prepared from 3.5 g of magnesium in 10 ml of THF and from a solution of 25 g of 1-bromo-3-methoxy-benzene in 40 ml of THF. This solution is added dropwise, under a nitrogen atmosphere, to a mixture of 8 g of 5-chloro-1H-indole-2,3-dione in 50 ml of THF, while keeping the temperature of the reaction medium below 40° C., followed by refluxing for 1 hour. The reaction mixture is cooled to RT, poured into saturated NH$_4$Cl solution and extracted with EtOAc, the organic phase is washed with water and dried over Na$_2$SO$_4$, and the solvent is evaporated off under vacuum. 9.1 g of the expected product are obtained after crystallization from hot iso ether;

m.p.=212° C.

B) 3,5-Dichloro-3-(3-methoxyphenyl)-1,3-dihydro-2H-indol-2-one

A mixture of 5 g of the compound obtained in the preceding step and 2 ml of pyridine in 20 ml of DCM is cooled to a temperature below 10° C., a solution of 1.65 ml of thionyl chloride in 10 ml of DCM is added dropwise and the mixture is left stirring for 30 minutes at RT. The reaction mixture is washed twice with water, the organic phase is dried over $Na_2SO_4$ and the solvent is evaporated off under vacuum. The residue is chromatographed on silica gel, eluting with DCM. 3.1 g of the expected product are obtained;

m.p.=170° C.

Preparation 1.4

3,5-Dichloro-3-(4-methoxyphenyl)-1,3-dihydro-2H-indol-2-one (IV): $R_1$=Cl; $R_2$=H; $R_3$=4-$OCH_3$; $R_4$=H; Hal=Cl A) 5-Chloro-3-hydroxy-3-(4-methoxyphenyl)-1,3-dihydro-2H-indol-2-one This compound is prepared according to the procedure described in step A of Preparation 1.3 starting with 3.5 g of magnesium, 25 g of 1-bromo-4-methoxybenzene, 50 ml of THF and a mixture of 8 g of 5-chloro-1H-indol-2,3-dione in 50 ml of THF. 9.3 g of the expected product are obtained after crystallization from hot iso ether; m.p.=202° C.

B) 3,5-Dichloro-3-(4-methoxyphenyl)-1,3-dihydro-2H-indol-2-one 0.9 ml of thionyl chloride is added to a mixture of 2.5 g of the compound obtained in the preceding step and 1 ml of pyridine in 30 ml of DCM at a temperature below 20° C., and the mixture is left stirring for 15 minutes. The reaction mixture is washed twice with water and dried over $Na_2SO_4$, and this solution is used without further purification in Preparations 3.9 and 3.10.

Preparation 1.5

3,5-Dichloro-3-(2,3-dimethoxyphenyl)-1,3-dihydro-2H-indol-2-one (IV): $R_1$=Cl; $R_2$=H; $R_3$=2-$OCH_3$; $R_4$=3-$OCH_3$; Hal=Cl A) Ethyl 2-(2,3-dimethoxyphenyl)-2-oxoacetate A mixture of 27.6 g of 1,2-dimethoxybenzene in 160 ml of ether is cooled to −40° C., 250 ml of a 1.6 M solution of n-butyllithium in hexane are added dropwise and the mixture is then left stirring for 24 hours while allowing the temperature to return to RT. The reaction mixture is cooled to −20° C., 136 ml of diethyl oxalate are added rapidly and the mixture is left stirring while allowing the temperature to return to RT. After stirring for 30 minutes at RT, the reaction mixture is poured into saturated $NH_4Cl$ solution, the phases are separated after settling has taken place, the aqueous phase is extracted with ether, the combined organic phases are washed twice with water and dried over $Na_2SO_4$, and the solvents are evaporated off under vacuum. The excess diethyl oxalate is removed by distillation under vacuum (b.p.=90° C. at 2 400 Pa). The resulting crude product is chromatographed on silica gel, eluting with a heptane/iso ether mixture (90/10; v/v). 25 g of the expected product are obtained and are used without further purification in the following step.

B) 5-Chloro-3-hydroxy-3-(2,3-dimethoxyphenyl)-1,3-dihydro-2H-indol-2-one a) tert-Butyl 4-chlorophenylcarbamate A mixture of 12.7 g of 4-chloroaniline and 22 g of di-tert-butyl dicarbonate in 60 ml of dioxane is left stirring for 24 hours at RT. The reaction mixture is concentrated under vacuum, the residue is taken up in pentane and the precipitate formed is spin-filtered off and dried. 22.5 g of the expected product are obtained.

b) A mixture of 11.4 g of tert-butyl 4-chlorophenylcarbamate in 100 ml of ether is cooled to −40° C. under an atmosphere of dry nitrogen, 80 ml of a 1.5 M solution of tert-butyllithium in pentane are added dropwise and the mixture is left stirring at −20° C. for 3 hours. The reaction mixture is cooled to −40° C., a solution of 14 g of the compound obtained in step A in 50 ml of THF is added over 1 hour and the mixture is left stirring for 4 days at RT. The reaction mixture is poured into saturated $NH_4Cl$ solution and the precipitate formed is spin-filtered off and dried. 10.2 g of the expected product are obtained and are used without further purification in the following step.

C) 3,5-Dichloro-3-(2,3-dimethoxyphenyl)-1,3-dihydro-2H-indol-2-one 0.8 ml of pyridine is added, at RT, to a mixture of 2 g of the compound obtained in step B in 50 ml of DCM, followed by addition of 1.2 ml of thionyl chloride, and the mixture is left stirring until dissolved. The reaction mixture is washed with 1N HCl solution and then twice with water and dried over $Na_2SO_4$, and the solvent is evaporated off under vacuum. The residue is chromatographed on silica gel, eluting with a DCM/EtOAc mixture (95/5; v/v). 1.2 g of the expected product are obtained and are used without further purification.

Preparation 1.6

3,5-Dichloro-3-(2,4-dimethoxyphenyl)-1,3-dihydro-2H-indol-2-one (IV): $R_1$=Cl; $R_2$=H; $R_3$=2-$OCH_3$; $R_4$=4-$OCH_3$; Hal=Cl A) 5-Chloro-3-hydroxy-3-(2,4-dimethoxyphenyl)-1,3-dihydro-2H-indol-2-one A solution of 2,4-dimethoxyphenylmagnesium bromide is prepared starting with 2.2 g of magnesium in 10 ml of THF and a solution of 18 g of 1-bromo-2,4-dimethoxybenzene in 40 ml of THF. This solution is added dropwise to a mixture of 5 g of 5-chloro-1H-indole-2,3-dione in 50 ml of THF at a temperature of 30° C., followed by refluxing for 2 hours. The reaction mixture is cooled to RT, poured into saturated $NH_4Cl$ solution and extracted with EtOAc, the organic phase is washed with water and dried over $Na_2SO_4$, and the solvent is evaporated off under vacuum. 7.2 g of the expected product are obtained after crystallization from hot iso ether.

B) 3,5-Dichloro-3-(2,4-dimethoxyphenyl)-1,3-dihydro-2H-indol-2-one

A mixture of 1.5 g of the compound obtained in the preceding step and 0.4 ml of pyridine in 20 ml of DCM is cooled to a temperature below 10° C., 0.45 ml of thionyl chloride is added dropwise and the mixture is left stirring for 15 minutes. The reaction mixture is washed twice with water and dried over $Na_2SO_4$, and this solution is used without further purification in Preparations 3.13 and 3.14.

Preparation 1.7

3,5-Dichloro-3-(2,5-dimethoxyphenyl)-1,3-dihydro-2H-indol-2-one (IV): $R_1$=Cl; $R_2$=H; $R_3$=2-$OCH_3$; $R_4$=5-$OCH_3$; Hal=Cl.

A) 5-Chloro-3-hydroxy-3-(2,5-dimethoxyphenyl)-1,3-dihydro-2H-indol-2-one

A solution of 2,5-dimethoxyphenylmagnesium bromide is prepared starting with 2.2 g of magnesium, 18 g of 1-bromo-2,5-dimethoxybenzene and 50 ml of ether. This solution is added dropwise to a mixture of 5 g of 5-chloro-1H-indole-2,3-dione in 50 ml of THF at a temperature below 30° C., and is then refluxed for 3 hours. After cooling to RT, the reaction mixture is poured into 1N HCl solution and extracted with EtOAc, the organic phase is washed with water and dried over $Na_2SO_4$, and the solvent is evaporated off under vacuum. 7.1 g of the expected product are obtained after crystallization from hot iso ether.

B) 3,5-Dichloro-3-(2,5-diemthoxyphenyl)-1,3-dihydro-2H-indol-2-one

A mixture of 3 g of the compound obtained in the preceding step and 1.2 ml of pyridine in 50 ml of DCM is cooled to a temperature below 20° C., 0.8 ml of thionyl chloride is added and the mixture is left stirring for 1 hour. The reaction mixture is washed with water, the organic phase is dried over $Na_2SO_4$ and the solvent is evaporated off under vacuum. The residue is chromatographed on silica gel, eluting with DCM. 1.9 g of the expected product are obtained and are used without further purification.

Preparation 1.8

3,5-Dichloro-3-(2,6-dimethoxyphenyl)-1,3-dihydro-2H-indol-2-one (IV): $R_1$=Cl; $R_2$=H; $R_3$=2-$OCH_3$; $R_4$=6-$OCH_3$; Hal=Cl A) Ethyl 2-(2,6-dimethoxyphenyl)-2-oxoacetate A mixture of 28 g of 1,3-dimethoxybenzene and 24.3 g of TMEDA in 400 ml of hexane is cooled to a temperature below 10° C., 132 ml of a 1.6 M solution of n-butyllithium in hexane are added dropwise and the mixture is left stirring for 30 minutes. The reaction mixture is cooled to 0° C., 140 ml of diethyl oxalate are added over 15 minutes and the mixture is left stirring for 1 hour at RT. The reaction mixture is poured into a mixture of concentrated HCl solution and ice and is extracted with EtOAc, the organic phase is washed with water and dried over $Na_2SO_4$, and the solvent is evaporated off under vacuum. The excess diethyl oxalate is removed by distillation under vacuum (b.p.=90° C. at 2 400 Pa). The resulting crude product is chromatographed on silica gel, eluting with heptane and then with DCM. 34.5 g of the expected product are obtained.

B) 5-Chloro-3-hydroxy-3-(2,6-dimethoxyphenyl)-1,3-dihydro-2H-indol-2-one

A mixture of 28.5 g of tert-butyl 4-chlorophenylcarbamate (obtained in step Ba) of Preparation 1.5) in 300 ml of ether is cooled to −40° C., 191 ml of a 1.5 M solution of tert-butyllithium in pentane are added dropwise and the mixture is left stirring for 3 hours at −20° C. The reaction mixture is cooled to −60° C., a solution of 34.5 g of the compound obtained in the preceding step in 50 ml of THF is added dropwise and the mixture is left stirring for 48 hours at RT. The reaction mixture is poured into saturated $NH_4Cl$ solution and extracted with EtOAc, the organic phase is washed with water and dried over $Na_2SO_4$, and the solvent is evaporated off under vacuum. The residue is chromatographed on silica gel, eluting with DCM and then with a DCM/MeOH mixture (99/1; v/v). 8.7 g of the expected product are obtained after crystallization from iso ether; m.p.=182° C.

C) 3,5-Dichloro-3-(2,6-dimethoxyphenyl)-1,3-dihydro-2H-indol-2-one 1 ml of thionyl chloride is added to a mixture of 4 g of the compound obtained in the preceding step and 1.8 ml of pyridine in 250 ml of DCM, and the mixture is left stirring for 30 minutes at RT. The reaction mixture is washed with water, the organic phase is dried over $Na_2SO_4$ and the solvent is evaporated off under vacuum. 1.8 g of the expected product are obtained after crystallization from iso ether.

Preparation 1.9

3,5-Dichloro-3-(3,5-dimethoxyphenyl)-1,3-dihydro-2H-indol-2-one (IV): $R_1$=Cl; $R_2$=H; $R_3$=3-$OCH_3$; $R_4$=5-$OCH_3$; Hal=Cl A) 5-Chloro-3-hydroxy-3-(3,5-dimethoxyphenyl)-1,3-dihydro-2H-indol-2-one This compound is prepared according to the procedure described in step A of Preparation 1.6, starting with 1.2 g of magnesium, 9.5 g of 1-bromo-3,5-dimethoxybenzene, 50 ml of THF and a solution of 3 g of 5-chloro-1H-indole-2,3-dione in 50 ml of THF. 3.2 g of the expected product are obtained after crystallization from iso ether; m.p.=191° C.

B) 3,5-Dichloro-3-(3,5-dimethoxyphenyl)-1,3-dihydro-2H-indol-2-one

A mixture of 3.2 g of the compound obtained in the preceding step and 0.7 ml of pyridine in 100 ml of DCM is cooled to a temperature below 20° C., 0.7 ml of thionyl chloride is added and the mixture is left stirring for 15 minutes. The reaction mixture is washed with water, the organic phase is dried over $Na_2SO_4$ and the solvent is evaporated off under vacuum. 1.4 g of the expected product are obtained after crystallization from iso ether; m.p.=157° C.

Preparation 1.10

3,5-Dichloro-3-(1,3-benzodioxol-4-yl)-1,3-dihydro-2H-indol-2-one (IV): $R_1$=Cl; $R_2$=H; $R_3$+$R_4$=2,3-O—$CH_2$O—; Hal=Cl A) 4-Bromo-1,3-benzodioxole This compound is prepared according to the process described in Tetrahedron Lett., 1995, 36, 6413-6414.

B) 5-Chloro-3-(1,3-benzodioxol-4-yl)-3-hydroxy-1,3-dihydro-2H-indol-2-one

A solution of 1,3-benzodioxol-4-ylmagnesium bromide is prepared starting with 0.85 g of magnesium in 10 ml of THF and a solution of 6.7 g of the compound obtained in the preceding step in 40 ml of THF. This solution is added dropwise and at a temperature below 40° C. to a mixture of 3 g of 5-chloro-1H-indole-2,3-dione in 50 ml of THF and the resulting mixture is then left stirring for one hour. The reaction mixture is poured into saturated $NH_4Cl$ solution and extracted with EtOAc, the organic phase is washed with water and dried over $Na_2SO_4$, and the solvent is evaporated off under vacuum. 1.12 g of the expected product are obtained after crystallization from DCM; m.p.=271° C.

C) 3,5-Dichloro-3-(1,3-benzodioxol-4-yl)-1,3-dihydro-2H-indol-2-one 0.3 ml of thionyl chloride is added, at a temperature below 25° C., to a mixture of 1.1 g of the compound obtained in the preceding step and 0.4 ml of pyridine in 20 ml of DCM, and the mixture is left stirring for 30 minutes. The reaction mixture is washed twice with water, the organic phase is dried over $Na_2SO_4$ and the solvent is evaporated off under vacuum. 0.62 g of the expected product is obtained after crystallization from DCM; m.p.=241° C.

Preparation 1.11

3,5-Dichloro-3-(2-trifluoromethoxyphenyl)-1,3-dihydro-2H-indol-2-one (IV): $R_1$=Cl; $R_2$=H; $R_3$=2-OCF$_3$; $R_4$=H; Hal=Cl A) 5-Chloro-3-hydroxy-3-(2-trifluoromethoxy-phenyl)-1,3-dihydro-2H-indol-2-one A solution of 25 g of 1-bromo-2-trifluoro-methoxybenzene in 130 ml of ether is added dropwise to a mixture of 2.8 g of magnesium in 20 ml of ether, the reflux being maintained once it has started. At the end of the addition, the mixture is refluxed for one hour. A mixture of 7.5 g of 5-chloro-1H-indole-2,3-dione in 100 ml of THF is then added, at a temperature below 40° C., followed by refluxing for one hour. After cooling to RT, the reaction mixture is poured into an ice/concentrated HCl mixture and extracted with EtOAc, the organic phase is washed with water and with 1N NaOH solution and dried over $Na_2SO_4$, and the solvent is evaporated off under vacuum. 6.5 g of the expected product are obtained after crystallization from a DCM/iso ether mixture (20/80; v/v); m.p.=214° C.

B) 3,5-Dichloro-3-(2-trifluoromethoxyphenyl)-1,3-dihydro-2H-indol-2-one 0.7 ml of thionyl chloride is added, at a temperature below 20° C., to a mixture of 2.7 g of the compound obtained in the preceding step and 1 ml of pyridine in 20 ml of DCM, and the mixture is left stirring for one hour. The reaction mixture is washed twice with water, the organic phase is dried over $Na_2SO_4$ and the solvent is evaporated off under vacuum. 1.8 g of the expected product are obtained after crystallization from iso ether; m.p.=185° C.

Preparation 1.12

3-Bromo-5-chloro-3-(2-fluorophenyl)-1,3-dihydro-2H-indol-2-one (IV): $R_1$=Cl; $R_2$=H; $R_3$=2-F; $R_4$=H; Hal=Br A) D,L-2-Fluoromandelic Acid This compound is prepared according to the process described in J. Org. Chem., 1968, 33, 2565-2566. This compound may also be prepared by following the procedure below. A mixture of 17.4 g of 2-fluorobenzaldehyde and 9.6 g of potassium cyanide in 30 ml of ether is cooled to a temperature below 10° C., 15 ml of concentrated HCl are added over 30 minutes and the mixture is left stirring for 2 hours at RT. After separation of the phases by settling, the organic phase is dried over $Na_2SO_4$ and the solvent is evaporated off under vacuum. The crude product thus obtained is taken up in 20 ml of concentrated HCl and refluxed for 5 hours. After cooling to RT, the reaction mixture is extracted with ether, the organic phase is washed with water and dried over $Na_2SO_4$, and the solvent is evaporated off under vacuum. 17.5 g of the expected product are obtained after crystallization from iso ether.

B) N-p-Chlorophenyl-D,L-2-fluoromandelamide

A mixture of 17.5 g of the compound obtained in the preceding step and 13 g of p-chloroaniline in 100 ml of 1,2-dichlorobenzene is refluxed for 3 hours, while removing the water formed using Dean-Stark apparatus. After cooling to RT, the mixture is left to crystallize. The precipitate formed is spin-filtered off and dissolved in EtOAc, the organic phase is washed twice with 4N HCl solution and dried over $Na_2SO_4$, and the solvent is evaporated off under vacuum. 16.2 g of the expected product are obtained after crystallization from iso ether.

C) 5-Chloro-3-(2-fluorophenyl)-1,3-dihydroindol-2-one 16.1 g of the compound obtained in the preceding step are added to a mixture of 64 ml of concentrated (95%) $H_2SO_4$ and 16 ml of fuming sulphuric acid (30% oleum) at RT, and the mixture is then left stirring for 8 hours. The reaction mixture is poured into a mixture of ice/water and extracted with EtOAc, the organic phase is washed twice with water and dried over $Na_2SO_4$ and the solvent is evaporated off under vacuum. 12.2 g of the expected product are obtained after crystallization from iso ether.

D) 3-Bromo-5-chloro-3-(2-fluorophenyl)-1,3-dihydro-2H-indol-2-one

A solution of 0.78 ml of bromine in 20 ml of chloroform is added slowly at RT to a solution of 4 g of the compound obtained in the preceding step in 100 ml of chloroform. The reaction mixture is concentrated under vacuum to give 4 g of the expected product after crystallization from iso ether.

Preparation 1.13

3,5-Dichloro-3-(2-benzyloxyphenyl)-1,3-dihydro-2H-indol-2-one (IV): $R_1$=Cl; $R_2$=H; $R_3$=2-OBzl; $R_4$=H; Hal=Cl A) 1-Bromo-2-benzyloxybenzene A mixture of 35 g of 1-bromo-2-hydroxy-benzene, 30.5 g of benzyl chloride and 50 g of $K_2CO_3$ in 500 ml of acetone is refluxed for 12 hours. The reaction mixture is concentrated under vacuum, the residue is taken up in a water/EtOAc mixture, the organic phase is washed with 1N NaOH solution and with water and dried over $Na_2SO_4$, and the solvent is evaporated off under vacuum. The resulting oil is distilled under reduced pressure to give 50.3 g of the expected product, b.p.=155° C. at 40 Pa.

B) 5-Chloro-3-(2-benzyloxyphenyl)-3-hydroxy-1,3-dihydro-2H-indol-2-one

A solution of 50 g of the compound obtained in the preceding step in 80 ml of THF is added dropwise to a mixture of 5.1 g of magnesium in 20 ml of THF, the reflux being maintained once it has started. At the end of the addition, the mixture is refluxed for 3 hours. This solution is then added dropwise, at a temperature below 40° C., to a mixture of 13 g of 5-chloro-1H-indole-2,3-dione in 100 ml of THF and the resulting mixture is then refluxed for 2 hours. After cooling to RT, the reaction mixture is poured into saturated $NH_4Cl$ solution precooled on an ice bath, and is extracted with EtOAc, the organic phase is washed with water and dried over $Na_2SO_4$, and the solvent is evaporated off under vacuum. The residue is taken up in iso ether and left to crystallize. The precipitate formed is spin-filtered off and washed with boiling iso ether. 16.1 g of the expected product are obtained; m.p.=197° C.

C) 3,5-Dichloro-3-(2-benzyloxyphenyl)-1,3-dihydro-2H-indol-2-one 0.4 ml of thionyl chloride is added, at a temperature below 20° C., to a solution of 1.35 g of the compound obtained in the preceding step and 0.6 ml of pyridine in 30 ml of DCM, and the mixture is left stirring for 30 minutes. The reaction mixture is washed with water, the organic phase is dried over $Na_2SO_4$ and the solvent is evaporated off under vacuum. 1.18 g of the expected product are obtained after crystallization from iso ether.

Preparation 1.14

3,5-Dichloro-3-(2-methoxy-6-methylphenyl)-1,3-dihydro-2H-indol-2-one (IV): $R_1$=Cl; $R_2$=H; $R_3$=2-$OCH_3$; $R_4$=6-$CH_3$; Hal=Cl A) 5-Chloro-3-hydroxy-3-(2-methoxy-6-methylphenyl)-1,3-dihydro-2H-indol-2-one A solution of 2-methoxy-6-methylphenyl-magnesium bromide is prepared starting with 2.2 g of magnesium in 10 ml of THF and a solution of 16 g of 1-bromo-2-methoxy-6-methylbenzene in 40 ml of THF. This solution is added dropwise at RT to a mixture of 6 g of 5-chloro-1H-indole-2,3-dione in 50 ml of THF and the resulting mixture is then refluxed for 1 hour. After cooling to RT, the reaction mixture is poured into 200 ml of 3N HCl solution and extracted with EtOAc, the organic phase is washed with water and dried over $Na_2SO_4$, and the solvent is evaporated off under vacuum. 5.7 g of the expected product are obtained after crystallization from iso ether.

B) 3,5-Dichloro-3-(2-methoxy-6-methylphenyl)-1,3-dihydro-2H-indol-2-one

A mixture of 3 g of the compound obtained in the preceding step and 1 ml of pyridine in 20 ml of DCM is cooled to a temperature below 10° C., 1.3 g of thionyl chloride are added and the mixture is left stirring for 30 minutes at RT. The reaction mixture is washed with water, the organic phase is dried over $Na_2SO_4$ and the solvent is evaporated off under vacuum. 1 g of the expected product is obtained after crystallization from iso ether.

Preparation 1.15

3-Chloro-3-(2-methoxyphenyl)-5-trifluoromethoxy-1,3-dihydro-2H-indol-2-one (IV): $R_1$=$OCF_3$; $R_2$=H; $R_3$=2-$OCH_3$; $R_4$=H; Hal=Cl A) 3-Hydroxy-3-(2-methoxyphenyl)-5-trifluoromethoxy-1,3-dihydro-2H-indol-2-one A solution of 2-methoxyphenylmagnesium bromide is prepared starting with 1.9 g of magnesium in 4 ml of ether and a solution of 14.54 g of 1-bromo-2-methoxybenzene in 21 ml of ether. This solution is added dropwise, under an argon atmosphere, to a mixture of 5 g of 5-trifluoromethoxy-1H-indole-2,3-dione in 26 ml of THF, precooled on an ice bath, the resulting mixture is then heated at the reflux temperature of the ether for 1 hour 30 minutes and is allowed to cool to RT. The reaction mixture is poured slowly into saturated $NH_4Cl$ solution and extracted with EtOAc, the organic phase is washed with 5% $K_2CO_3$ solution, with water and with saturated NaCl solution and dried over $Na_2SO_4$, and the solvent is evaporated off under vacuum. 2.8 g of the expected product are obtained.

B) 3-Chloro-3-(2-methoxyphenyl)-5-trifluoromethoxy-1,3-dihydro-2H-indol-2-one

A mixture of 1 g of the compound obtained in the preceding step in 10 ml of DCM is cooled to 0° C., 0.24 ml of pyridine and then 0.22 ml of thionyl chloride are added and the mixture is left stirring for 15 minutes. This solution is used in this form in Preparation 3.30.

Preparation 1.16

3,5,6-Trichloro-3-(2-methoxyphenyl)-1,3-dihydro-2H-indol-2-one (IV): $R_1$=Cl; $R_2$=6-Cl; $R_3$=2-$OCH_3$; $R_4$=H; Hal=Cl A) 5,6-Dichloro-1H-indole-2,3-dione This compound is prepared according to the procedure described in J. Am. Chem. Soc., 1946, 68, 2697-2703 or according to the procedure described in J. Org. Chem., 1952, 17, 149-156.

B) 5,6-Dichloro-3-hydroxy-3-(2-methoxyphenyl)-1,3-dihydro-2H-indol-2-one 5.57 g of 1-bromo-2-methoxybenzene are added dropwise to a suspension of 0.72 g of magnesium in 15 ml of ether containing a few crystals of iodine, the reflux being maintained once it has started. At the end of the addition, the mixture is refluxed for 2 hours. A suspension of 2.7 g of 5,6-dichloro-1H-indole-2,3-dione in 30 ml of THF is then added and the mixture is refluxed for 30 minutes. After cooling to RT, the reaction mixture is poured into a water/ice/-concentrated HCl mixture and extracted with EtOAc, the organic phase is dried over $Na_2SO_4$ and the solvent is evaporated off under vacuum. The residue is slurried in hot iso ether and the precipitate formed is spin-filtered off and washed with ether. 3 g of the expected product are obtained.

C) 3,5,6-Trichloro-3-(2-methoxyphenyl)-1,3-dihydro-2H-indol-2-one

A suspension of 1.5 g of the compound obtained in the preceding step in 30 ml of DCM is cooled on an ice bath and 0.56 ml of pyridine is added, followed by 0.5 ml of thionyl chloride. After stirring for 1 hour at RT, the reaction mixture is diluted by adding DCM, the organic phase is washed with water to neutral pH and dried over $Na_2SO_4$, and the solvent is evaporated off under vacuum. 1.5 g of the expected product are obtained in the form of a foam, which is used without further purification.

Preparation 1.17

3-Bromo-5,6-dichloro-3-(2-chlorophenyl)-1,3-dihydro-2H-indol-2-one (IV): $R_1$=Cl; $R_2$=6-Cl; $R_3$=2-Cl; $R_4$=H; Hal=Br A) N-3,4-Dichlorophenyl-D,L-2-chloromandelamide This compound is prepared according to the procedure described in step B of Preparation 1.12, starting with 3,4-dichloroaniline and D,L-2-chloromandelic acid; m.p.=160-163° C.

B) 5,6-Dichloro-3-(2-chlorophenyl)-1,3-dihydroindol-2-one

A mixture of 53 ml of concentrated sulphuric acid and 12 ml of fuming sulphuric acid (30% oleum) is cooled to 0° C. and 13 g of the compound obtained in the preceding step are added portionwise. The mixture is left stirring for 24 hours at RT, the reaction mixture is poured into water and the precipitate formed is spin-filtered off. The precipitate is dissolved in EtOAc, the organic phase is washed with water to pH 7 and dried over sodium sulphate, and the solvent is partially evaporated off under vacuum. The crystalline product formed is spin-filtered off and recrystallized from a THF/DCM/EtOAc mixture. 1.3 g of the expected product are obtained; m.p. 198-201° C.

C) 3-Bromo-5,6-dichloro-3-(2-chlorophenyl)-1,3-dihydroindol-2-one

A solution of 0.32 g of bromine in 1 ml of chloroform is added dropwise to a suspension of 1.95 g of the compound obtained in the preceding step in 30 ml of chloroform, and the mixture is left stirring for 30 minutes at RT. The reaction mixture is concentrated under vacuum, the residue is taken up in DCM and the solvent is evaporated off under vacuum. The residue is extracted with EtOAc, the organic phase is washed with water to pH 7 and dried over sodium sulphate, and the solvent is evaporated off under vacuum. The expected product is obtained after crystallization from DCM; m.p.=215-218° C.

Preparation 1.18

3-Bromo-4,5-dichloro-3-(2-chlorophenyl)-1,3-dihydro-2H-indol-2-one (IV): $R_1$=Cl; $R_2$=4-Cl; $R_3$=2-Cl; $R_4$=H; Hal=Br A) 5,6-Dichloro-3-(2-chlorophenyl)-1,3-dihydro-2H-indol-2-one and 4,5-dichloro-3-(2-chlorophenyl)-1,3-dihydro-2H-indol-2-one The process is performed as in step B of Preparation 1.17, starting with 93 g of N-3,4-dichlorophenyl-D,L-2-chloromandelamide. After spin-filtration of the precipitate formed corresponding to 5,6-dichloro-3-(2-chlorophenyl)-1,3-dihydro-2H-indol-2-one, the spin-filtration liquor is concentrated under vacuum to give a mixture of the two expected products, which is used without further purification.

B) 3-Bromo-4,5-dichloro-3-(2-chlorophenyl)-1,3-dihydro-2H-indol-2-one

A solution of 1.71 ml of bromine in 10 ml of DCM is added dropwise at RT to a suspension of 11.55 g of the mixture of compounds obtained in the preceding step in 200 ml of DCM, and, at the end of the addition, a further 0.38 ml of bromine is added. The reaction mixture is concentrated under vacuum, the residue is extracted with EtOAc, the organic phase is washed with water and dried over $Na_2SO_4$, and the solvent is evaporated off under vacuum. The residue is chromatographed on silica gel, eluting with a gradient of the DCM/EtOAc mixture. The following are obtained:

the compound of Preparation 1.17 eluted with a DCM/EtOAc mixture (88/12; v/v).

$^1$H NMR: $d_6$-DMSO: δ (ppm): 7.1: 2s: 2H; 7.5: up: 3H; 8.3: dd: 1H; 11.5: bs: 1H.

the compound of Preparation 1.18 eluted with a DCM/EtOAc mixture (76/24; v/v).

$^1$H NMR: $d_6$-DMSO: δ (ppm): 7.2: d: 1H; 7.5: up: 4H; 8.3: dd: 1H; 11.5: bs: 1H.

Preparation 1.19

3,5-Dichloro-3-(2-methoxyphenyl)-6-methyl-1,3-dihydro-2H-indol-2-one (IV): $R_1$=Cl; $R_2$=6-$CH_3$; $R_3$=2-$OCH_3$; $R_4$=H; Hal=Cl A) Ethyl 2-(2-methoxyphenyl)-2-oxoacetate A solution of 27 g of 1-bromo-2-methoxybenzene in 270 ml of ether is cooled to –70° C. under an argon atmosphere, 90 ml of a 1.6 M solution of n-butyl-lithium in pentane are added dropwise and the mixture is then left stirring for 45 minutes. 78 ml of diethyl oxalate are added rapidly and the mixture is left stirring, while allowing the temperature to return to RT. After stirring for 1 hour at RT, saturated $NH_4Cl$ solution is added to the mixture, the phases are separated after settling has taken place, the aqueous phase is extracted with ether, the combined organic phases are washed with water and then with saturated NaCl solution and dried over $Na_2SO_4$, and the solvents are evaporated off under vacuum. The excess diethyl oxalate is removed by distillation under vacuum (b.p.=87° C. at 2 000 Pa). The resulting product is chromatographed on silica gel, eluting with a DCM/hexane mixture (50/50; v/v) and then with DCM. The product obtained is purified by distillation under vacuum. 13 g of the expected product are obtained; b.p.=110° C. at 3 Pa.

B) 5-Chloro-3-hydroxy-3-(2-methoxyphenyl)-6-methyl-1,3-dihydro-2H-indol-2-one a) tert-Butyl 4-chloro-3-methylphenylcarbamate A mixture of 10 g of 4-chloro-3-methylaniline and 15.26 g of di-tert-butyl dicarbonate in 50 ml of dioxane is left stirring for 24 hours at RT. The reaction mixture is concentrated under vacuum and the residue is chromatographed on silica gel, eluting with a gradient of a DCM/hexane mixture of from (50/50; v/v) to (70/30; v/v). 5.6 g of the expected product are obtained and are used without further purification.

b) A solution of 5 g of tert-butyl 4-chloro-3-methylphenylcarbamate in 45 ml of ether is cooled to –70° C. under an argon atmosphere, 30 ml of a 1.5M solution of tert-butyllithium in pentane are added dropwise, the mixture is left stirring for 1 hour while allowing the temperature to rise to –10° C., and is left stirring for 1 hour 45 minutes at –10° C. The reaction mixture is cooled to –70° C., a solution of 5 g of the compound obtained in step A in 25 ml of THF is added dropwise and the mixture is left stirring for 1 hour while allowing the temperature to rise to –30° C., and is then stirred overnight while allowing the temperature to rise to RT. Saturated $NH_4Cl$ solution is added to the reaction mixture, the THF is evaporated off, the resulting aqueous phase is extracted three times with EtOAc, the organic phase is washed with water, with saturated NaCl solution and dried over $Na_2SO_4$, the solvent is partially evaporated off and the crystalline product is spin-filtered off. 2.6 g of the expected product are obtained; m.p.=254-256° C.

C) 3,5-Dichloro-3-(2-methoxyphenyl)-6-methyl-1,3-dihydro-2H-indol-2-one

A mixture of 2.0 g of the compound obtained in step B in 45 ml of DCM is cooled to 0° C., 0.77 ml of pyridine and then 1.17 g of thionyl chloride are added and the mixture is left stirring for 2 hours after the temperature has been allowed to return to RT. Water and DCM are added to the reaction mixture and, after separation of the phases by settling, the organic phase is washed four times with water and dried over $Na_2SO_4$, and the solvent is evaporated off under vacuum. The expected product is obtained and is used without further purification.

Preparation 1.20

3,5-Dichloro-3-(2-chlorophenyl)-6-methoxy-1,3-dihydro-2H-indol-2-one (IV): $R_1$=Cl; $R_2$=6-OCH$_3$; $R_3$=2-Cl; $R_4$=H; Hal=Cl A) 4-Chloro-3-methoxyaniline A mixture of 36 g of 2-chloro-5-nitroanisole and Raney nickel® in 150 ml of MeOH and 200 ml of THF is hydrogenated in Parr apparatus for 4 hours, at 35° C. and under a pressure of 1.3 bar. The catalyst is filtered off over Celite® and the filtrate is concentrated under vacuum. 28 g of the expected product are obtained and are used without further purification.

B) N-(4-Chloro-3-methoxyphenyl)-D,L-2-chloromandelamide

A mixture of 28 g of the compound obtained in the preceding step and 33.13 g of D,L-2-chloromandelic acid in 128 ml of 1,2-dichlorobenzene is heated at 230° C. for 4 hours, while removing the water formed using Dean-Stark apparatus. The reaction mixture is partially concentrated under vacuum and is left to crystallize. The crystalline product formed is spin-filtered off and washed with iso ether. 40 g of the expected product are obtained.

C) 5-Chloro-3-(2-chlorophenyl)-6-methoxy-1,3-dihydro-2H-indol-2-one 40 g of the compound obtained in the preceding step are added rapidly to 550 g of polyphosphoric acid and the mixture is then heated at 60° C. for 8 hours and left stirring overnight while allowing the temperature to return to RT. Ice-cold water is added to the reaction mixture and the precipitate formed is spin-filtered off and washed with water. The precipitate is taken up in EtOAc and the white product obtained after slurrying is spin-filtered off and washed with iso ether. 17.2 g of the expected product are obtained; m.p.=243-247° C.

D) 5-Chloro-3-(2-chlorophenyl)-3-hydroxy-6-methoxy-1,3-dihydro-2H-indol-2-one 2.56 g of 60% sodium hydride in oil are added at RT, under an argon atmosphere, to a solution of 17.2 g of the compound obtained in the preceding step in 220 ml of THF. After the evolution of gas has ceased, 6.85 g of dimethyl disulphide are added, air is bubbled into the reaction mixture and this mixture is left stirring for 72 hours at RT. Water is added to the reaction mixture, the THF is evaporated off under vacuum, the remaining aqueous phase is extracted with EtOAc, the organic phase is washed with water and with saturated NaCl solution and dried over Na$_2$SO$_4$, and the solvent is evaporated off under vacuum. The product obtained is dissolved in DCM, the solvent is partially concentrated, the mixture is left to crystallize and the crystalline product formed is spin-filtered off. 6 g of the expected product are obtained; m.p.=237-240° C.

E) 3,5-Dichloro-3-(2-chlorophenyl)-6-methoxy-1,3-dihydro-2H-indol-2-one

A suspension of 2.0 g of the compound obtained in the preceding step in 30 ml of DCM is cooled on an ice bath, 0.5 ml of pyridine and then 0.44 ml of thionyl chloride are added and this mixture is left stirring for 30 minutes. At the end of the reaction, a solution of the expected product is obtained, and this solution is used directly in Preparations 3.37 and 3.38.

Preparation 1.21

3,5-Dichloro-3-(2-chlorophenyl)-4-methoxy-1,3-dihydro-2H-indol-2-one (IV): $R_1$=Cl; $R_2$=4-OCH$_3$; $R_3$=2-Cl; $R_4$=H; Hal=Cl A) 5-Chloro-3-(2-chlorophenyl)-6-methoxy-1,3-dihydro-2H-indol-2-one and 5-chloro-3-(2-chlorophenyl)-4-methoxy-1,3-dihydro-2H-indol-2-one The process is performed as in step C of Preparation 1.20. After spin-filtration of the precipitate formed corresponding to 5-chloro-3-(2-chlorophenyl)-6-methoxy-1,3-dihydro-2H-indol-2-one, the spin-filtration liquor is concentrated under vacuum to give a mixture of the two expected products, which is used without further purification.

B) 5-Chloro-3-(2-chlorophenyl)-3-hydroxy-4-methoxy-1,3-dihydro-2H-indol-2-one 1.14 g of 60% sodium hydride in oil are added at RT to a solution of 8 g of the mixture of compounds obtained in the preceding step in 100 ml of THF. After the evolution of gas has ceased, 3 ml of dimethyl disulphide are added, air is bubbled into the reaction mixture and this mixture is left stirring for 72 hours at RT. Water is added to the reaction mixture, the solvents are concentrated under vacuum, the residue is extracted with EtOAc, the organic phase is washed with water and with saturated NaCl solution and dried over Na$_2$SO$_4$, and the solvent is evaporated off under vacuum. 3.05 g of the expected product are obtained after crystallization from DCM; m.p.=228-229° C.

C) 3,5-Dichloro-3-(2-chlorophenyl)-4-methoxy-1,3-dihydro-2H-indol-2-one

A suspension of 1.5 g of the compound obtained in the preceding step in 20 ml of DCM is cooled on an ice bath, 0.37 ml of pyridine and then 0.34 ml of thionyl chloride are added and the mixture is left stirring for 15 minutes. At the end of the reaction, a solution of the expected product in DCM is obtained and is used in this form in Preparations 3.39 and 3.40.

Preparation 1.22

3-Bromo-5-chloro-3-(2-chlorophenyl)-7-fluoro-1,3-dihydro-2H-indol-2-one (IV): $R_1$=Cl; $R_2$=7-F; $R_3$=2-Cl; $R_4$=H; Hal=Br This compound is prepared according to the procedures disclosed in WO 95/18105 in steps A, B and C of Preparation 73.

Preparation 1.23

3,6-Dichloro-3-(2-methoxyphenyl)-5-methyl-1,3-dihydro-2H-indol-2-one (IV): $R_1$=CH$_3$; $R_2$=6-Cl; $R_3$=2-OCH$_3$; $R_4$=H; Hal=Cl A) 6-Chloro-5-methyl-3-methylthio-1,3-dihydro-2H-indol-2-one and 4-chloro-5-methyl-3-methylthio-1,3-dihydro-2H-indol-2-one 8.5 ml of chlorine are introduced into 320 ml of DCM cooled to −70° C., followed by addition, over 20 minutes and at −70° C., of a solution of 24 ml of ethyl methylthioacetate in 60 ml of DCM, and the mixture is left stirring for 15 minutes at −70° C. A solution of 52.64 g of 3-chloro-4-methylaniline in 100 ml of DCM is then added, at −70° C. and over 30 minutes, and the resulting mixture is left stirring for 1 hour 45 minutes at −70° C. Finally, 41.3 ml of triethylamine are added at −70° C. and the mixture is left stirring for 1 hour while allowing the temperature to rise to RT. The reaction mixture is washed twice with 250 ml of water, the organic phase is dried over MgSO$_4$ and the solvent is evaporated off under vacuum. The residue is taken up in a mixture of 600 ml of ether and 130 ml of 2N HCl and is left stirring for 72 hours at RT. An insoluble material is filtered off, the filtrate is allowed to separate by settling, the organic phase is washed twice with water and dried over MgSO$_4$, and the solvent is evaporated off under vacuum. The residue is chromatographed on silica gel, eluting with DCM and then with a DCM/EtOAc mixture (85/15; v/v). The mixture obtained is re-chromatographed on silica gel, eluting with DCM and then with a DCM/EtOAc mixture (95/5; v/v). The two isomers are separated:

the less polar isomer, which is 6-chloro-5-methyl-3-methylthio-1,3-dihydro-2H-indol-2-one, in a yield of 1.16 g;

the more polar isomer, which is 4-chloro-5-methyl-3-methylthio-1,3-dihydro-2H-indol-2-one, in a yield of 0.72 g.

B) 6-Chloro-5-methyl-1H-indole-2,3-dione

A mixture of 1.16 g of 6-chloro-5-methyl-3-methylthio-1,3-dihydro-2H-indol-2-one obtained in the preceding step and 0.681 g of N-chlorosuccinimide in 100 ml of carbon tetrachloride is refluxed for 1 hour. The reaction mixture is concentrated under vacuum, the residue is taken up in a mixture of 80 ml of THF and 20 ml of water, and this mixture is then refluxed for 16 hours. The THF is evaporated off under vacuum, the remaining aqueous phase is extracted with EtOAc, the organic phase is washed with water and with saturated NaCl solution and dried over Na$_2$SO$_4$, and the solvent is evaporated off under vacuum. The residue is chromatographed on silica gel, eluting with DCM and then with a gradient of a DCM/EtOAc mixture up to (85/15; v/v). 0.793 g of the expected product is obtained; m.p.=264° C.

C) 6-Chloro-3-hydroxy-3-(2-methoxyphenyl)-5-methyl-1,3-dihydro-2H-indol-2-one

A solution of 2-methoxyphenylmagnesium bromide is prepared starting with 0.687 g of magnesium in 1.5 ml of ether and a solution of 5.35 g of 1-bromo-2-methoxybenzene in 7.55 ml of ether. This solution is added dropwise, under an argon atmosphere, to a mixture of 1.4 g of the compound obtained in the preceding step in 14 ml of THF precooled on an ice bath, and the resulting mixture is then left stirring while allowing the temperature to rise to RT. After stirring for 1 hour at RT, the reaction mixture is poured slowly into saturated NH$_4$Cl solution, the THF is evaporated off under vacuum, the residue is extracted with EtOAc, the organic phase is washed with water and with saturated NaCl solution and dried over Na$_2$SO$_4$, and the EtOAc is evaporated off under vacuum. The residue is chromatographed on silica gel, eluting with DCM and then with a DCM/MeOH mixture (98/2; v.v). 1.6 g of the expected product are obtained after crystallization from a THF/MeOH mixture; m.p.=266° C.

D) 3,6-Dichloro-3-(2-methoxyphenyl)-5-methyl-1,3-dihydro-2H-indol-2-one

A suspension of 0.913 g of the compound obtained in the preceding step in 10 ml of DCM is cooled on an ice bath, 0.36 ml of pyridine and then 0.33 ml of thionyl chloride are added and the mixture is left stirring for 20 minutes. The reaction mixture is diluted by adding 50 ml of DCM, the organic phase is washed three times with water and dried over Na$_2$SO$_4$ and is partially concentrated under vacuum to a volume of 5 ml. This solution of the expected product is used in this form in Preparations 3.43 and 3.44.

Preparation 1.24

3,4-Dichloro-3-(2-methoxyphenyl)-5-methyl-1,3-dihydro-2H-indol-2-one (IV): R$_1$=CH$_3$; R$_2$=4-Cl; R$_3$=2-OCH$_3$; R$_4$=H; Hal=Cl A) 4-Chloro-5-methyl-1H-indole-2,3-dione This compound is prepared according to the procedure described in step B of Preparation 1.23, starting with 0.72 g of 4-chloro-5-methyl-3-methylthio-1,3-dihydro-2H-indol-2-one and 0.422 g of N-chlorosuccinimide in 72 ml of carbon tetrachloride, and then 58 ml of THF and 14 ml of water. The product obtained is chromatographed on silica gel, eluting with DCM and then with a gradient of a DCM/EtOAc mixture up to (90/10; v/v). 0.5 g of the expected product is obtained.

B) 4-Chloro-3-hydroxy-3-(2-methoxyphenyl)-5-methyl-1,3-dihydro-2H-indol-2-one

A solution of 5 g of 1-bromo-2-methoxybenzene in 7 ml of ether is added dropwise to a suspension of 0.638 g of magnesium in 1.5 ml of ether until the reaction starts, and the addition is then continued while maintaining the reflux. At the end of the addition, the mixture is heated at 30° C. for 20 minutes. This solution is added dropwise, under an argon atmosphere, to a suspension of 1.3 g of the compound obtained in the preceding step in 13 ml of THF precooled on an ice bath, and the mixture is then left stirring while allowing the temperature to rise to RT. After 1 hour at RT, the reaction mixture is poured into saturated NH$_4$Cl solution, the THF is evaporated off under vacuum, the residue is extracted with EtOAc, the organic phase is washed with water and with saturated NaCl solution and dried over Na$_2$SO$_4$, and the solvent is evaporated off under vacuum. The residue is chromatographed on silica gel, eluting with DCM and then with a DCM/MeOH mixture (98/2; v/v). 0.846 g of the expected product is obtained after crystallization from a THF/MeOH mixture; m.p.=262-263° C.

C) 3,4-Dichloro-3-(2-methoxyphenyl)-5-methyl-1,3-dihydro-2H-indol-2-one

A suspension of 0.8 g of the compound obtained in the preceding step in 15 ml of DCM is cooled to 0° C., 0.32 ml of pyridine and then 0.295 ml of thionyl chloride are added and the mixture is left stirring for 45 minutes. The reaction mixture is diluted by adding 15 ml of DCM, the organic phase is washed three times with water and dried over MgSO$_4$, and the solvent is evaporated off under vacuum. 0.51 g of the expected product is obtained.

Preparation 1.25

3-Chloro-3-(2-methoxyphenyl)-3,5,6,7-tetrahydrocyclopenta[f]indol-2(1H)-one (IV): R$_1$+R$_2$=5,6-CH$_2$CH$_2$CH$_2$—; R$_3$=2-OCH$_3$; R$_4$=H; Hal=Cl A) N-(2,3-Dihydro-1H-inden-5-yl)-2-(hydroxyimino)acetamide This compound is prepared according to the process described in Organic Syntheses, 1925, V, 71-74. A solution of 16.5 ml of concentrated HCl in 120 ml of water and a solution of 41.5 g of hydroxylamine hydrochloride in 70 ml of water are added to a mixture of 25 g of 5-aminoindane, 35 g of chloral hydrate and 22 g of Na$_2$SO$_4$ in 600 ml of water, and the mixture is then refluxed for 30 minutes. After cooling the reaction mixture to RT, it is extracted with EtOAc, the organic phase is dried over Na$_2$SO$_4$ and the solvent is evaporated off under vacuum. The residue is taken up in a pentane/iso ether mixture and the precipitate formed is spin-filtered off. 23 g of the expected product are obtained.

B) 1,5,6,7-Tetrahydrocyclopenta[f]indole-2,3-dione

This compound is prepared according to the process described in Organic Syntheses, 1925, V, 71-74. 23 g of the compound obtained in the preceding step are added portionwise to 250 ml of concentrated sulphuric acid, the temperature of the reaction mixture rising to 60° C. At the end of the addition, the mixture is heated at 90° C. for 50 minutes. After cooling to RT, the reaction mixture is poured into 1 litre of ice, 500 ml of EtOAc are added and the mixture is filtered through Celite®. After separation of the filtrate by settling, the organic phase is dried over $Na_2SO_4$ and the solvent is evaporated off under vacuum. The residue is taken up in iso ether and the crystalline product formed is spin-filtered off. 4.2 g of the expected product are obtained.

C) 3-Hydroxy-3-(2-methoxyphenyl)-3,5,6,7-tetrahydrocyclopenta[f]indol-2(1H)-one

A solution of 2-methoxyphenylmangesium bromide is prepared starting with 2.4 g of magnesium, 16.5 g of 1-bromo-2-methoxybenzene and 50 ml of ether. This solution is added dropwise, at a temperature below 30° C., to a mixture of 6.3 g of the compound obtained in the preceding step in 50 ml of THF, and the resulting mixture is then refluxed for 2 hours. After cooling to RT, the reaction mixture is poured into a 3N HCl/ice mixture and extracted with EtOAc, the organic phase is washed with water and dried over $Na_2SO_4$, and the solvent is evaporated off under vacuum. The residue is taken up in hot iso ether and the precipitate formed is spin-filtered off and washed with boiling iso ether. 3.5 g of the expected product are obtained.

D) 3-Chloro-3-(2-methoxyphenyl)-3,5,6,7-tetrahydrocyclopenta[f]indol-2(1H)-one

A mixture of 3.5 g of the compound obtained in the preceding step and 1 ml of triethylamine in 20 ml of DCM is cooled to 10° C., 0.8 ml of thionyl chloride is added and the mixture is left stirring for 15 minutes. The reaction mixture is washed with water and dried over $Na_2SO_4$, and the solvent is evaporated off under vacuum. The expected product is obtained and is used without further purification.

Preparation 1.26

3-Chloro-3-(2-methoxy-6-methylphenyl)-5,6-dimethyl-1,3-dihydro-2H-indol-2-one (IV): $R_1=CH_3$; $R_2=6-CH_3$; $R_3=2-OCH_3$; $R_4=6-CH_3$; Hal=Cl A) 5,6-Dimethyl-1H-indol-2,3-dione This compound is prepared according to the procedures described in steps A and B of Preparation 1.25, starting with 3,4-dimethylaniline.

B) 3-Hydroxy-3-(2-methoxy-6-methylphenyl)-5,6-dimethyl-1,3-dihydro-2H-indol-2-one A solution of 2-methoxy-6-methylphenyl-magnesium bromide is prepared starting with 13.75 g of 1-bromo-2-methoxy-6-methylbenzene, 1.9 g of magnesium and 30 ml of THF. This solution is added dropwise at RT to a suspension of 5 g of the compound obtained in the preceding step in 40 ml of THF, and the resulting mixture is then refluxed for 1 hour 30 minutes. After cooling to RT, 200 ml of 3N HCl solution are added, the mixture is extracted with EtOAc, the organic phase is washed with water and with saturated NaCl solution and dried over $Na_2SO_4$, and the solvent is evaporated off under vacuum. The residue is chromatographed on silica gel, eluting with a DCM/EtOAc/THF mixture (70/20/10; v/v/v). 3 g of the expected product are obtained after crystallization; m.p.=288° C.

C) 3-Chloro-3-(2-methoxy-6-methylphenyl)-5,6-dimethyl-1,3-dihydro-2H-indol-2-one A mixture of 1.5 g of the compound obtained in the preceding step in 20 ml of DCM is cooled on an ice bath, 0.4 ml of pyridine and then 0.5 ml of thionyl chloride are added and the mixture is left stirring for 15 minutes under cold conditions and then for 15 minutes at RT. A suspension of the expected product in DCM is obtained and is used in this form in Preparation 3.47.

Preparation 1.27

3,5-Dichloro-3-(2-methoxyphenyl)-6-trifluoromethyl-1,3-dihydro-2H-indol-2-one (IV): $R_1=Cl$; $R_2=6-CF_3$; $R_3=2-OCH_3$; $R_4=H$; Hal=Cl A) 5-Chloro-3-hydroxy-3-(2-methoxyphenyl)-6-trifluoromethyl-1,3-dihydro-2H-indol-2-one a) tert-Butyl 4-chloro-3-trifluoromethyl-phenylcarbamate This compound is prepared according to the procedure described in step B a) of Preparation 1.5, starting with 4-chloro-3-trifluoromethylaniline and di-tert-butyl dicarbonate in dioxane. The expected product is obtained in the form of an oil which solidifies;

m.p.=90° C.

b) A solution of 4 g of tert-butyl 4-chloro-3-trifluoromethylphenylcarbamate in 30 ml of ether is cooled to −70° C., under an argon atmosphere, 22 ml of a 1.5 M solution of tert-butyllithium in pentane are added dropwise and the mixture is left stirring for 1 hour while allowing the temperature to rise to −10° C. and is left stirring for 2 hours 30 minutes at −10° C. The reaction mixture is cooled to −70° C., a solution of 3.05 g of the compound obtained in step A of Preparation 1.19 in 15 ml of THF is added dropwise and the resulting mixture is left stirring for 1 hour while allowing the temperature to rise to −30° C., and is then stirred for 16 hours while allowing the temperature to rise to RT. Saturated $NH_4Cl$ solution is added to the reaction mixture, the ether and THF are evaporated off, the resulting aqueous phase is extracted with EtOAc, the organic phase is washed with water and with saturated NaCl solution and dried over $Na_2SO_4$, and the solvent is evaporated off under vacuum. The residue is chromatographed on silica gel, eluting with DCM and then with a DCM/EtOAc mixture (90/10; v/v). 1.48 g of the expected product are obtained after crystallization from an iso ether/hexane mixture; m.p. 230-231° C.

B) 3,5-Dichloro-3-(2-methoxyphenyl)-6-trifluoromethyl-1,3-dihydro-2H-indol-2-one A suspension of 1.3 g of the compound obtained in step A in 8 ml of DCM is cooled to 0° C., 0.43 ml of pyridine and then 0.4 ml of thionyl chloride are added and the mixture is left stirring for 15 minutes. The reaction mixture is washed three times with water, the organic phase is dried over $Na_2SO_4$ and the solvent is evaporated off under vacuum. 1.2 g of the expected product are obtained and are used without further purification.

Preparation 1.28

3-Chloro-3-(2-chlorophenyl)-5,6-dimethyl-1,3-dihydro-2H-indol-2-one (IV): $R_1$=$CH_3$; $R_2$=6-$CH_3$; $R_3$=Cl; $R_4$=H; Hal=Cl A) N-(3,4-Dimethylphenyl)-D,L-2-chloromandelamide A mixture of 50 g of 3,4-dimethylaniline and 76.5 g of D,L-2-chloromandelic acid in 250 ml of 1,2-dichlorobenzene is heated at 227° C. for 7 hours, while removing the water formed using Dean-Stark apparatus. The reaction mixture is concentrated to half its volume under vacuum and is left to crystallize at RT. The crystalline product formed is spin-filtered off and washed with iso ether. 89.42 g of the expected product are obtained, a sample of which is recrystallized from a DCM/iso ether mixture;

m.p.=172-173° C.

B) 3-(2-Chlorophenyl)-5,6-dimethyl-1,3-dihydroindol-2-one 100 ml of 95% sulphuric acid are cooled to −10° C., 12 ml of fuming sulphuric acid (65% oleum) are added dropwise over 30 minutes and the mixture is left stirring while allowing the temperature to rise to +10° C. The mixture is cooled again to 0° C., 23.8 g of the compound obtained in the preceding step are added portionwise over 10 minutes and the mixture is left stirring while allowing the temperature to rise, which stabilizes at 29° C. After stirring for 2 hours at RT, the reaction mixture is poured onto ice and the precipitate formed is spin-filtered off. The precipitate is dissolved in 1 000 ml of DCM and 200 ml of THF, the pH is brought to 2 by adding solid $K_2CO_3$, the resulting mixture is filtered and the filtrate is concentrated under vacuum. The residue is chromatographed on silica gel, eluting with a gradient of a DCM/EtOAc/THF mixture of from (90/10/5; v/v/v) to 80/20/5; v/v/v). 7.72 g of the expected product are obtained; m.p.=231° C.

C) 3-(2-Chlorophenyl)-3-hydroxy-5,6-dimethyl-1,3-dihydroindol-2-one 0.65 g of 60% sodium hydride in oil is added at RT, under an argon atmosphere, to a solution of 4 g of the compound obtained in the preceding step in 70 ml of THF. After the evolution of gas has ceased, 1.7 ml of dimethyl disulphide are then added and a stream of air is bubbled into the reaction mixture for 4 hours at RT. The reaction mixture is poured into water, the THF is concentrated under vacuum, the aqueous phase is extracted with EtOAc, the organic phase is washed with water and with saturated NaCl solution and dried over $Na_2SO_4$, the solvent is partially concentrated under vacuum and the crystalline product formed is spin-filtered off. 3.3 g of the expected product is obtained; m.p.=251-253° C.

D) 3-Chloro-3-(2-chlorophenyl)-5,6-dimethyl-1,3-dihydro-2H-indol-2-one

A suspension of 2 g of the compound obtained in the preceding step in 15 ml of DCM is cooled to 0° C., 0.8 ml of pyridine and then 0.74 ml of thionyl chloride are added and the mixture is left stirring for 30 minutes. The reaction mixture is diluted by adding 60 ml of DCM, the organic phase is washed with 45 ml of water and dried over $Na_2SO_4$, and the solvent is partially concentrated under vacuum at a temperature below 40° C., to a volume of 20 ml. This solution is used in this form in Preparations 3.60 and 3.61.

Preparation of the compounds of formula (V)

Preparation 2.1

(2S)-N,N-Dimethylpyrrolidine-2-carbothioamide trifluoroacetate (V), TFA: $R_5$=N($CH_3$)$_2$; W=S; n=1

A) (2S)-N,N-Dimethyl-1-(tert-butoxycarbonyl)-pyrrolidine-2-carbothioamide

This compound is prepared according to the procedure described in step A) of Example 84 of EP 0 526 348 B.

B) (2S)-N,N-Dimethylpyrrolidine-2-carbothioamide trifluoroacetate

A solution of 18 g of the compound obtained in the preceding step in 5 ml of DCM is cooled to 4° C., 15 ml of TFA are added and the mixture is left stirring for 15 hours at 4° C. The reaction mixture is concentrated under vacuum under cold conditions, the residue is taken up four times in DCM and the solvent is evaporated off under vacuum each time. 12 g of the expected product are obtained after drying, and are used without further purification.

Preparation 2.2

(2S)-N,N-Dimethylpiperidine-2-carboxamide hydrochloride (V), HCl: $R_5$=N($CH_3$)$_2$; W=O; n=2

A) (2S)-N,N-Dimethyl-2-(tert-butoxycarbonyl)-piperidine-2-carboxamide 6.2 g of HOBT and then 9.45 g of DCC are added at RT to a solution of 10 g of (2S)-1-(tert-butoxycarbonyl)piperidine-2-carboxylic acid (commercial) in 130 ml of DCM, and the mixture is left stirring for 1 hour. The reaction mixture is cooled on an ice bath, dimethylamine gas is added by bubbling for two times 10 minutes and the mixture is then left stirring overnight at RT. An insoluble material is filtered off and the filtrate is concentrated under vacuum. The residue is chromatographed on silica gel, eluting with a gradient of a DCM/MeOH mixture of from (98/2; v/v) to (96/4; v/v). The product obtained is taken up in ether and the precipitate is spin-filtered off. 8.5 g of the expected product are obtained.

B) (2S)-N,N-Dimethylpiperidine-2-carboxamide hydrochloride

A mixture of 8.5 g of the compound obtained in the preceding step and 85 ml of 4N hydrochloric ether is left stirring for 1 hour 30 minutes. The reaction mixture is concentrated under vacuum, the residue is taken up several times with DCM and the solvent is evaporated off each time under vacuum. 6.25 g of the expected product are obtained.

Preparation 2.3

N,N-Dimethylpiperidine-2-carboxamide hydrochloride (V), HCl: $R_5$=N($CH_3$)$_2$; W=O; n=2

This compound is prepared according to the procedures described in steps A and B of Preparation 2.2, starting with racemic 1-(tert-butoxycarbonyl)-piperidine-2-carboxylic acid (commercial).

Preparation of the compounds of formulae (II) and (II')

Preparation 3.1

(2S)-1-[5-Chloro-3-(2-methoxyphenyl)-2-oxo-2,3-dihydro-1H-indol-3-yl]-N,N-dimethylpyrrolidine-2-carboxamide, laevorotatory isomer (II): $R_1$=Cl; $R_2$=H; $R_3$=2-OCH$_3$; $R_4$=H; $R_5$=—N(CH$_3$)$_2$; n=1; W=O 4.1 g of (2S)-N,N-dimethylpyrrolidine-2-carboxamide (commercial) are added to a suspension of 8.8 g of the compound obtained in Preparation 1.1 in 120 ml of chloroform and 30 ml of THF, and the mixture is left stirring for 30 minutes at RT. 3.7 g of DIPEA are then added and the mixture is left stirring for 3 hours at RT. 0.4 g of (2S)-N,N-dimethylpyrrolidine-2-carboxamide is then added and the mixture is left stirring for 48 hours. The reaction mixture is concentrated under vacuum at RT, the residue is taken up in water, 300 ml of EtOAc are added, the mixture is left stirring and the precipitate present (the most polar compound on TLC on alumina DCM/MeOH (96/4; v/v)) is spin-filtered off. The precipitate is taken up in 100 ml of EtOAc, left stirring for 2 hours and spin-filtered off. It is taken up in 100 ml of boiling EtOAc, left stirring for 1 hour and spin-filtered off. The precipitate is dissolved in a hot mixture of 100 ml of THF, 50 ml of MeOH and 10 ml of water, the resulting solution is filtered and the filtrate is concentrated under vacuum to a volume of 100 ml and is left overnight. 3.78 g of the expected product are obtained after the crystalline compound formed has been spin-filtered off.

$\alpha_D^{25}$=−242° (c=0.12; chloroform)

Preparation 3.2 tert-Butyl (2S)-1-[5-chloro-3-(2-methoxyphenyl)-2-oxo-2,3-dihydro-1H-indol-3-yl]pyrrolidine-2-carboxylate, laevorotatory isomer (II'): $R_1$=Cl; $R_2$=H; $R_3$=2-OCH$_3$; $R_4$=H; n=1

A solution of 3.4 g of tert-butyl (2S)-pyrrolidine-2-carboxylate (commercial) in 5 ml of DCM is added to a suspension of 6 g of the compound obtained in Preparation 1.1 in 40 ml of DCM and 20 ml of THF, followed by addition of 5.42 ml of triethylamine, and the mixture is left stirring for 2 hours at RT. The reaction mixture is concentrated under vacuum, the residue is extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on silica gel, eluting with DCM and then with a DCM/MeOH mixture (98/2 v/v). The diastereoisomers are separated and the most polar compound is collected. 3.3 g of the expected product are obtained.

$\alpha_D^{25}$=−148.5° (c=0.229; chloroform)

Preparation 3.3

(2S)-1-[5-Chloro-3-(2-methoxyphenyl)-2-oxo-2,3-dihydro-1H-indol-2-yl]-N,N-dimethylpyrrolidine-2-carbothioamide, laevorotatory isomer (II): $R_1$=Cl; $R_2$=H; $R_3$=2-OCH$_3$; $R_4$=H; $R_5$=N(CH$_3$)$_2$; n=1; W=S A solution of 3.5 g of the compound obtained in Preparation 2.1 and 3.5 g of triethylamine in 20 ml of DCM is added dropwise at RT to a mixture of 4 g of the compound obtained in Preparation 1.1 in 20 ml of DCM, and the mixture is left stirring for 30 minutes at RT. A further 0.87 g of triethylamine is added and the mixture is left stirring for 24 hours at RT. The resulting mixture is concentrated under vacuum, the residue is extracted with EtOAc, the organic phase is washed with 5% KHSO$_4$ solution and with water and dried over Na$_2$SO$_4$, and the solvent is evaporated off under vacuum. The residue is chromatographed on alumina, eluting with a DCM/MeOH mixture (99.75/0.25; v/v). The diastereoisomers are separated to give 0.7 g of the expected product after crystallization from a DCM/iso ether mixture; m.p.=225° C.

$\alpha_D^{25}$=−236° (c=0.2; chloroform)

Preparation 3.4

Methyl (2S)-1-[5-chloro-3-(2-methoxyphenyl)-2-oxo-2,3-dihydro-1H-indol-3-yl]pyrrolidine-2-carboxylate; the more polar isomer (II): $R_1$=Cl; $R_2$=H; $R_3$=2-OCH$_3$; $R_4$=H; $R_5$=OCH$_3$; n=1; W=O.

A solution of 1.7 g of methyl (2S)-pyrrolidine-2-carboxylate hydrochloride (commercial) and 1.73 ml of DIPEA in 50 ml of DCM is added at RT to a suspension of 3 g of the compound obtained in Preparation 1.1 in 20 ml of THF, and the mixture is heated at 65° C. overnight. The reaction mixture is concentrated under vacuum, the residue is taken up in 5% K$_2$CO$_3$ solution and extracted with EtOAc, the organic phase is washed with saturated NaCl solution and dried over Na$_2$SO$_4$, and the solvent is evaporated off under vacuum. The residue is chromatographed on silica gel, eluting with a DCM/EtOAc mixture (95/5; v/v). The diastereoisomers are separated and the fractions enriched in the more polar compound are collected. 0.793 g of the expected product is obtained and is used without further purification.

Preparations 3.5 and 3.6

(2S)-1-[5-Chloro-3-(2-ethoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=2-OCH$_2$CH$_3$; $R_4$=H; $R_5$=N(CH$_3$)$_2$; n=1; W=O A mixture of 2.5 g of the compound obtained in Preparation 1.2, 1.2 [lacuna] of (2S)-N,N-dimethylpyrrolidine-2-carboxamide and 1 ml of triethylamine in 20 ml of DCM is left stirring for 3 hours. The reaction mixture is washed twice with water, the organic phase is dried over Na$_2$SO$_4$ and the solvent is evaporated off under vacuum. The residue is taken up in DCM under cold conditions over 16 hours and the precipitate formed is spin-filtered off and washed with acetone to give 0.35 g of the less polar isomer, isomer A: compound of Preparation 3.5. The spin-filtration and washing liquors are chromatographed on alumina, eluting with a DCM/MeOH mixture (98/2; v/v). The other isomer is separated out:

the more polar isomer, isomer B: compound of Preparation 3.6, to give 0.52 g.

Preparations 3.7 and 3.8

(2S)-1-[5-Chloro-3-(3-methoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=3-OCH$_3$; $R_4$=H; $R_5$=N(CH$_3$)$_2$; n=1; W=O A mixture of 1 g of the compound obtained in Preparation 1.3, 0.7 g of (2S)-N,N-dimethylpyrrolidine-2-carboxamide and 1 ml of triethylamine in 20 ml of DCM is left stirring for 2 hours at RT. The reaction mixture is washed with water, the organic phase is dried over Na$_2$SO$_4$ and the solvent is evaporated off under vacuum. The residue is taken up in DCM, cooled to 4° C. and left for 16 hours. The precipitate formed is spin-filtered off and dried to give 0.72 g of the more polar isomer, isomer B: compound of Preparation 3.8. The spin-filtration liquor is chromatographed on alumina, eluting with a DCM/MeOH mixture (99.9/0.1; v/v). The other isomer is separated out:
  the less polar isomer, isomer A: compound of Preparation 3.7, to give 0.18 g.

Preparations 3.9 and 3.10

(2S)-1-[5-Chloro-3-(4-methoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=4-OCH$_3$; $R_4$=H; $R_5$=N(CH$_3$)$_2$; n=1; W=O 1.1 g of (2S)-N,N-dimethylpyrrolidine-2-carboxamide are added at RT to the solution of the compound obtained in Preparation 1.4 in DCM, the mixture is left stirring for 15 minutes at RT, 1.2 g of triethylamine is then added and this mixture is left stirring for 30 minutes at RT. The reaction mixture is washed with water, the organic phase is dried over Na$_2$SO$_4$ and the solvent is evaporated off under vacuum. The residue is taken up in cold acetone and the crystalline product formed is spin-filtered off to give 0.75 g of the more polar isomer, isomer B: compound of Preparation 3.10. The spin-filtration liquor is chromatographed on silica gel, eluting with a DCM/EtOAc mixture (95/5; v/v). The other isomer is separated out:
  the less polar isomer, isomer A: compound of preparation 3.9, to give 0.37 g.

Preparations 3.11 and 3.12

(2S)-1-[5-Chloro-3-(2,3-diemthoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=2-OCH$_3$; $R_4$=3-OCH$_3$; $R_5$=N(CH$_3$)$_2$; n=1; W=O A mixture of 1 g of the compound obtained in Preparation 1.5, 0.5 g of (2S)-N,N-dimethylpyrrolidine-2-carboxamide and 0.3 g of triethylamine in 5 ml of DCM and 15 ml of THF is left stirring for 16 hours at RT. The precipitate formed is spin-filtered off, washed with THF and dried to give 0.22 g of the less polar isomer, isomer A: compound of Preparation 3.11. The spin-filtration and washing liquors are concentrated under vacuum and the residue is chromatographed on silica gel, eluting with a DCM/MeOH mixture (98.5/1.5; v/v). The other isomer is separated out:
  the more polar isomer, isomer B: compound of Preparation 3.12, to give 0.68 g.

Preparations 3.13 and 3.14

(2S)-1-[5-Chloro-3-(2,4-dimethoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=2-OCH$_3$; $R_4$=4-OCH$_3$; $R_5$=N(CH$_3$)$_2$; n=1; W=O 0.7 g of (2S)-N,N-dimethylpyrrolidine-2-carboxamide and 0.8 ml of triethylamine are added at RT to the solution of the compound obtained in Preparation 1.6. in DCM, and the mixture is left stirring for 1 hour at RT. The reaction mixture is washed twice with water, the organic phase is dried over Na$_2$SO$_4$ and the solvent is evaporated off under vacuum. The residue is chromatographed on alumina, eluting with a DCM/MeOH mixture (99.9/01.0; v/v). The diasteroisomers are separated:
  the less polar, isomer A: compound of Preparation 3.13, to give 0.13 g.
  the more polar, isomer B: compound of Preparation 3.14, to give 0.17 g.

Preparations 3.15 and 3.16

(2S)-1-[5-Chloro-3-(2,5-dimethoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=2-OCH$_3$; $R_4$=5-OCH$_3$; $R_5$=N(CH$_3$)$_2$; n=1; W=O

[lacuna] Preparation 1.7, 0.5 g of (2S)-N,N-dimethylpyrrolidine-2-carboxamide and 0.3 g of triethylamine in 10 ml of DCM [lacuna]. The reaction mixture is washed with 5% NaHCO$_3$ solution and with water, the organic phase is dried over Na$_2$SO$_4$ and the solvent is evaporated off under vacuum. The residue is chromatographed on silica gel, eluting with DCM and then with a DCM/MeOH mixture (98/2; v/v). The diasteroisomers are separated:
  the less polar, isomer A: compound of Preparation 3.15, to give 0.2 g.
  the more polar, isomer B: compound of Preparation 3.16, to give 0.38 g.

Preparations 3.17 and 3.18

(2S)-1-[5-Chloro-3-(2,6-dimethoxyphenyl)-2-oxo-2,3-dihydro-1H-indol-3-yl]-N,N-dimethylpyrrolidine-2-carboxamide, isomer A and isomer B (II): $R_1$=Cl; $R_2$=H; $R_3$=2-OCH$_3$; $R_4$=6-OCH$_3$; $R_5$=N(CH$_3$)$_2$; n=1; W=O A mixture of 1.9 g of the compound obtained in Preparation 1.8, 1 g of (2S)-N,N-dimethylpyrrolidine-2-carboxamide and 1 ml of triethylamine in 20 ml of DCM is left stirring for 3 hours at RT. The reaction mixture is washed with water, the organic phase is dried over Na$_2$SO$_4$ and the solvent is evaporated off under vacuum. The residue is chromatographed on silica gel, eluting with a DCM/MeOH mixture (98/2; v/v). The diastereoisomers are separated:
  the less polar, isomer A: compound of Preparation 3.17, which is crystallized from iso ether to give 0.38 g.
  $\alpha_D^{25}$=−371° (c=0.15, chloroform)
  the more polar, isomer B: compound of Preparation 3.18, to give 0.4 g.

Preparations 3.19 and 3.20

(2S)-1-[5-Chloro-3-(3,5-dimethoxyphenyl)-2-oxo-3,
4-dihydro-1H-indol-3-yl]-N,N-dimethylpyrrolidine-
2-carboxamide, isomer A and isomer B (II): $R_1$=Cl; $R_2$=H; $R_3$=3-OCH$_3$; $R_4$=5-OCH$_3$; $R_5$=N(CH$_3$)$_2$; n=1; W=O A mixture of 1.4 g of the compound obtained in Preparation 1.9, 0.7 g of (2S)-N,N-dimethylpyrrolidine-2-carboxamide and 0.8 ml of triethylamine in 20 ml of DCM is left stirring for 3 hours at RT. The reaction mixture is washed with water, the organic phase is dried over Na$_2$SO$_4$ and the solvent is evaporated off under vacuum. The residue is chromatographed on silica gel, eluting with a DCM/EtOAc mixture (95/5; v/v). The diastereoisomers are separated:

the less polar, isomer A: compound of Preparation 3.19, to give 0.18 g.

the more polar, isomer B: compound of Preparation 3.20.

Preparations 3.21 and 3.22

(2S)-1-[5-Chloro-3-(1,3-benzodioxol-4-yl)-2-oxo-2,
3-dihydro-1H-indol-3-yl]-N,N-dimethylpyrrolidine-
2-carboxamide, isomer A and isomer B (II): $R_1$=Cl; $R_2$=H; $R_3$+$R_4$=2,3-O—CH$_2$—O—; $R_5$=N(CH$_3$)$_2$; n=1; W=O A mixture of 0.61 g of the compound obtained in Preparation 1.10, 0.45 g of (2S)-N,N-dimethylpyrrolidine-2-carboxamide and 1 ml of triethylamine in 20 ml of DCM is left stirring for 1 hour at RT. The reaction mixture is washed with water, the organic phase is dried over Na$_2$SO$_4$ and the solvent is evaporated off under vacuum. The residue is chromatographed on silica gel, eluting with a DCM/MeOH mixture (98.5/1.5; v/v). The diastereoisomers are separated:

the less polar, isomer A: compound of Preparation 3.21, to give 0.19 g; m.p.=241° C.

the more polar, isomer B: compound of Preparation 3.22.

Preparations 3.23 and 3.24

(2S)-1-[5-Chloro-3-(2-trifluoromethoxyphenyl)-2-
oxo-2,3-dihydro-1H-indol-3-yl]-N,N-dimethylpyrro-
lidine-2-carboxamide, isomer A and isomer B (II): $R_1$=Cl; $R_2$=H; $R_3$=2-OCF$_3$; $R_4$=H; $R_5$=N(CH$_3$)$_2$; n=1; W=O A mixture of 1.8 g of the compound obtained in Preparation 1.11, 1.5 g of (2S)-N,N-dimethylpyrrolidine-2-carboxamide and 2 ml of DIPEA in 20 ml of DCM is left stirring for 3 hours at RT. The reaction mixture is washed with water, the organic phase is dried over Na$_2$SO$_4$ and the solvent is evaporated off under vacuum. The residue is chromatographed on silica gel, eluting with a DCM/MeOH mixture (99/1; v/v). The diastereoisomers are separated:

the less polar, isomer A: compound of Preparation 3.23, to give 0.34 g.

the more polar, isomer B: compound of Preparation 3.24.

Preparations 3.25 and 3.26

(2S)-1-[5-Chloro-3-(2-fluorophenyl)-2-oxo-2,3-dihy-
dro-1H-indol-3-yl]-N,N-dimethylpyrrolidine-2-car-
boxamide, isomer A and isomer B (II): $R_1$=Cl; $R_2$=H; $R_3$=2-F; $R_4$=H; $R_5$=N(CH$_3$)$_2$; n=1; W=O A mixture of 1.56 g of the compound obtained in Preparation 1.21, 1 g of (2S)-N,N-dimethylpyrrolidine-2-carboxamide and 1 ml of triethylamine in 50 ml of DCM is left stirring for 24 hours at RT. The precipitate formed is spin-filtered off and washed with DCM to give 0.62 g of the more polar isomer, isomer B: compound of Preparation 3.26;

$\alpha_D^{20}$=+99° (c=0.15; chloroform).

The spin-filtration and washing liquors are concentrated under vacuum, the residue is taken up in a minimum amount of DCM, the precipitate of isomer B formed is spin-filtered off again and the spin-filtration liquor is concentrated under vacuum. The residue is chromatographed on alumina, eluting with a DCM/MeOH mixture (99.5/0.5; v/v). The other isomer is separated out:

the less polar, isomer A: compound of Preparation 3.25, to give 0.42 g.

$\alpha_D^{20}$=−182° (c=0.14; chloroform).

Preparation 3.27

(2S)-1-[5-Chloro-3-(2-benzyloxyphenyl)-2-oxo-2,3-
dihydro-1H-indol-3-yl]-N,N-dimethylpyrrolidine-2-
carboxamide, laevorotatory isomer (II): $R_1$=Cl; $R_2$=H; $R_3$=2-OBzl; $R_4$=H; $R_5$=N(CH$_3$)$_2$; n=1; W=O A mixture of 4 g of the compound obtained in Preparation 1.13, 1.8 g of (2S)-N,N-dimethylpyrrolidine-2-carboxamide and 3 ml of triethylamine in 20 ml of DCM is left stirring for 12 hours at RT. The reaction mixture is washed with water, the organic phase is dried over Na$_2$SO$_4$ and the solvent is evaporated off under vacuum. The residue is taken up in a THF/iso ether mixture and left to crystallize. The precipitate formed is spin-filtered off to give 2.2 g of the more polar compound by TLC on alumina, DCM/MeOH (99/1; v/v). The spin-filtration liquor is chromatographed on alumina, eluting with a DCM/MeOH mixture (99/1; v/v) and a further 0.4 g of the more polar compound is collected. The 2.6 g of the more polar compound thus obtained are re-chromatographed on alumina, eluting with a DCM/MeOH mixture (99/1; v/v). 2.1 g of the expected product are obtained; m.p.=240° C.

$\alpha_D^{20}$=−171° (c=0.15; chloroform).

Preparations 3.28 and 3.29

(2S)-1-[5-Chloro-3-(2-methoxy-6-methylphenyl)-2-
oxo-2,3-dihydro-1H-indol-3-yl]-N,N-dimethylpyrro-
lidine-2-carboxamide, isomer A and isomer B (II): $R_1$=Cl; $R_2$=H; $R_3$=2-OCH$_3$; $R_4$=6-CH$_3$; $R_5$=N(CH$_3$)$_2$; n=1; W=O A mixture of 1 g of the compound obtained in Preparation 1.14, 0.5 g of (2S)-N,N-dimethylpyrrolidine-2-carboxamide and 1 ml of triethylamine in 20 ml of DCM is left stirring for 48 hours. The reaction mixture is washed with water, with 5% NaHCO$_3$ solution and with water, the organic phase is dried over Na$_2$SO$_4$ and the solvent is evaporated off under vacuum.

The residue is chromatographed on silica gel, eluting with a DCM/MeOH mixture (98/2; v/v). The diastereoisomers are separated:
- the less polar, isomer A: compound of Preparation 3.28, to give 0.4 g.
- the more polar, isomer B: compound of Preparation 3.29, to give 0.6 g.

Preparation 3.30

(2S)-1-[5-Trifluoromethoxy-3-(2-methoxyphenyl)-2-oxo-2,3-dihydro-1H-indol-3-yl]-N,N-dimethylpyrrolidine-2-carboxamide, the less polar isomer (II): $R_1$=OCF$_3$; $R_2$=H; $R_3$=2-OCH$_3$; $R_4$=H; $R_5$=N(CH$_3$)$_2$; n=1; W=O 0.839 g of (2S)-N,N-dimethylpyrrolidine-2-carboxamide and 0.5 ml of DIPEA are added to the solution of the compound obtained in Preparation 1.15 in DCM and the mixture is then heated at 35° C. for 4 hours. The reaction mixture is concentrated under vacuum, the residue is taken up in 5% K$_2$CO$_3$ solution and extracted with EtOAc, the organic phase is dried over Na$_2$SO$_4$ and the solvent is evaporated off under vacuum. The residue is chromatographed three times successively on alumina, eluting with a DCM/MeOH mixture (98/2; v/v). The diastereoisomers are separated and the less polar compound is collected during the chromatography, but the more polar compound is collected by TLC on alumina, eluting with DCM/MeOH (99.5/0.5; v/v). 0.371 g of the expected product is obtained.

Preparation 3.31

(2S)-1-[5,6-Dichloro-3-(2-methoxyphenyl)-2-oxo-2,3-dihydro-1H-indol-3-yl]-N,N-dimethylpyrrolidine-2-carboxamide, mixture of diastereoisomers (II): $R_1$=Cl; $R_2$=6-Cl; $R_3$=2-OCH$_3$; $R_4$=H; $R_5$=N(CH$_3$)$_2$; n=1; W=O 0.81 g of (2S)-N,N-dimethylpyrrolidine-2-carboxamide is added to a mixture of 1.95 g of the compound obtained in Preparation 1.16 in 25 ml of DCM, followed by addition of 2 ml of DIPEA, and the mixture is left stirring overnight at RT. The reaction mixture is concentrated under vacuum, the residue is taken up in saturated K$_2$CO$_3$ solution and extracted three times with EtOAc, the organic phase is washed three times with water and with saturated NaCl solution and dried over Na$_2$SO$_4$, and the solvent is evaporated off under vacuum. 1.774 g of the expected product are obtained in the form of a mixture of diastereoisomers after crystallization from iso ether.

Preparation 3.32

(2S)-1-[5,6-Dichloro-3-(2-chlorophenyl)-2-oxo-2,3-dihydro-1H-indol-3-yl]-N,N-dimethylpyrrolidine-2-carboxamide, mixture of diastereoisomers (II): $R_1$=Cl; $R_2$=6-Cl; $R_3$=2-Cl; $R_4$=H; $R_5$=N(CH$_3$)$_2$; n=1; W=O A mixture of 1 g of the compound obtained in Preparation 1.17 and 0.73 g of (2S)-N,N-dimethylpyrrolidine-2-carboxamide in 10 ml of chloroform is left stirring for 48 hours at RT. The reaction mixture is concentrated under vacuum, the residue is taken up in 5% K$_2$CO$_3$ solution and extracted with EtOAc (presence of a precipitate in the organic phase), the organic phase is washed twice with water, the phases are separated by settling and THF is added until the precipitate has dissolved. The solvents are partially concentrated under vacuum to give a precipitate in the EtOAc; iso ether is added until precipitation is complete and the precipitate formed is spin-filtered off. 1 g of the expected product is obtained in the form of the mixture of diastereoisomers.

Preparations 3.33 and 3.34

(2S)-1-[4,5-Dichloro-3-(2-chlorophenyl)-2-oxo-2,3-dihydro-1H-indol-3-yl]-N,N-dimethylpyrrolidine-2-carboxamide, isomer A and isomer B (II): $R_1$=Cl; $R_2$=4-Cl; $R_3$=2-Cl; $R_4$=H; $R_5$=N(CH$_3$)$_2$; n=1; W=O A solution of 1.5 g of the compound obtained in Preparation 1.18 in 15 ml of DCM is cooled on an ice bath, 1.09 g of (2S)-N,N-dimethylpyrrolidine-2-carboxamide are added and the mixture is left stirring for 3 hours at RT. The reaction mixture is concentrated under vacuum, the residue is taken up in water and extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on alumina, eluting with DCM and then with a DCM/MeOH mixture (98/2; v/v). The diastereoisomers are separated:
- the less polar, isomer A: compound of Preparation 3.33, which is crystallized under cold conditions from DCM to give 0.487 g.

$\alpha_D^{25}$=+243.7° (c=0.2; chloroform)
- the more polar, isomer B: compound of Preparation 3.34, to give 0.3 g.

Preparations 3.35 and 3.36

(2S)-1-[5-Chloro-3-(2-methoxyphenyl)-6-methyl-2-oxo-2,3-dihydro-1H-indol-3-yl]-N,N-dimethylpyrrolidine-2-carboxamide, isomer A and isomer B (II): $R_1$=Cl; $R_2$=6-CH$_3$; $R_3$=2-OCH$_3$; $R_4$=H; $R_5$=N(CH$_3$)$_2$; n=1; W=O.

0.95 g of (2S)-N,N-dimethylpyrrolidine-2-carboxamide and then 0.66 g of triethylamine are added at RT to a solution of the compound obtained in Preparation 1.19 in 20 ml of DCM, and the mixture is left stirring for 5 minutes at RT. The reaction mixture is poured into 5% K$_2$CO$_3$ solution and extracted with EtOAc, and the precipitate formed is spin-filtered off. The precipitate is dissolved in hot THF and the solution is filtered and combined with the EtOAc organic phase. The solvents are partially concentrated under vacuum and the crystalline product formed is spin-filtered off [lacuna], the more polar isomer, by TTC on alumina, eluting with DCM/MeOH 98/2; v/v), isomer B: compound of Preparation 3.36. Isomer B is recrystallized three times from a DCM/EtOAc mixture and is then chromatographed on alumina, eluting with a DCM/MeOH mixture (99.5/0.5; v/v). 0.779 g of isomer B is obtained after crystallization from a DCM/iso ether mixture; m.p.=266-269° C.

$\alpha_D^{25}$=−234.5° (c=0.18; chloroform)

The spin-filtration liquors from all the above crystallizations are combined and concentrated under vacuum. The residue is chromatographed on alumina, eluting with a DCM/

MeOH mixture (99.5/0.5; v/v) and the other diastereoisomer is separated out:

the less polar, isomer A: compound of Preparation 3.35, which is crystallized from a DCM/EtOAc mixture to give 0.47 g; m.p.=257-260° C.

$\alpha_D^{25}$=+122.1° (c=0.26; chloroform)

Preparations 3.37 and 3.38

(2S)-1-[5-Chloro-3-(2-chlorophenyl)-6-methoxy-2-oxo-2,3-dihydro-1H-indol-3-yl]-N,N-dimethylpyrrolidine-2-carboxamide, isomer A and isomer B (II): $R_1$=Cl; $R_2$=6-OCH$_3$; $R_3$=2-Cl; $R_4$=H; $R_5$=N(CH$_3$)$_2$; n=1; W=O The solution of the compound obtained in Preparation 1.20 in DCM is cooled on an ice bath, 1.75 g of (2S)-N,N-dimethylpyrrolidine-2-carboxamide are added and the mixture is left stirring for 3 hours while allowing the temperature to return to RT. The reaction mixture is concentrated under vacuum, the residue is taken up in 5% K$_2$CO$_3$ solution and extracted with EtOAc containing THF and MeOH, the organic phase is washed with water and with saturated NaCl solution and dried over Na$_2$SO$_4$, and the solvent is evaporated off under vacuum. The residue is chromatographed on alumina, eluting with a DCM/MeOH mixture (99/1; v/v) and then (98/2; v/v). The diastereoisomers are separated:

the less polar, isomer A: compound of Preparation 3.37, which is crystallized from a DCM/iso ether mixture to give 0.51 g; m.p.=240-247° C.

$\alpha_D^{25}$=+190.7° (c=0.16; chloroform)

the more polar, isomer B: compound of Preparation 3.38, which is crystallized from a DCM/MeOH mixture to give 0.664 g; m.p. 239-244° C.

$\alpha_D^{25}$=−289.8° (c=0.15; chloroform/MeOH 7/1)

Preparations 3.39 and 3.40

(2S)-1-[5-Chloro-3-(2-chlorophenyl)-4-methoxy-2-oxo-2,3-dihydro-1H-indol-3-yl]-N,N-dimethylpyrrolidine-2-carboxamide, isomer A and isomer B (II): $R_1$=Cl; $R_2$=4-OCH$_3$; $R_3$=2-Cl; $R_4$=H; $R_5$=N(CH$_3$)$_2$; n=1; W=O 1.31 g of (2S)-N,N-dimethylpyrrolidine-2-carboxamide and then 1.2 g of DIPEA are added at RT to the solution of the compound obtained in Preparation 1.21 in DCM. The reaction mixture is concentrated under vacuum, the residue is extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on alumina, eluting with a DCM/MeOH mixture of from (97.5/2.5; v/v) to (97/3; v/v). The diastereoisomers are separated:

the less polar, isomer A: compound of Preparation 3.39, which is crystallized from a DCM/iso ether mixture to give 0.42 g; m.p.=259-260° C.

$\alpha_D^{25}$=+206.9° (c=0.13; chloroform)

the more polar, isomer B: compound of Preparation 3.40, to give 0.32 g.

Preparations 3.41 and 3.42

(2S)-1-[5-Chloro-3-(2-chlorophenyl)-7-fluoro-2-oxo-2,3-dihydro-1H-indol-3-yl]-N,N-dimethylpyrrolidine-2-carboxamide, isomer A and isomer B (II): $R_1$=Cl; $R_2$=7-F; $R_3$=2-Cl; $R_4$=H; $R_5$=N(CH$_3$)$_2$; n=1; W=O A solution of 1.45 g of (2S)-N,N-dimethylpyrrolidine-2-carboxamide in 5 ml of DCM is added dropwise at RT to a solution of 1.9 g of the compound obtained in Preparation 1.22 in 15 ml of THF, and the mixture is left stirring for 12 hours at RT. Water is added to the reaction mixture, the THF and DCM are evaporated off under vacuum, the resulting aqueous phase is extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on alumina, eluting with DCM and then with a DCM/MeOH mixture (98.5/1.5; v/v). The diastereoisomers are separated:

the less polar, isomer A: compound of Preparation 3.41, which is crystallized from a DCM/iso ether/hexane mixture to give 0.612 g; m.p.=246-247° C.

$\alpha_D^{25}$=+194.4° (c=0.2; chloroform)

the more polar, isomer B: compound of Preparation 3.42, to give 0.61 g.

Preparations 3.43 and 3.44

(2S)-1-[6-Chloro-3-(2-methoxyphenyl)-5-methyl-2-oxo-2,3-dihydro-1H-indol-3-yl]-N,N-dimethylpyrrolidine-2-carboxamide, isomer A and isomer B (II): $R_1$=CH$_3$; $R_2$=6-Cl; $R_3$=2-OCH$_3$; $R_4$=H; $R_5$=N(CH$_3$)$_2$; n=1; W=O 0.855 g of (2S)-N,N-dimethylpyrrolidine-2-carboxamide is added at RT to the solution of the compound obtained in Preparation 1.23 in DCM, and the mixture is left stirring overnight at RT. The reaction mixture is concentrated under vacuum, the residue is extracted with EtOAc, the organic phase is washed with 5% K$_2$CO$_3$ solution and dried over Na$_2$SO$_4$, and the solvent is partially concentrated under vacuum. The crystalline product formed is spin-filtered off [lacuna], the more polar isomer, by TLC on alumina, eluting with EtOAc, isomer B: compound of Preparation 3.44. 0.32 g of isomer B is obtained after recrystallization from a DCM/EtOAc mixture; m.p.=263° C.

$\alpha_D^{25}$=−256.8° (c=0.17; chloroform)

The above crystallization spin-filtration liquors are concentrated under vacuum and the residue is chromatographed on alumina, eluting with a DCM/MeOH mixture of from (99.75/0.25; v/v) to (98.5/1.5; v/v). The other diastereoisomer is separated out:

the less polar, isomer A: compound of Preparation 3.43, which is crystallized from a DCM/iso ether/hexane mixture; m.p.=257° C.

$\alpha_D^{25}$=+131° (c=0.18; chloroform)

Preparation 3.45

(2S)-1-[4-Chloro-3-(2-methoxyphenyl)-5-methyl-2-oxo-2,3-dihydro-1H-indol-3-yl]-N,N-dimethylpyrrolidine-2-carboxamide, diastereoisomer mixture (II): $R_1=CH_3$; $R_2=4$-Cl; $R_3=2$-$OCH_3$; $R_4=H$; $R_5=N(CH_3)_2$; n=1; W=O A mixture of 0.503 g of the compound obtained in Preparation 1.24 and 0.476 g of (2S)-N,N-dimethylpyrrolidine-2-carboxamide in 5 ml of DCM is left stirring for 18 hours at RT. The reaction mixture is diluted by adding 30 ml of DCM, the organic phase is washed with water and dried over $Na_2SO_4$, and the solvent is evaporated off under vacuum. The residue is chromatographed on silica gel, eluting with a DCM/MeOH mixture (96/4; v/v). 0.369 g of the expected product is obtained in the form of a mixture of diastereoisomers.

Preparation 3.46

(2S)-1-[3-(2-Methoxyphenyl)-2-oxo-1,2,3,5,6,7-hexahydrocyclopenta[f]indol-3-yl]-N,N-dimethylpyrrolidine-2-carboxamide, diastereoisomer mixture (II): $R_1+R_2=5,6$-$CH_2CH_2CH_2$—; $R_3=2$-$OCH_3$; $R_4=H$; $R_5=N(CH_3)_2$; n=1; W=O A mixture of the compound obtained in Preparation 1.25, 1 g of (2S)-N,N-dimethylpyrrolidine-2-carboxamide and 1 ml of triethylamine in 30 ml of DCM is left stirring for 48 hours at RT. The reaction mixture is washed with water, the organic phase is dried over $Na_2SO_4$ and the solvent is evaporated off under vacuum. The residue is chromatographed on silica gel, eluting with a DCM/EtOAc mixture (90/10; v/v). 0.87 g of the expected product is obtained after crystallization from a DCM/iso ether mixture.

Preparation 3.47

(2S)-1-[3-(2-Methoxy-6-methylphenyl)-5,6-dimethyl-2-oxo-2,3-dihydro-1H-indol-3-yl]-N,N-dimethylpyrrolidine-2-carboxamide, the more polar isomer (II): $R_1=CH_3$; $R_2=6$-$CH_3$; $R_3=2$-$OCH_3$; $R_4=6$-$CH_3$; $R_5=N(CH_3)_2$; n=1; W=O 1.43 g of (2S)-N,N-dimethylpyrrolidine-2-carboxamide and then 1.75 ml of DIPEA are added at RT to the suspension of the compound obtained in Preparation 1.26 in DCM, and the mixture is left stirring overnight. The reaction mixture is concentrated under vacuum, the residue is taken up in 5% $K_2CO_3$ solution and extracted with EtOAc, the organic phase is dried over $Na_2SO_4$ and the solvent is evaporated off under vacuum. The residue is chromatographed on silica gel, eluting with a DCM/MeOH mixture (96/4; v/v) and the more polar compound is collected. 0.127 g of the expected product is obtained after crystallization from a DCM/iso ether mixture; m.p.=194-197° C.

Preparations 3.48 and 3.49

(2S)-1-[5-Chloro-3-(2-methoxyphenyl)-2-oxo-2,3-dihydro-1H-indol-3-yl]-N,N-dimethylpiperidine-2-carboxamide, isomer A and isomer B (II): $R_1=Cl$; $R_2=H$; $R_3=2$-$OCH_3$; $R_4=H$; $R_5=N(CH_3)_2$; n=1; W=O A solution of 2.41 g of the compound obtained in Preparation 2.2 and 4 ml of triethylamine in 10 ml of MeOH is added dropwise at RT to a suspension of 1.93 g of the compound obtained in Preparation 1.1 in 19 ml of THF, and the mixture is left stirring for 12 hours at RT. The mixture is concentrated under vacuum, the residue is extracted with EtOAc, the organic phase is washed with 5% $K_2CO_3$ solution, with water and with saturated NaCl solution and dried over $Na_2SO_4$, and the solvent is evaporated off under vacuum. The residue is chromatographed on silica gel, eluting with DCM and then with a DCM/MeOH mixture (97/3; v/v). The diastereoisomers are separated:

the less polar, isomer A: compound of Preparation 3.48, which is re-chromatographed on alumina, eluting with DCM and then with a DCM/MeOH mixture (97/3; v/v) to give 0.634 g after crystallization from a DCM/iso ether mixture;
m.p.=229° C.
$\alpha_D^{25}=+190.9°$ (c=0.188; chloroform)

the more polar, isomer B: compound of Preparation 3.49, which is re-chromatographed on alumina, eluting with DCM and then with a DCM/MeOH mixture (97/3; v/v) to give 0.987 g after crystallization from a DCM/iso ether mixture;
m.p.=243° C.
$\alpha_D^{25}=-182.7°$ (c=0.214; chloroform)

Preparations 3.50 and 3.51

1-[5-Chloro-3-(2,5-dimethoxyphenyl)-2-oxo-2,3-dihydro-1H-indol-3-yl]-N,N-dimethylpiperidine-2-carboxamide, racemic isomer A and racemic isomer B (II): $R_1=Cl$; $R_2=H$; $R_3=2$-$OCH_3$; $R_4=5$-$OCH_3$; $R_5=N(CH_3)_2$; n=2; W=O A solution of 2.13 g of the compound obtained in Preparation 1.7 in 14 ml of DCM is cooled on an ice bath, 2.54 g of the compound obtained in Preparation 2.3 are added, followed by addition of 1.83 ml of triethylamine, and the mixture is left stirring for 72 hours at RT. Water is added to the reaction mixture, the DCM is evaporated off under vacuum, the aqueous phase is extracted with EtOAc, the organic phase is washed with 5% $K_2CO_3$ solution, with water and with saturated NaCl solution and dried over $Na_2SO_4$, and the solvent is evaporated off under vacuum. The residue is chromatographed on alumina, eluting with DCM and then with a DCM/MeOH mixture (99/1; v/v). The two pairs of enantiomers are separated:

the less polar, racemic isomer A: compound of Preparation 3.50, which is crystallized from a DCM/iso ether/hexane mixture to give 0.606 g,; m.p.=217° C.
the more polar, racemic isomer B: compound of Preparation 3.51.

Preparation 3.52

(2S)-1-[5,6-Dichloro-3-(2-chlorophenyl)-2-oxo-2,3-dihydro-1H-indol-3-yl]-N,N-dimethylpiperidine-2-carboxamide, mixture of diastereoisomers (II): $R_1=Cl$; $R_2=6$-Cl; $R_3=2$-Cl; $R_4=H$; $R_5=N(CH_3)_2$; n=2; W=O 2.66 ml of DIPEA are added to a mixture of 1.5 g of the compound obtained in Preparation 2.2 in 20 ml of DCM, followed by addition of 3 g of the compound obtained in Preparation 1.17, and the mixture is left stirring for 10 minutes at RT. The reaction mixture is washed with 5% $K_2CO_3$ solution and with saturated NaCl solution, the organic phase is dried over $Na_2SO_4$ and the solvents are concentrated under vacuum. The residue is chromatographed on alumina, eluting with a DCM/MeOH mixture (97.5/2.5; v/v). 1.821 g of the expected product are obtained.

Preparation 3.53

(2S)-1-[5,6-Dichloro-3-(2-methoxyphenyl)-2-oxo-2,3-dihydro-1H-indol-3-yl]-N,N-dimethylpiperidine-2-carboxamide, the more polar isomer (II): $R_1$=Cl; $R_2$=6-Cl; $R_3$=2-$OCH_3$; $R_4$=H; $R_5$=$N(CH_3)_2$; n=2; W=O 1.1 g of the compound obtained in Preparation 2.2 are added to a mixture of 1.95 g of the compound obtained in Preparation 1.16 in 25 ml of DCM, followed by addition of 2 ml of DIPEA, and the mixture is left stirring overnight at RT. The mixture is concentrated under vacuum, the residue is taken up in 5% $K_2CO_3$ solution and extracted three times with EtOAc, the organic phase is washed with water and with saturated NaCl solution and dried over $Na_2SO_4$, and the solvent is evaporated off under vacuum. The residue is chromatographed on alumina, eluting with DCM/MeOH (98/2; v/v). The diastereoisomers are separated and the more polar compound is collected. 0.821 g of the expected product is obtained.

Preparations 3.54 and 3.55

(2S)-1-[5-Chloro-3-(2-chlorophenyl)-7-fluoro-2-oxo-2,3-dihydro-1H-indol-3-yl]-N,N-dimethylpiperidine-2-carboxamide, isomer A and isomer B (II): $R_1$=Cl; $R_2$=7-F; $R_3$=2-Cl; $R_4$=H; $R_5$=$N(CH_3)_2$; n=2; W=O 1.6 g of the compound obtained in Preparation 2.2 are added to a solution of 3.4 g of the compound obtained in Preparation 1.22 in 30 ml of DCM, followed by addition of 4 ml of DIPEA, and the mixture is heated at 40° C. for 4 hours. The mixture is concentrated under vacuum, the residue is extracted with EtOAc and washed with 5% $K_2CO_3$ solution, with water and with saturated NaCl solution and dried over $Na_2SO_4$, and the solvent is evaporated off under vacuum. The residue is chromatographed on silica gel, eluting with DCM/EtOAc (83/17; v/v) and then re-chromatographed on alumina, eluting with a gradient of a DCM/MeOH mixture of from (99.25/0.75; v/v) to (96.5/3.5; v/v). The diastereoisomers are separated:

the less polar, isomer A: compound of Preparation 3.54, which is crystallized from ether/hexane to give 0.53 g; m.p.=136° C.

$\alpha_D^{25}$=+200° (c=0.1; chloroform)

the more polar, isomer B: compound of Preparation 3.55, which is crystallized from iso ether to give 1.51 g; m.p.=233° C.

$\alpha_D^{25}$=−275.8° (c=0.12; chloroform)

Preparations 3.56 and 3.57

(2S)-1-[5-Chloro-3-(2-methoxyphenyl)-6-methyl-2-oxo-2,3-dihydro-1H-indol-3-yl]-N,N-dimethylpiperidine-2-carboxamide, isomer A and isomer B (II): $R_1$=Cl; $R_2$=6-$CH_3$; $R_3$=2-$OCH_3$; $R_4$=H; $R_5$=$N(CH_3)_2$; n=2; W=O A mixture of 1.97 g of the compound obtained in Preparation 1.19, 1.25 g of the compound obtained in Preparation 2.2 and 2.2 ml of DIPEA in 25 ml of DCM is left stirring overnight at RT. The mixture is concentrated under vacuum, extracted with EtOAc, washed with 5% $K_2CO_3$ solution and with water and dried over $Na_2SO_4$, and the solvent is evaporated off under vacuum. The residue is chromatographed on alumina, eluting with DCM/MeOH (99/1; v/v). The diastereoisomers are separated:

the less polar, isomer A: compound of Preparation 3.56, to give 0.92 g; m.p.=228-229° C.

$\alpha_D^{25}$=+197.5° (c=0.125; chloroform)

the more polar, isomer B: compound of Preparation 3.57, to give 1.527 g.

Preparations 3.58 and 3.59

(2S)-1-[5-Chloro-3-(2-methoxyphenyl)-6-trifluoromethyl-2-oxo-2,3-dihydro-1H-indol-3-yl]-N,N-dimethylpiperidine-2-carboxamide, isomer A and isomer B (II): $R_1$=Cl; $R_2$=6-$CF_3$; $R_3$=2-$OCH_3$; $R_4$=H; $R_5$=$N(CH_3)_2$; n=2; W=O 0.5 g of the compound obtained in Preparation 2.2 and 0.9 ml of triethylamine are added at RT to a solution of 1.2 g of the compound obtained in Preparation 1.27 in 7 ml of DCM, and the mixture is left stirring for 18 hours. Water is added to the reaction mixture, the DCM is evaporated off under vacuum, the aqueous phase is extracted with EtOAc, the organic phase is washed with 5% $K_2CO_3$ solution, with water and with saturated NaCl solution and dried over $Na_2SO_4$, and the solvent is evaporated off under vacuum. The residue is chromatographed on alumina, eluting with a DCM/MeOH mixture (99/1; v/v). The diastereoisomers are separated:

the less polar, isomer A: compound of Preparation 3.58, which is crystallized from DCM/iso ether to give 0.611 g; m.p.=241-242° C.

$\alpha_D^{25}$=+204.63° (c=0.216; chloroform)

the more polar, isomer B: compound of Preparation 3.59, to give 0.77 g.

Preparations 3.60 and 3.61

1-[3-(2-Chlorophenyl)-5,6-dimethyl-2-oxo-2,3-dihydro-1H-indol-3-yl]-N,N-dimethylpiperidine-2-carboxamide, racemic isomer A and racemic isomer B (II): $R_1$=$CH_3$; $R_2$=6-$CH_3$; $R_3$=2-Cl; $R_4$=H; $R_5$=$N(CH_3)_2$; n=2; W=O 20 ml of DCM, 1.6 g of the compound obtained in Preparation 2.3 and 2.7 g of DIPEA are added to the solution of the compound obtained in Preparation 1.28 and the mixture is then heated at 45° C. for 3 hours. The mixture is concentrated under vacuum, the residue is taken up in 5% $K_2CO_3$ solution and extracted with EtOAc, the organic phase is dried over $Na_2SO_4$ and the solvent is evaporated off under vacuum. The residue is chromatographed on alumina, eluting with a DCM/MeOH mixture of from (99.5/0.5; v/v) to (98/2; v/v). The two pairs of enantiomers are separated:

the less polar, racemic isomer A: compound of Preparation 3.60, which is crystallized from DCM/iso ether to give 0.31 g; m.p.=168-170° C.

the more polar, racemic isomer B: compound of Preparation 3.61, which is crystallized from DCM/iso ether to give 1.03 g.

EXAMPLE 1

(2S)-1-[5-Chloro-1-[(2,4-dimethoxyphenyl)-sulphonyl]-3-(2-methoxyphenyl)-2-oxo-2,3-dihydro-1H-indol-3-yl]-N,N-dimethylpyrrolidine-2-carboxamide, laevorotatory isomer (I): $R_1$=Cl; $R_2$=H; $R_3$=2-$OCH_3$; $R_4$=H; $R_5$=—N($CH_3$)$_2$; $R_6$=2-$OCH_3$; $R_7$=$OCH_3$; n=1; W=O A suspension of 3.76 g of the compound obtained in Preparation 3.1 in 35 ml of DMF is cooled on an ice bath, 0.407 g of 60% sodium hydride in oil is added, under an argon atmosphere, and the mixture is warmed to RT and left stirring until dissolved. The reaction mixture is cooled on an ice bath, 2.35 g of 2,4-dimethoxybenzenesulphonyl chloride are added and the mixture is left stirring for 3 hours 30 minutes at RT. 5% $K_2CO_3$ solution is added, the mixture is extracted with EtOAc, the organic phase is washed with saturated NaCl solution and dried over $Na_2SO_4$, and the solvent is evaporated off under vacuum. The residue is dissolved in DCM, iso ether and hexane are added, the solvents are partially concentrated under vacuum at RT and the precipitate formed is spin-filtered off. 3.8 g of the expected product are obtained.

$\alpha_D^{25}$=−226.9° (c=0.2; chloroform)
$^1$H NMR: $d_6$-DMSO: δ (ppm): 1.0 to 1.7: 2mt: 4H; 1.9 to 3.7: mt+2bs: 8H; 3.2: s: 3H; 3.7: s: 3H; 4.3: d: 1H; 6.6: mt: 2H; 6.8: mt: 3H; 7.1: t: 1H; 7.3: dd: 1H; 7.5: d: 1H; 7.6: d: 1H; 7.8: d: 1H.

EXAMPLE 2

(2S)-1-[5-Chloro-1-[(2,4-dimethoxyphenyl)-sulphonyl]-3-(2-methoxyphenyl)-2-oxo-2,3-dihydro-1H-indol-3-yl]-N-ethylpyrrolidine-2-carboxamide, laevorotatory isomer (I): $R_1$=Cl; $R_2$=H; $R_3$=2-$OCH_3$; $R_4$=H; $R_5$=—NH$CH_2CH_3$; $R_6$=2-$OCH_3$; $R_7$=$OCH_3$; n=1; W=O A) tert-Butyl (2S)-1-[5-chloro-1-[(2,4-dimethoxyphenyl) sulphonyl]-3-(2-methoxyphenyl)-2-oxo-2,3-dihydro-1H-indol-3-yl]pyrrolidine-2-carboxylate, laevorotatory isomer A solution of 3.25 g of the compound obtained in Preparation 3.2 in 30 ml of DMF is cooled on an ice bath, 0.323 g of 60% sodium hydride in oil is added, under an argon atmosphere, and the mixture is left stirring for 20 minutes. 1.9 g of 2,4-dimethoxybenzenesulphonyl chloride are then added and the mixture is left stirring for 4 hours at RT. Water is added to the reaction mixture, the resulting mixture is extracted with EtOAc, the organic phase is washed with 5% $K_2CO_3$ solution, with water and with saturated NaCl solution and dried over $Na_2SO_4$, and the solvent is evaporated off under vacuum. The residue is chromatographed on silica gel, eluting with DCM and then with a DCM/MeOH mixture (99/1; v/v). 3.37 g of the expected product are obtained after crystallization from a DCM/iso ether mixture; m.p.=136° C.

$\alpha_D^{25}$=−190.25° (c=0.195; chloroform)

B) (2S)-1-[5-Chloro-1-[(2,4-dimethoxyphenyl)-sulphonyl]-3-(2-methoxyphenyl)-2-oxo-2,3-dihydro-1H-indol-3-yl] pyrrolidine-2-carboxylic acid A mixture of 1.8 g of the compound obtained in the preceding step in 20 ml of a 4N solution of HCl in dioxane is left stirring overnight at RT. The mixture is concentrated under vacuum, the residue is taken up in DCM and the solvent is evaporated off under vacuum. 1.64 g of the expected product are obtained and are used without further purification.

C) (2S)-1-[5-Chloro-1-[(2,4-dimethoxyphenyl)-sulphonyl]-3-(2-methoxyphenyl)-2-oxo-2,3-dihydro-1H-indol-3-yl]-N-ethylpyrrolidine-2-carboxamide, laevorotatory isomer A mixture of 0.5 g of the compound obtained in the preceding step, 0.44 g of PyBOP and 0.108 g of DIPEA in 5 ml of DCM and 1 ml of THF is left stirring for 5 minutes at RT, followed by addition of 0.11 g of a 70% solution of ethylamine in water, and the mixture is left stirring for 2 hours at RT. The mixture is concentrated under vacuum, the residue is extracted with EtOAc, the organic phase is washed with 5% $K_2CO_3$ solution, with water and with saturated NaCl solution and dried over $Na_2SO_4$, and the solvent is evaporated off under vacuum. The residue is chromatographed on alumina, eluting with a DCM/MeOH mixture (99/1; v/v). 0.315 g of the expected product is obtained after crystallization from a DCM/iso ether mixture.

$\alpha_D^{25}$=−151.8° (c=0.22; chloroform)
$^1$H NMR: $d_6$-DMSO: δ (ppm): 1.0: t: 3H; 1.2 to 1.5: mt: 4H; 2.0 and 2.6: q+t: 2H; 3.0: mt: 2H; 3.4: s: 3H; 3.6: s: 3H; 3.8: bs: 4H; 6.6: s+dd: 2H; 6.8: 2d: 2H; 7.2: mt: 2H; 7.4: dd: 1H; 7.6: 3d+s: 4H.

EXAMPLE 3

(2S)-1-[5-Chloro-1-[(2,4-dimethoxyphenyl)-sulphonyl]-3-(2-methoxyphenyl)-2-oxo-2,3-dihydro-1H-indol-3-yl]-2-(azetidin-1-ylcarbonyl)pyrrolidine, laevorotatory isomer (I) $R_1$=Cl; $R_2$=H; $R_3$=2-$OCH_3$; $R_4$=H;

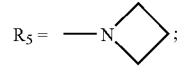

$R_6$=2-$OCH_3$; $R_7$=$OCH_3$; n=1; W=O.

A mixture of 0.56 g of the compound obtained in step B of Example 2, 0.496 g of PyBOP and 0.114 g of DIPEA in 5 ml of DCM and 1 ml of THF is left stirring for 5 minutes at RT, followed by addition of 0.18 g of azetidine hydrochloride and 0.22 g of DIPEA, and the mixture is left stirring for 3 hours at RT. The mixture is concentrated under vacuum, the residue is taken up in 5% $K_2CO_3$ solution and extracted with EtOAc, the organic phase is washed three times with 0.5 N HCl solution and with saturated NaCl solution and dried over $Na_2SO_4$, and the solvent is evaporated off under vacuum. The residue is chromatographed on silica gel, eluting with a DCM/MeOH mixture (98/2; v/v). 0.32 g of the expected product is obtained after crystallization from an ether/iso ether/hexane mixture;
m.p.=161-166° C.
$\alpha_D^{25}$=−169.8° (c=0.19; chloroform)

EXAMPLE 4

(2S)-1-[5-Chloro-1-[(2,4-dimethoxyphenyl)-sulphonyl]-3-(2-methoxyphenyl)-2-oxo-2,3-dihydro-1H-indol-3-yl]-N,N-dimethylpyrrolidine-2-carbothioamide, laevorotatory isomer (I): $R_1$=Cl; $R_2$=H; $R_3$=2-$OCH_3$; $R_4$=H; $R_5$=—N($CH_3$)$_2$; $R_6$=2-$OCH_3$; $R_7$=$OCH_3$; n=1; W=S A mixture of 0.27 g of the compound obtained in Preparation 3.3 in 5 ml of DMF is cooled to 4° C., 0.026 g of 60% sodium hydride in oil is added, under a nitrogen atmosphere, and the mixture is left stirring for 15 minutes at 4° C. 0.139 g of 2,4-dimethoxybenzenesulphonyl chloride is then added and the mixture is left stirring for 3 hours at RT. 50 ml of water are added to the reaction mixture, the resulting mixture is extracted with EtOAc, the organic phase is washed with 5% Na$_2$CO$_3$ solution, with saturated NaCl solution and with water and dried over Na$_2$SO$_4$, and the solvent is evaporated off under vacuum. The residue is chromatographed on silica gel, eluting with a DCM/EtOAc mixture (97/3; v/v). 0.18 g of the expected product is obtained after crystallization from a DCM/iso ether mixture; m.p.=164° C.

$\alpha_D^{25}$=−25° (c=0.2; chloroform)

$^1$H NMR: d$_6$-DMSO: δ (ppm): 1.3 to 2.2: 4mt: 4H; 2.4 and 3.0: 2mt: 2H; 2.7: s: 3H; 3.2: s: 3H; 3.4: s: 3H; 3.7: s: 3H; 3.9: s: 3H; 4.9: dd: 1H; 6.7: mt: 2H; 6.9: mt: 3H; 7.3: dt: 1H; 7.4: dd: 1H; 7.8: d: 1H; 7.9: d: 1H; 8.0: d: 1H

EXAMPLE 5

Methyl (2S)-1-[5-chloro-1-[(2,4-dimethoxyphenyl) sulphonyl]-3-(2-methoxyphenyl)-2-oxo-2,3-dihydro-1H-indol-3-yl]pyrrolidine-2-carboxylate, laevorotatory isomer (I): R$_1$=Cl; R$_2$=H; R$_3$=2-OCH$_3$; R$_4$=H; R$_5$=—OCH$_3$; R$_6$=2-OCH$_3$; R$_7$=OCH$_3$; n=1; W=O A solution of 0.793 g of the compound obtained in Preparation 3.4 in 8 ml of DMF is cooled to 0° C., 0.096 g of 60% sodium hydride in oil is added, under an argon atmosphere, and the mixture is left stirring until the evolution of gas has ceased. 0.564 g of 2,4-dimethoxybenzenesulphonyl chloride is then added and the mixture is left stirring for 3 hours at RT. The reaction mixture is poured into water and extracted with EtOAc, the organic phase is washed with water and with saturated NaCl solution and dried over Na$_2$SO$_4$, and the solvent is evaporated off under vacuum. The residue is chromatographed on silica gel, eluting with a DCM/EtOAc mixture (97/3; v/v). The fractions containing only the more polar compound are collected. 0.495 g of the expected product is obtained after crystallization from a DCM/iso ether/ether mixture; m.p.=178=180° C.

$\alpha_D^{25}$=−197.3° (c=0.19; chloroform)

EXAMPLE 6

(2S)-1-[5-Chloro-1-[(2,4-dimethoxyphenyl)-sulphonyl]-3-(2-ethoxyphenyl)-2-oxo-2,3-dihydro-1H-indol-3-yl]-N,N-dimethylpyrrolidine-2-carboxamide, laevorotatory isomer (I): R$_1$=Cl; R$_2$=H; R$_3$=2-OCH$_2$CH$_3$; R$_4$=H; R$_5$=—N(CH$_3$)$_2$; R$_6$=2-OCH$_3$; R$_7$=OCH$_3$; n=1; W=O 0.11 g of 60% sodium hydride in oil is added portionwise at RT to a mixture of 0.52 g of the compound obtained in Preparation 3.6 (isomer B) in 20 ml of THF, and the mixture is left stirring for 15 minutes at RT. 0.29 g of 2,4-dimethoxybenzenesulphonyl chloride is then added and the mixture is left stirring for 1 hour at RT. The reaction mixture is poured into 100 ml of water and extracted with EtOAc, the organic phase is washed with water and dried over Na$_2$SO$_4$, and the solvent is evaporated off under vacuum. The residue is chromatographed on silica gel, eluting with a DCM/MeOH mixture (99/1; v/v). 0.54 g of the expected product is obtained after crystallization from iso ether; m.p.=145° C.

$\alpha_D^{25}$=−205° (c=0.15; chloroform)

EXAMPLE 7

(2S)-1-[5-Chloro-1-[(2,4-dimethoxyphenyl)-sulphonyl]-3-(2-hydroxyphenyl)-2-oxo-2,3-dihydro-1H-indol-3-yl]-N,N-dimethylpyrrolidine-2-carboxamide, laevorotatory isomer (I): R$_1$=Cl; R$_2$=H; R$_3$=2-OH; R$_4$=H; R$_5$=—N(CH$_3$)$_2$; R$_6$=2-OCH$_3$; R$_7$=OCH$_3$; n=1; W=O A) (2S)-1-[5-Chloro-1-[(2,4-dimethoxyphenyl)-sulphonyl]-3-(2-benzyloxyphenyl)-2-oxo-2,3-dihydro-1H-indol-3-yl]-N,N-dimethylpyrrolidine-2-carboxamide, laevorotatory isomer 0.2 g of 60% sodium hydride in oil is added portionwise at RT to a mixture of 2 g of the compound obtained in Preparation 3.27 in 50 ml of THF, and the mixture is left stirring for 15 minutes. 1.2 g of 2,4-dimethoxybenzenesulphonyl chloride are then added and the mixture is left stirring for 30 minutes at RT. The reaction mixture is poured into water and extracted with EtOAc, the organic phase is dried over Na$_2$SO$_4$ and the solvent is evaporated off under vacuum. The residue is chromatographed on silica gel, eluting with a DCM/EtOAc mixture (95/5; v/v). 2.25 g of the expected product are obtained after crystallization from iso ether.

$\alpha_D^{20}$=−245° (c=0.14; chloroform)

B) (2S)-1-[5-Chloro-1-[(2,4-dimethoxyphenyl)-sulphonyl]-3-(2-hydroxyphenyl)-2-oxo-2,3-dihydro-1H-indol-3-yl]-N,N-dimethylpyrrolidine-2-carboxamide, laevorotatory isomer 1.2 g of the compound obtained in the preceding step, 1 ml of trifluoroacetic acid, 0.5 ml of thioanisole and 10 ml of trifluoromethanesulphonic acid are mixed together at a temperature below 5° C. and the mixture is left stirring while allowing the temperature to return to RT and is then stirred for 15 minutes at RT. The reaction mixture is poured into an ice/water mixture and extracted with EtOAc, the organic phase is washed with water, with 5% NaHCO$_3$ solution and with water and dried over Na$_2$SO$_4$, and the solvent is evaporated off under vacuum. The residue is chromatographed on silica gel, eluting with a DCM/MeOH mixture (99/1; v/v). 0.6 g of the expected product is obtained; m.p.=143° C.

$\alpha_D^{20}$=−94° (c=0.12; chloroform)

$^1$H NMR: d$_6$-DMSO: δ (ppm): 1.4 to 2.0: 2up: 4H; 2.4 and 3.0: up+2s: 7H; 3.4 to 4.0: 2s: 7H; 4.5: mt: 1H; 6.8 to 7.4: up: 7H; 7.6: dd: 1H; 7.9 to 8.1: 2d: 2H; 10.0: bs: 1H

EXAMPLE 8

(2S)-1-[5-Trifluoromethoxy-1-[(2,4-dimethoxyphenyl)sulphonyl]-3-(2-methoxyphenyl)-2-oxo-2,3-dihydro-1H-indol-3-yl]-N,N-dimethylpyrrolidine-2-carboxamide, laevorotatory isomer (I): R$_1$=OCF$_3$; R$_2$=H; R$_3$=2-OCH$_3$; R$_4$=H; R$_5$=—N(CH$_3$)$_2$; R$_6$=2-OCH$_3$; R$_7$=OCH$_3$; n=1; W=O 0.035 g of 60% sodium hydride in oil is added at RT, under an argon atmosphere, to a solution of 0.371 g of the compound obtained in Preparation 3.30 in 5 ml of DMF, and the mixture is left stirring for 15 minutes. 0.208 g of 2,4-dimethoxybenzenesulphonyl chloride is then added and the mixture is left stirring for 3 hours at RT. The reaction mixture is poured into 5% K$_2$CO$_3$ solution and extracted with EtOAc, the organic phase is washed with saturated NaCl solution and dried over Na$_2$SO$_4$ and the solvent is evaporated off under vacuum. The residue is chromatographed on silica gel, eluting with a DCM/EtOAc mixture (80/20; v/v). The residue is dissolved in a minimum amount of MeOH, this solution is poured into water and the precipitate formed is spin-filtered off. 0.335 g of the expected product is obtained after drying.
$\alpha_D^{25}$=−239° (c=0.17; chloroform/MeOH, 8/2; v/v)
$^1$H NMR: $d_6$-DMSO: δ (ppm): 1.2 to 2.0: 2up: 2H; 2.1 to 2.8: 2s+up: 8H; 3.4: s: 3H; 3.6: s: 3H; 3.9: s: 3H; 4.5: d: 1H; 6.7 to 7.0: 2up: 5H; 7.2: dt: 1H; 7.4: dd: 1H; 7.7: dd: 1H; 7.9: d: 1H; 8.0: d: 1H

EXAMPLES 9 AND 10

(2S)-1-[5,6-Dichloro-1-[(2,4-dimethoxyphenyl)sulphonyl]-3-(2-methoxyphenyl)-2-oxo-2,3-dihydro-1H-indol-3-yl]-N,N-dimethylpyrrolidine-2-carboxamide, isomer A and isomer B (I): $R_1$=Cl; $R_2$=6-Cl; $R_3$=2-OCH$_3$; $R_4$=H; $R_5$=—N(CH$_3$)$_2$; $R_6$=2-OCH$_3$; $R_7$=OCH$_3$; n=1; W=O A mixture of 1.769 g of the compound obtained in Preparation 3.31 in 17 ml of DMF is cooled on an ice bath, 0.187 g of 60% sodium hydride in oil is added, under an argon atmosphere, and the mixture is left stirring for 10 minutes. 1.058 g of 2,4-dimethoxybenzenesulphonyl chloride are then added and the mixture is left stirring for 3 hours at RT. Water is added and the reaction mixture is extracted with EtOAc, the organic phase is washed with water and with saturated NaCl solution and dried over Na$_2$SO$_4$, and the solvent is evaporated off under vacuum. The residue is chromatographed on alumina, eluting with a DCM/hexane mixture (90/10; v/v). The diastereoisomers are separated:
the less polar, isomer A: compound of Example 9, which is crystallized from iso ether to give 0.308 g; m.p.=193-194° C.
$\alpha_D^{20}$=+128.1° (c=0.149 chloroform)
the more polar, isomer B: compound of Example 10, which is crystallized from iso ether and DCM to give 0.821 g; m.p. 231-232° C.
$\alpha_D^{25}$=−95.7° (c=0.116; chloroform)

EXAMPLE 11

(2S)-1-[6-Chloro-1-[(2,4-dimethoxyphenyl)-sulphonyl]-3-(2-methoxyphenyl)-5-methyl-2-oxo-2,3-dihydro-1H-indol-3-yl]-N,N-dimethylpyrrolidine-2-carboxamide, laevorotatory isomer (I): $R_1$=CH$_3$; $R_2$=6-Cl; $R_3$=2-OCH$_3$; $R_4$=H; $R_5$=—N(CH$_3$)$_2$; $R_6$=2-OCH$_3$; $R_7$=OCH$_3$; n=1; W=O A suspension of 0.295 g of the compound obtained in Preparation 3.44 (isomer B) in 3 ml of DMF is cooled to 0° C., 0.03 g of 60% sodium hydride in oil is added, under an argon atmosphere, and the mixture is left stirring for 10 minutes. 0.18 g of 2,4-dimethoxybenzenesulphonyl chloride is then added and the mixture is left stirring for 3 hours at RT. Water is added and the reaction mixture is extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on silica gel, eluting with DCM and then with a DCM/EtOAc mixture (98/2; v/v). The product obtained is taken up in an iso ether/hexane mixture and the precipitate formed is spin-filtered off. 0.193 g of the expected product is obtained; m.p.=204-206° C.
$\alpha_D^{25}$=−211.2° (c=0.11; chloroform)
$^1$H NMR: $d_6$-DMSO: δ (ppm): 1.2 to 2.2: up: 6H; 2.3: s: 3H; 2.4 and 2.8: 2s: 6H; 3.5: s: 3H; 3.8: s: 3H; 4.0: s: 3H; 4.5: d: 1H; 6.8 to 7.2: up: 5H; 7.3: dt: 1H; 7.7: dd: 1H; 7.8: s: 1H; 8.1: d: 1H

EXAMPLE 12

1-[5-Chloro-1-[(2,4-dimethoxyphenyl)-sulphonyl]-3-(2-dimethoxyphenyl)-2-oxo-2,3-dihydro-1H-indol-3-yl]-N,N-dimethylpyrrolidine-2-carboxamide (I): $R_1$=Cl; $R_2$=H; $R_3$=2-OCH$_3$; $R_4$=5-OCH$_3$; $R_5$=—N(CH$_3$)$_2$; $R_6$=2-OCH$_3$; $R_7$=OCH$_3$; n=2; W=O This compound is prepared according to the procedure described in Example 11, starting with the compound obtained in Preparation 3.51 (racemic isomer B). The product is chromatographed on silica gel, eluting with a DCM/MeOH mixture (98/2; v/v). The expected product is obtained after crystallization from a DCM/iso ether mixture; m.p.=212-214° C.

EXAMPLES 13 AND 14

(2S)-1-[5,6-Dichloro-1-[(2,4-dimethoxyphenyl)sulphonyl]-3-(2-chlorophenyl)-2-oxo-2,3-dihydro-1H-indol-3-yl]-N,N-dimethylpiperidine-2-carboxamide, isomer A and isomer B (I): $R_1$=Cl; $R_2$=6-Cl; $R_3$=2-Cl; $R_4$=H; $R_5$=—N(CH$_3$)$_2$; $R_6$=2-OCH$_3$; $R_7$=OCH$_3$; n=2; W=O These compounds are prepared according to the procedure described in Examples 9 and 10, starting with 1.821 g of the compound obtained in Preparation 3.52. The product is chromatographed on alumina, eluting with DCM and then with a DCM/MeOH mixture (95/5; v/v). The diastereoisomers are separated:
the less polar, isomer A: compound of Example 13, which is crystallized from DCM/heptane to give 0.824 g.
$\alpha_D^{25}$=+257.1° (c=0.105; chloroform)
the more polar, isomer B: compound of Example 14, which is crystallized from iso ether to give 2.032 g; m.p.=257-258° C.
$\alpha_D^{25}$=−353.7° (c=0.108; chloroform)

EXAMPLE 15

1-[3-(2-Chlorophenyl)-1-[(2,4-dimethoxyphenyl)sulphonyl]-5,6-dimethyl-2-oxo-2,3-dihydro-1H-indol-3-yl]-N,N-dimethylpiperidine-2-carboxamide (I): $R_1$=CH$_3$; $R_2$=6-CH$_3$; $R_3$=2-Cl; $R_4$=H; $R_5$=—N(CH$_3$)$_2$; $R_6$=2-OCH$_3$; $R_7$=OCH$_3$; n=2; W=O This compound is prepared according to the procedure described in Example 11, starting with the compound obtained in Preparation 3.61 (racemic isomer B). The product is chromatographed on silica gel, eluting with a DCM/MeOH mixture (98/2; v/v). The expected product is obtained after crystallization from a DCM/iso ether mixture; m.p.=268-270° C.

Working according to the procedures described in the above examples, starting with the compounds of formula (II) described in Preparations 3 and 2,4-dimethoxybenzenesulphonyl chloride, the compounds according to the invention collated in Table I below are prepared.

TABLE I

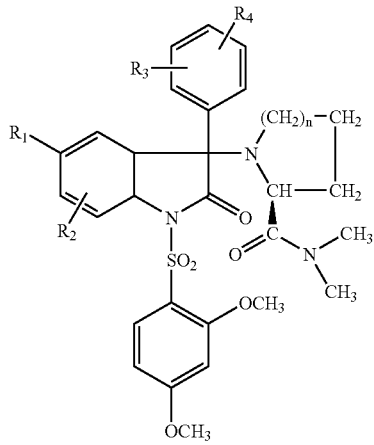

(I)

| Examples | n | R$_1$ | R$_2$ | R$_3$ | R$_4$ | m.p. ° C.; NMR crystallization solvent; $\alpha_D^{20}$ (chloroform) |
|---|---|---|---|---|---|---|
| 16 (a) | 1 | Cl | H | 3-OCH$_3$ | H | —<br>—<br>−87° (c = 0.15) |
| 17 (b) | 1 | Cl | H | 4-OCH$_3$ | H | —<br>—<br>−238° (c = 0.14) |
| 18 (c) | 1 | Cl | H | 2-OCH$_3$ | 3-OCH$_3$ | 178.5; NMR<br>iso ether<br>−68° (c = 0.15) |
| 19 (d) | 1 | Cl | H | 2-OCH$_3$ | 4-OCH$_3$ | 146; NMR<br>—<br>−216° (c = 0.15) |
| 20 (e) | 1 | Cl | H | 2-OCH$_3$ | 5-OCH$_3$ | —<br>—<br>−266.7° (c = 0.15) |
| 21 (f) | 1 | Cl | H | 2-OCH$_3$ | 6-OCH$_3$ | 213<br>—<br>−303° (c = 0.13) |
| 22 (g) | 1 | Cl | H | 3-OCH$_3$ | 5-OCH$_3$ | —<br>—<br>−226° (c = 0.15) |
| 23 (h) | 1 | Cl | H | 2,3-O—CH$_2$—O— | — | NMR<br>—<br>−81° (c = 0.14) |
| 24 (i) | 1 | Cl | H | 2-OCF$_3$ | H | —<br>—<br>−218° (c = 0.14) |
| 25 (j) | 1 | Cl | H | 2-F | H | 196<br>iso ether<br>−272° (c = 0.14) |
| 26 (k) | 1 | Cl | H | 2-OCH$_3$ | 6-CH$_3$ | 193; NMR<br>iso ether<br>−250° (c = 0.15) |
| 27 (l) | 1 | Cl | 6-Cl | 2-Cl | H | 288<br>DCM/iso ether<br>−328° (c = 0.23) |
| 28 (m) | 1 | Cl | 4-Cl | 2-Cl | H | 275-278<br>DCM/isso ether<br>−321° (c = 0.13) |
| 29 (n) | 1 | Cl | 6-CH$_3$ | 2-OCH$_3$ | H | 207-210<br>iso ether/hexane<br>−191° (c = 0.16) |
| 30 (o) | 1 | Cl | 6-OCH$_3$ | 2-Cl | H | 278 (dec.); NMR<br>DCM/iso ether<br>−318° (c = 0.16) |
| 31 (p) | 1 | Cl | 4-OCH$_3$ | 2-Cl | H | 212<br>DCM/iso ether<br>−269° (c = 0.117) |
| 32 (q) | 1 | Cl | 7-F | 2-Cl | H | —<br>DCM/iso ether/hexane<br>−206.8° (c = 0.1) |
| 33 (r) | 1 | CH$_3$ | 4-Cl | 2-OCH$_3$ | H | NMR<br>DCM/iso ether/hexane<br>−266° (c = 0.11) |
| 34 (s) | 1 | 5,6-CH$_2$CH$_2$CH$_2$— | | 2-OCH$_3$ | H | 160<br>iso ether<br>−174° (c = 0.15) |
| 35 (t) | 1 | CH$_3$ | 6-CH$_3$ | 2-OCH$_3$ | 6-CH$_3$ | 235; NMR<br>DCM/iso ether<br>— |
| 36 (u) | 2 | Cl | H | 2-OCH$_3$ | H | 148-149; NMR<br>DCM/iso ether<br>−211° (c = 0.209) |
| 37 (v) | 2 | Cl | 6-Cl | 2-OCH$_3$ | H | 239-240; NMR<br>DCM/iso ether<br>−289.3° (c = 0.102) |
| 38 (w) | 2 | Cl | 7-F | 2-Cl | H | 149-152<br>DCM/iso ether<br>−196.2° (c = 0.1) |
| 39 (x) | 2 | Cl | 6-CH$_3$ | 2-OCH$_3$ | H | 236-237; NMR<br>DCM/iso ether<br>−219.2° (c = 0.105) |
| 40 (y) | 2 | Cl | 6-CF$_3$ | 2-OCH$_3$ | H | 229<br>DCM/iso ether/hexane<br>−209.47° (c = 0.243) |

(a) This compound is prepared according to the procedure described in Example 6, starting with the compound obtained in Preparation 3.7 (isomer A). The product is chromatographed on silica gel, eluting with a DCM/MeOH mixture (99.5/0.5; v/v).
(b) This compound is prepared according to the procedure described in Example 6, starting with the compound obtained in Preparation 3.9 (isomer A). The product is chromatographed on silica gel, eluting with DCM.
(c) This compound is prepared according to the procedure described in Example 6, starting with the compound obtained in Preparation 3.12 (isomer B). The product is chromatographed on silica gel, eluting with a DCM/EtOAc mixture (95/5; v/v).
(d) This compound is prepared according to the procedure described in Example 6, starting with the compound obtained in Preparation 3.13 (isomer A). The product is chromatographed on silica gel, eluting with a DCM/MeOH mixture (99/1; v/v).
(e) This compound is prepared according to the procedure described in Example 6, starting with the compound obtained in Preparation 3.15 (isomer A). The product is chromatographed on silica gel, eluting with a DCM/EtOAc mixture (95/5; v/v).
(f) This compound is prepared according to the procedure described in Example 6, starting with the compound obtained in Preparation 3.17 (isomer A). The product is chromatographed on silica gel, eluting with a DCM/EtOAc mixture (95/5; v/v).
(g) This compound is prepared according to the procedure described in Example 6, starting with the compound obtained in Preparation 3.19 (isomer A). The product is chromatographed on silica gel, eluting with a DCM/MeOH mixture (99.5/0.5; v/v).

TABLE I-continued

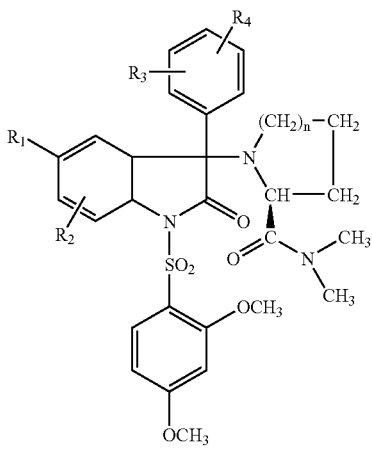

(I)

| Examples | n | $R_1$ | $R_2$ | $R_3$ | $R_4$ | m.p. °C.; NMR crystallization solvent; $\alpha_D^{20}$ (chloroform) |
|---|---|---|---|---|---|---|

(h) This compound is prepared according to the procedure described in Example 6, starting with the compound obtained in Preparation 3.21 (isomer A). The product is chromatographed on alumina, eluting with a DCM.
(i) This compound is prepared according to the procedure described in Example 6, starting with the compound obtained in Preparation 3.23 (isomer A). The product is chromatographed on silica gel, eluting with a DCM/MeOH mixture (99.5/0.5; v/v).
(j) This compound is prepared according to the procedure described in Example 6, starting with the compound obtained in Preparation 3.25 (isomer A). The product is chromatographed on silica gel, eluting with a DCM/MeOH mixture (99/1; v/v).
(k) This compound is prepared according to the procedure described in Example 6, starting with the compound obtained in Preparation 3.29 (isomer B). The product is chromatographed on silica gel, eluting with a DCM/EtOAc mixture (95/5; v/v).
(l) This compound is prepared according to the procedure described in Examples 9 and 10, starting with the compound obtained in Preparation 3.32. The product is chromatographed on alumina, eluting with a DCM/hexane mixture (90/10; v/v), the fractions enriched in the polar isomer are collected and this product is crystallized from a DCM/iso ether mixture.
(m) This compound is prepared according to the procedure described in Example 11, starting with the compound obtained in Preparation 3.34 (isomer B). The product is chromatographed on silica gel, eluting with a DCM/MeOH mixture (99/1; v/v).
(n) This compound is prepared according to the procedure described in Example 11, starting with the compound obtained in Preparation 3.36 (isomer B). The product is chromatographed on silica gel, eluting with a DCM/EtOAc mixture (80/20; v/v).
(o) This compound is prepared according to the procedure described in Example 11, starting with the compound obtained in Preparation 3.38 (isomer B). The product is chromatographed on silica gel, eluting with a DCM/MeOH mixture (98/2; v/v).
(p) This compound is prepared according to the procedure described in Example 11, starting with the compound obtained in Preparation 3.40 (isomer B). The product is chromatographed on alumina, eluting with a DCM/MeOH mixture (99.5/0.5; v/v) and then on silica, eluting with a DCM/MeOH mixture (98/2; v/v).
(q) This compound is prepared according to the procedure described in Example 11, starting with the compound obtained in Preparation 3.42 (isomer B). The product is chromatographed on silica gel, eluting with a DCM and then with a DCM/MeOH mixture (98.5/1.5; v/v).
(r) This compound is prepared according to the procedure described in Examples 9 and 10, starting with the compound obtained in Preparation 3.45. The product is chromatographed on silica gel, eluting with a DCM/MeOH mixture of from (99/1; v/v) to (98/2; v/v) and is then re-chromatographed on silica gel, eluting with a DCM/MeOH mixture (99/1; v/v) and the less polar compound is collected each time.
(s) This compound is prepared according to the procedure described in Example 6, starting with the compound obtained in Preparation 3.46. The product is chromatographed on silica gel, eluting with a DCM/EtOAc mixture (95/5; v/v) and the less polar compound is collected.

TABLE I-continued

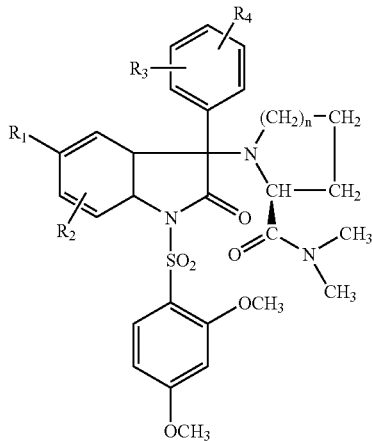

(I)

| Examples | n | $R_1$ | $R_2$ | $R_3$ | $R_4$ | m.p. °C.; NMR crystallization solvent; $\alpha_D^{20}$ (chloroform) |
|---|---|---|---|---|---|---|

(t) This compound is prepared according to the procedure described in Example 11, starting with the compound obtained in Preparation 3.47. The product is chromatographed on silica gel, eluting with a DCM/MeOH mixture (98/2; v/v).
(u) This compound is prepared according to the procedure described in Example 11, starting with the compound obtained in Preparation 3.49 (isomer B). The product is chromatographed on silica gel, eluting with a DCM and then with a DCM/EtOAc mixture (85/15; v/v).
(v) This compound is prepared according to the procedure described in Example 11, starting with the compound obtained in Preparation 3.53. The product is chromatographed on silica gel, eluting with a DCM/EtOAc mixture (70/30; v/v).
(w) This compound is prepared according to the procedure described in Example 8, starting with the compound obtained in Preparation 3.55 (isomer B). The product is chromatographed on silica gel, eluting with a DCM/MeOH mixture (98/2; v/v).
(x) This compound is prepared according to the procedure described in Example 11, starting with the compound obtained in Preparation 3.57 (isomer B). The product is chromatographed on silica gel, eluting with a DCM/EtOAc mixture (70/30; v/v).
(y) This compound is prepared according to the procedure described in Example 11, starting with the compound obtained in Preparation 3.59 (isomer B). The product is chromatographed on silica gel, eluting with a DCM and then with a DCM/EtOAc mixture (90/10; v/v).

EXAMPLE 18

$^1$H NMR: $d_6$-DMSO: δ (ppm): 1.2 to 1.8: 2mt: 4H; 2.1 to 2.8: mt+3s: 11H; 3.6 to 4.0: 3s: 9H; 4.5: mt: 1H; 6.6 to 7.2: mt: 5H; 7.3: t+dd: 1H; 7.4: mt: 1H; 7.9: dd+t: 1H; 8.1: d: 1H.

EXAMPLE 19

$^1$H NMR: $d_6$-DMSO: δ (ppm): 1.2 to 2.0: 2mt: 4H; 2.2 to 2.8: mt+2s: 8H; 3.5: s: 3H; 3.7: s: 3H; 3.8: s: 3H; 4.0: s: 3H; 4.6: d: 1H; 6.5: mt: 2H; 6.8: mt: 2H; 7.0: d: 1H; 7.5: dd: 1H; 7.6: d: 1H; 7.9: d: 1H; 8.1: d: 1H.

EXAMPLE 23

$^1$H NMR: $d_6$-DMSO: δ (ppm): 1.4 to 1.9: 2mt: 4H; 2.2 to 3.0: 2s+mt: 8H; 3.4: s: 3H; 3.8: s: 3H; 4.4: dd: 1H; 5.3 and 5.6: 2s: 2H; 6.6 to 7.0: mt: 5H; 7.2: d: 1H; 7.4: dd: 1H; 7.9 to 8.0: 2d: 2H.

EXAMPLE 26

$^1$H NMR: $d_6$-DMSO: δ (ppm): 1.1 to 1.8: m: 4H; 2.0: bs: 3H; 2.4: s: 3H; 2.5 to 2.7: mt+3s: 5H; 3.3 to 3.9: 4s: 12H; 4.2 and 4.5: 2d: 1H; 6.6: mt: 4H; 7.0 to 7.2: mt: 2H; 7.3: 2dd: 1H; 7.6: 2d: 1H; 8.0: mt: 1H.

EXAMPLE 30

$^1$H NMR: $d_6$-DMSO: δ (ppm): 1.3 to 1.9: 2mt: 4H; 2.2 to 3.0: up: 8H; 3.6: s: 3H; 3.9: s: 3H; 4.1: s: 3H; 4.5: t: 1H; 6.7: mt: 2H; 6.9: s: 1H; 7.3: up: 3H; 7.6: bs: 1H; 8.0: d: 2H.

EXAMPLE 33

$^1$H NMR: $d_6$-DMSO: δ (ppm): 1.2 to 1.9: 2mt: 4H; 2.2: s: 3H; 2.5: s: 3H; 2.5 to 3.6: 2bs: 8H; 3.7: s: 3H; 3.9: s: 3H; 4.5: d: 1H; 6.7: mt: 1H; 6.8: mt: 1H; 7.2: dt: 1H; 7.4: d: 1H; 7.7: d: 1H; 7.8: d: 1H; 8.0: d: 1H.

EXAMPLE 35

$^1$H NMR: $d_6$-DMSO: δ (ppm): 1.0 to 2.0: 2up: 4H; 2.0 to 3.0: mt: 17H; 3.3 to 3.9: 4s: 9H; 4.2 and 4.6: 2d: 1H; 6.6: up: 4H; 7.0: up: 2H; 7.6: s: 1H; 8.0: mt: 1H.

EXAMPLE 36

$^1$H NMR: $d_6$-DMSO: δ (ppm): 1.2 to 1.8: up: 6H; 2.2: bs: 2H; 2.5 to 2.8: 2bs: 6H; 3.8: s: 3H; 3.9: bs: 4H; 6.7: mt: 4H; 7.0: t: 1H; 7.2: t: 1H; 7.4: dd: 1H; 7.9: d: 1H; 8.0: d: 1H.

EXAMPLE 37

$^1$H NMR: $d_6$-DMSO: δ (ppm): 1.1 to 2.0: up: 8H; 2.1 to 2.7: 2bs: 7H; 2.8: s: 3H; 3.8: s: 3H; 4.0: s: 3H; 6.8: mt: 3H; 6.9: s: 1H; 7.0: t: 1H; 7.2: t: 1H;, 7.8: d: 1H; 7.9 to 8.0: d+s: 2H.

EXAMPLE 39

$^1$H NMR: $d_6$-DMSO: δ (ppm): 1.2 to 1.8: 2mt: 6H; 2.2: bs: 6H; 2.3: s: 3H; 2.6: bs: 2H; 2.7: s: 3H; 3.8: s: 3H; 3.9: bs: 4H; 6.6: mt: 4H; 7.0: t: 1H; 7.2: t: 1H; 7.7: s: 1H; 7.8: d: 1H; 8.0: d: 1H.

The invention claimed is:

1. A compound of formula (I):

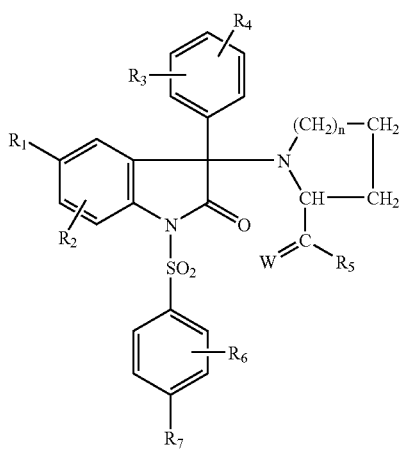

(I)

in which:

n is 2;

W represents an oxygen atom or a sulphur atom;

$R_1$ represents a halogen atom; a ($C_1$-$C_4$)alkyl; a ($C_1$-$C_4$) alkoxy; a trifluoromethyl radical; or a trifluoromethoxy radical;

$R_2$ represents a hydrogen atom; a halogen atom; a ($C_1$-$C_4$) alkyl; a ($C_1$-$C_4$)alkoxy; or a trifluoromethyl radical;

or $R_2$ is in position -6- of the indol-2-one ring;

$R_3$ represents a halogen atom; a hydroxyl; a ($C_1$-$C_2$)alkyl; a ($C_1$-$C_2$)alkoxy; or a trifluoromethoxy radical;

$R_4$ represents a hydrogen atom; a halogen atom; a ($C_1$-$C_2$) alkyl; or a ($C_1$-$C_2$)alkoxy;

or $R_3$ is in position -2- of the phenyl, $R_4$ is in position -3- of the phenyl and $R_3$ and $R_4$ together represent a methylenedioxy radical;

$R_5$ represents an ethylamino group; a dimethylamino group; a 1-azetidinyl radical; or a ($C_1$-$C_2$)alkoxy;

$R_6$ represents a ($C_1$-$C_4$)alkoxy; and $R_7$ represents a ($C_1$-$C_4$)alkoxy.

2. A compound according to claim 1, in the form of an optically pure isomer.

3. A compound according to claim 2, of formula (Ia):

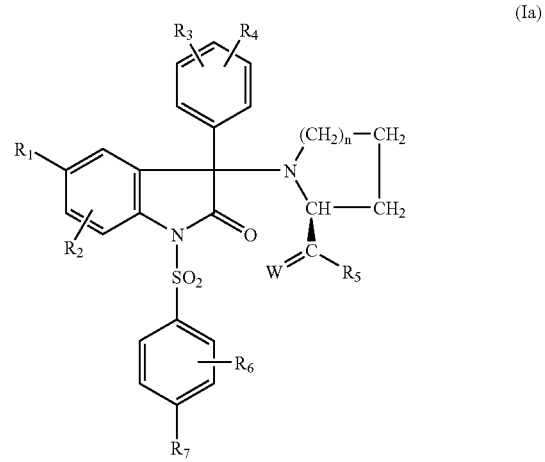

(Ia)

in which:

the carbon atom bearing the substituent —C(W)$R_5$ has the (S) configuration and the carbon atom in position -3- of the indol-2-one has either the (R) configuration or the (S) configuration.

4. A compound according to claim 3, in the form of the laevorotatory isomer.

5. A compound according to claim 1 in which:

n is 2;

W represents an oxygen atom;

$R_1$ represents a chlorine atom or a methyl radical;

$R_2$ represents a hydrogen atom or is in position -6- of the indol-2-one and represents a chlorine atom, a methyl radical, a methoxy radical or a trifluoromethyl radical;

$R_3$ is in position -2- of the phenyl and represents a methoxy radical, a chlorine atom or a fluorine atom;

$R_4$ represents a hydrogen atom, a methyl radical or a methoxy radical;

or $R_3$ is in position -2- of the phenyl, $R_4$ is in position -3- of the phenyl and $R_3$ and $R_4$ together represent a methylenedioxy radical;

$R_5$ represents a dimethylamino group or a methoxy radical;

$R_6$ is in position -2- of the phenyl and represents a methoxy radical; and $R_7$ represents a methoxy radical.

6. A compound chosen from:
(2S)-1-[5,6-Dichloro-1-[(2,4-dimethoxyphenyl)-sulphonyl]-3-(2-chlorophenyl)-2-oxo-2,3-dihydro-1H-indol-3-yl]-N,N-dimethylpiperidine-2-carboxamide, laevorotatory isomer;
(2S)-1-[5,6-Dichloro-1-[(2,4-dimethoxyphenyl)-sulphonyl]-3-(2-methoxyphenyl)-2-oxo-2,3-dihydro-1H-indol-3-yl]-N,N-dimethylpiperidine-2-carboxamide, laevorotatory isomer;
(2S)-1-[5-Chloro-1-[(2,4-dimethoxyphenyl)-sulphonyl]-3-(2-methoxyphenyl)-6-methyl-2-oxo-2,3-dihydro-1H-indol-3-yl]-N,N-dimethylpiperidine-2-carboxamide, laevorotatory isomer; and
(2S)-1-[5-Chloro-1-[(2,4-dimethoxyphenyl)-sulphonyl]-3-(2-methoxyphenyl)-6-trifluoromethyl-2-oxo-2,3-dihydro-1H-indol-3-yl]-N,N-dimethylpiperidine-2-carboxamide, laevorotatory isomer.

7. A compound according to claim 3 in which:
n is 2;
W represents an oxygen atom;
$R_1$ represents a chlorine atom or a methyl radical;
$R_2$ represents a hydrogen atom or is in position -6- of the indol-2-one and represents a chlorine atom, a methyl radical, a methoxy radical or a trifluoromethyl radical;
$R_3$ is in position -2- of the phenyl and represents a methoxy radical, a chlorine atom or a fluorine atom;
$R_4$ represents a hydrogen atom, a methyl radical or a methoxy radical;
or $R_3$ is in position -2- of the phenyl, $R_4$ is in position -3- of the phenyl and $R_3$ and $R_4$ together represent a methylenedioxy radical;
$R_5$ represents a dimethylamino group or a methoxy radical;
$R_6$ is in position -2- of the phenyl and represents a methoxy radical; and
$R_7$ represents a methoxy radical.

8. A compound according to claim 4 in which:
n is 2;
W represents an oxygen atom;
$R_1$ represents a chlorine atom or a methyl radical;
$R_2$ represents a hydrogen atom or is in position -6- of the indol-2-one and represents a chlorine atom, a methyl radical, a methoxy radical or a trifluoromethyl radical;
$R_3$ is in position -2- of the phenyl and represents a methoxy radical, a chlorine atom or a fluorine atom;
$R_4$ represents a hydrogen atom, a methyl radical or a methoxy radical;
or $R_3$ is in position -2- of the phenyl, $R_4$ is in position -3- of the phenyl and $R_3$ and $R_4$ together represent a methylenedioxy radical;
$R_5$ represents a dimethylamino group or a methoxy radical;
$R_6$ is in position -2- of the phenyl and represents a methoxy radical; and
$R_7$ represents a methoxy radical.

9. A pharmaceutical composition comprising a compound according to claim 1 and a pharmaceutically acceptable excipient.

10. A pharmaceutical composition comprising a compound according to claim 5 and a pharmaceutically acceptable excipient.

11. A pharmaceutical composition comprising a compound according to claim 6 and a pharmaceutically acceptable excipient.

12. A pharmaceutical composition comprising a compound according to claim 7 and a pharmaceutically acceptable excipient.

* * * * *